US009393255B2

(12) United States Patent
Tutino et al.

(10) Patent No.: US 9,393,255 B2
(45) Date of Patent: Jul. 19, 2016

(54) PHARMACEUTICAL COMPOSITIONS OF CYTIDINE ANALOGS AND METHODS OF USE THEREOF

(75) Inventors: Anthony Tutino, New Providence, NJ (US); Mei Lai, Longmont, CO (US); Jeffrey B. Etter, Boulder, CO (US)

(73) Assignee: Celgene Corporation, Summit, NJ (US)

( * ) Notice: Subject to any disclaimer, the term of this patent is extended or adjusted under 35 U.S.C. 154(b) by 662 days.

(21) Appl. No.: 13/363,008

(22) Filed: Jan. 31, 2012

(65) Prior Publication Data

US 2012/0196823 A1    Aug. 2, 2012

Related U.S. Application Data

(60) Provisional application No. 61/438,110, filed on Jan. 31, 2011.

(51) Int. Cl.
| | | |
|---|---|---|
| *A61K 31/706* | (2006.01) | |
| *A61P 35/00* | (2006.01) | |
| *A61P 35/02* | (2006.01) | |
| *A61K 9/00* | (2006.01) | |

(52) U.S. Cl.
CPC ............ *A61K 31/706* (2013.01); *A61K 9/0019* (2013.01)

(58) Field of Classification Search
CPC .................................................. A61K 31/706
See application file for complete search history.

(56) References Cited

U.S. PATENT DOCUMENTS

| | | | | |
|---|---|---|---|---|
| 6,140,346 | A * | 10/2000 | Andrulis et al. .............. | 514/323 |
| 6,887,855 | B2 * | 5/2005 | Ionescu et al. .................. | 514/43 |
| 6,943,249 | B2 | 9/2005 | Ionescu et al. | |
| 6,982,253 | B2 * | 1/2006 | Joshi-Hangal et al. ......... | 514/49 |
| 7,038,038 | B2 | 5/2006 | Ionescu et al. | |
| 7,078,518 | B2 | 7/2006 | Ionescu et al. | |
| 7,250,416 | B2 † | 7/2007 | Phiasivongsa | |
| 7,700,770 | B2 | 4/2010 | Ionescu et al. | |
| 7,772,199 | B2 | 8/2010 | Ionescu et al. | |
| 7,858,774 | B2 | 12/2010 | Ionescu et al. | |
| 8,058,424 | B2 | 11/2011 | Ionescu et al. | |
| 8,211,862 | B2 | 7/2012 | Ionescu et al. | |
| 2003/0229047 | A1 | 12/2003 | Joshi-Hangal et al. | |
| 2006/0128653 | A1 | 6/2006 | Tang et al. | |
| 2009/0286752 | A1 | 11/2009 | Etter et al. | |
| 2011/0042247 | A1 * | 2/2011 | Kocherlakota et al. ....... | 206/223 |

FOREIGN PATENT DOCUMENTS

| | | |
|---|---|---|
| CN | 101584670 A | 11/2009 |
| CN | 101584670 A2 | 11/2009 |
| CN | 101637458 A | 2/2010 |
| CN | 101584670 B | 4/2011 |
| JP | 2008-523096 A | 7/2008 |
| WO | 2004/041195 A2 | 5/2004 |
| WO | WO 2004/041195 | 5/2004 |
| WO | WO 2004/082619 | 9/2004 |
| WO | WO 2004/082822 | 9/2004 |
| WO | WO 2006/034154 | 3/2006 |
| WO | 2006/071491 A1 | 7/2006 |
| WO | WO 2008/088779 | 7/2008 |
| WO | WO 2009/016617 | 2/2009 |
| WO | WO 2009/139888 | 11/2009 |
| WO | WO 2011/014541 | 2/2011 |
| WO | WO 2012/135405 | 10/2012 |

OTHER PUBLICATIONS

Dai et al., "Decitabine lyophilized powder injection for treating myrelodysplastic syndrome comprises decitabine and mixed solvent consisting of tert-butyl alcohol and water for injection," CN Patent No. 101584670 A, (Official Publication Date Nov. 25, 2009). Database WPI Week 198804 Thomson Scientific, London, GB; AN 2009-S18533.

Huo et al., "Preparing stable decitabine lyophilized composition comprises: (a) adding pH regulator(s) to water, adding the decitabine or mixture of decitabine andlyophilization supporter to the solution, and filtering, filling and lyophilizing," CN Patent No. 101637458 A (Official Publication Date Feb. 3, 2010) Database WPI Week 198804 Thomson Scientific, London, GB; AN 2010-B595636.

Tutino et al., 2011, "Cold Water Reconstitution of Vidaza® with Subsequent Refrigerated Storage Prolongs Drug Stability," EJHP Practice, 17(5), 24-25.

Vidaza® Prescribing Information, Revised Jan. 2012, at http://www.vidaza.com/patient/default.aspx.

Chan et al., Journal of Pharmaceutical Sciences, 68(7), 807-12 (1979).

Lin et al., Journal of Pharmaceutical Sciences, 70(11), 1228-32 (1981).

Mojaverian et al., Journal of Pharmacy and Pharmacology, 36,728-33 (1984).

Notari et al., Journal of Pharmaceutical Sciences, 64(7), 1148-57 (1975).

Sanderson et al., Nature News, Mar. 16, 2009, available at http://www.nature.com/news/2009/090316/full/458269a.html.

Hartich et al., "Stability of azacitidine in lactated Ringer's injection frozen in polypropylene syringes," Am. J. Hospital Pharmacy, 46:2500-2505 (1989).

Vidaza® (azacitidine for injection), [online], 2007, Efficacy Supplement with Clinical Data to Support, Label, retrieved Oct. 27, 2015, online <URL:http://www.accessdata.fda.gov/drugsatfda_docs/label/2007/050794s0051bl.pdf>.

EMEA, VIDAZA Product Information, 04 pages, Jan. 12, 2009, EMEA website, Internet.†

* cited by examiner
† cited by third party

*Primary Examiner* — Layla Berry
(74) *Attorney, Agent, or Firm* — Jones Day

(57) ABSTRACT

The present disclosure provides pharmaceutical compositions comprising cytidine analogs for parenteral administration. Also provided are methods of preparing the compositions and methods of treating diseases and disorders using the compositions provided herein.

36 Claims, 8 Drawing Sheets

PHARMACEUTICAL COMPOSITIONS OF CYTIDINE ANALOGS AND METHODS OF USE THEREOF

I. CROSS REFERENCE TO RELATED APPLICATIONS

This application claims priority to U.S. Provisional Patent Application No. 61/438,110, filed Jan. 31, 2011, the content of which is hereby incorporated by reference herein in its entirety.

II. FIELD

Provided herein are pharmaceutical compositions comprising a cytidine analog, or a salt, solvate, hydrate, precursor, or derivative thereof. Also provided are methods for preparing the compositions and methods for using the compositions to treat diseases and disorders including cancer, disorders related to abnormal cell proliferation, hematologic disorders, and immune disorders, among others.

III. BACKGROUND

Cancer is a major worldwide public health problem; in the United States alone, approximately 570,000 cancer-related deaths were expected in 2005. See, e.g., Jemal et al., *CA Cancer J. Clin.* 55(1):10-30 (2005). Many types of cancer have been described in the medical literature. Examples include cancer of the blood, bone, lymphatic system, lung (e.g., non-small-cell lung cancer and small-cell lung cancer), colon, breast, prostate, ovary, brain, and intestine. The incidence of cancer continues to climb as the general population ages and as new forms of cancer develop. A continuing need exists for effective therapies to treat subjects with cancer.

Myelodysplastic syndromes (MDS) refers to a diverse group of hematopoietic stem cell disorders. MDS affects approximately 40,000-50,000 people in the U.S. and 75,000-85,000 subjects in Europe. MDS may be characterized by a cellular marrow with impaired morphology and maturation (dysmyelopoiesis), peripheral blood cytopenias, and a variable risk of progression to acute leukemia, resulting from ineffective blood cell production. See, e.g., *The Merck Manual* 953 (17th ed. 1999); List et al., *J. Clin. Oncol.* 8:1424 (1990).

MDS are grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS may develop complications related to anemia, neutropenia (infections), and/or thrombocytopenia (bleeding). From about 10% to about 70% of patients with MDS may develop acute leukemia. In the early stages of MDS, the main cause of cytopenias is increased programmed cell death (apoptosis). As the disease progresses and converts into leukemia, a proliferation of leukemic cells overwhelms the healthy marrow. The disease course differs, with some cases behaving as an indolent disease and others behaving aggressively with a very short clinical course that converts into an acute form of leukemia. The majority of people with higher risk MDS eventually experience bone marrow failure. Up to 50% of MDS patients succumb to complications, such as infection or bleeding, before progressing to acute myeloid leukemia (or acute myelogenous leukemia) (AML).

Primary and secondary MDS are defined by taking into account patients' prior history: previous treatments with chemotherapy, radiotherapy or professional exposure to toxic substances are factors delineating secondary MDS (sMDS) from primary MDS. Cytogenetically, one difference between the two groups is the complexity of abnormal karyotypes; single chromosome aberrations are typical for primary MDS, while multiple changes are more frequently seen in secondary disorders. Some drugs may have specific targets such as hydroxyurea for 17p and topoisomerases inhibitors for 11q23 and $21_822$. The genetic changes in the malignant cells of MDS result mainly in the loss of genetic material, including probable tumor suppressor genes.

An international group of hematologists, the French-American-British (FAB) Cooperative Group, classified MDS into five subgroups, differentiating them from AML. See, e.g., *The Merck Manual* 954 (17th ed. 1999); Bennett J. M., et al., *Ann. Intern. Med.*, 103(4): 620-25 (1985); and Besa E. C., *Med. Clin. North Am.* 76(3): 599-617 (1992). An underlying trilineage dysplastic change in the bone marrow cells of the patients is found in all subtypes. Information is available regarding the pathobiology of MDS, certain MDS classification systems, and particular methods of treating and managing MDS. See, e.g., U.S. Pat. No. 7,189,740 (issued Mar. 13, 2007), which is incorporated by reference herein in its entirety.

Nucleoside analogs have been used clinically for the treatment of viral infections and cancer. Most nucleoside analogs are classified as anti-metabolites. After they enter the cell, nucleoside analogs are successively phosphorylated to nucleoside 5'-mono-phosphates, di-phosphates, and tri-phosphates.

5-Azacytidine (National Service Center designation NSC-102816; CAS Registry Number 320-67-2), also known as azacitidine, AZA, or 4-amino-1-β-D-ribofuranosyl-1,3,5-triazin-2(1H)-one, is currently marketed as the drug product VIDAZA®. 5-Azacytidine may be used to treat MDS patients having the following FAB subtypes: refractory anemia (RA) or refractory anemia with ringed sideroblasts (RARS) (if accompanied by neutropenia or thrombocytopenia or requiring transfusions), refractory anemia with excess blasts (RAEB), refractory anemia with excess blasts in transformation (RAEB-T), and chronic myelomonocytic leukemia (CMMoL). 5-Azacytidine is a nucleoside analog, more specifically a cytidine analog. 5-Azacytidine is a nucleoside metabolic inhibitor. A structural difference between 5-azacytidine and its related natural nucleoside is the presence of a nitrogen at position 5 of the cytosine ring in place of a carbon. 5-Azacytidine may be defined as having a molecular formula $C_8H_{12}N_4O_5$, a molecular weight of 244.21 grams per mole, and the following structure:

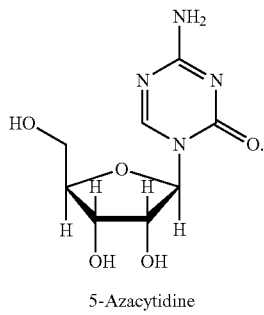

5-Azacytidine

Other members of the class of cytidine analogs include, for example: 5-aza-2'-deoxycytidine (Decitabine or 5-aza-CdR); 1-β-D-arabinofuranosylcytosine (Cytarabine or ara-C);

pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; and elaidic acid cytarabine.

After incorporation into replicating DNA, 5-azacytidine and 5-aza-2'-deoxycytidine (decitabine) form covalent complexes with DNA methyltransferases. DNA methyltransferases are responsible for de novo DNA methylation and for reproducing established methylation patterns in daughter DNA strands of replicating DNA. Inhibition of DNA methyltransferases by 5-azacytidine or 5-aza-2'-deoxycytidine leads to DNA hypomethylation, thereby restoring normal functions to morphologically dysplastic, immature hematopoietic cells and cancer cells by re-expression of genes involved in normal cell cycle regulation, differentiation and death. The cytotoxic effects of these cytidine analogs cause the death of rapidly dividing cells, including cancer cells, that are no longer responsive to normal cell growth control mechanisms. 5-Azacytidine, unlike 5-aza-2'-deoxycytidine, also incorporates into RNA. The cytotoxic effects of 5-azacytidine may result from multiple mechanisms, including inhibition of DNA, RNA, and protein synthesis, incorporation into RNA and DNA, and activation of DNA damage pathways.

5-Azacytidine and 5-aza-2'-deoxycytidine have been tested in clinical trials and showed significant anti-tumor activity, such as, for example, in the treatment of MDS, AML, chronic myelogenous leukemia (CML), acute lymphocytic leukemia (ALL), and non Hodgkin's lymphoma (NHL). See, e.g., Aparicio et al., *Curr. Opin. Invest. Drugs* 3(4): 627-33 (2002). 5-Azacytidine has undergone NCI-sponsored trials for the treatment of MDS and has been approved for treating all FAB subtypes of MDS. See, e.g., Kornblith et al., *J. Clin. Oncol.* 20(10): 2441-52 (2002); Silverman et al., *J. Clin. Oncol.* 20(10): 2429-40 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., *Lancet Oncol.*, 2009, 10(3):223-32. In the EU, VIDAZA® is approved for treatment of higher-risk MDS, chronic myelomonocytic leukemia (CMML, 10-29% marrow blasts without myeloproliferative disorder), and WHO-defined acute myeloid leukemia with 20% to 30% blasts and multi-lineage dysplasia.

5-Azacytidine and other cytidine analogs are approved for subcutaneous (SC) or intravenous (IV) administration to treat various proliferative disorders. The s-triazine ring of 5-azacytidine has a particular sensitivity to water. See, e.g., Beisler, *J. Med. Chem.*, 1978, 21(2), 204-08; Chan, et al., *J. Pharm. Sci.*, 1979, 68(7), 807-12. 5-Azacytidine is rapidly degraded in water. This characteristic has made the storage, handling, and administration of liquid formulations of 5-azacytidine a potential challenge. In addition, cytidine analogs may have limited aqueous solubility, for example, at a low temperature. As a result, the administration of liquid formulations of cytidine analogs may be difficult due to a combination of chemical instability and/or poor aqueous solubility.

Therefore, a great need remains for formulations and dosage forms of cytidine analogs (e.g., 5-azacytidine) and methods of preparing and using the formulations and dosage forms, to potentially permit, inter alia, convenient administration to patients, limited amount of impurities upon storage, suitable impurity profile to minimize potential toxicity, accurate delivery of intended dose, development of improved treatment regimens that maximize biologic activity, use of cytidine analogs for treating new diseases or disorders or new patient populations; and/or other potential advantageous benefits.

Citation of any references in this Section of the application is not to be construed as an admission that such references is prior art to the present application.

IV. SUMMARY

Provided herein are pharmaceutical compositions comprising a cytidine analog (e.g., 5-azacytidine or decitabine), or a salt, solvate, hydrate, precursor, or derivative thereof. Also provided are methods of preparing the compositions. Also provided are methods of using the compositions to treat diseases and disorders, including cancer, disorders related to abnormal cell proliferation, and hematologic disorders, among others.

In specific embodiments, provided herein is a liquid pharmaceutical composition (e.g., a suspension, solution, or emulsion) comprising a cytidine analog and cold water, which is substantially free of impurities, and/or which is sterile. In specific embodiments, provided herein is a liquid pharmaceutical composition (e.g., a suspension, solution, or emulsion) prepared from contacting cold water (e.g., cold sterile water, for example, cold sterile water-for-injection) (e.g., having a temperature of less than about 8° C., or a temperature of between about 2° C. and about 8° C., or a temperature of about 5° C., or a temperature of about 0° C.) with a solid pharmaceutical composition (e.g., a sterile solid or a sterile lyophilized powder) comprising a cytidine analog (e.g., 5-azacytidine or decitabine). In specific embodiments, the liquid pharmaceutical composition prepared from cold water is stored refrigerated (e.g., at a temperature of less than about 8° C., or a temperature of between about 2° C. and about 8° C., or a temperature of about 5° C., or a temperature of about 0° C.) or frozen (e.g., at a temperature of less than about 0° C., or at a temperature of about −20° C., or at a temperature of less than about −20° C.) for a certain period of time (e.g., up to 16 hr, up to 18 hr, up to 20 hr, up to 22 hr, or up to 24 hr; or about 1, 2, 3, 4, 5, 6, or 7 days; or greater than 7 days). In specific embodiments, the storage step occurs in less than 1 min, less than 3 min, less than 5 min, less than 10 min, less than 15 min, less than 30 min, or less than 45 min from the time when the cold water is mixed with the solid pharmaceutical composition. In specific embodiments, the liquid pharmaceutical composition that is stored refrigerated or frozen is allowed to warm to about ambient temperature (e.g., over a period of about 15, 30, 45, or 60 min; or greater than 60 min) (e.g., to a temperature of about 12° C., about 14° C., about 16° C., about 18° C., about 20° C., about 22° C., about 24° C., about 25° C., about 26° C., about 28° C., or about 30° C.) prior to parenteral use. In one embodiment, the liquid pharmaceutical composition is substantially free of impurities after storage (e.g., not more than 1%, not more than 2%, not more than 3%, not more than 4%, or not more than 5% w/w change in the amount of cytidine analog present in the composition or loss of potency, as compared to that prior to reconstitution or storage). In one embodiment, the liquid pharmaceutical composition remains sterile after storage. In one embodiment, the liquid pharmaceutical composition is a single unit dosage form. In one embodiment, the liquid pharmaceutical composition is a suspension. In one embodiment, the liquid pharmaceutical composition is a solution. In one embodiment, the liquid pharmaceutical composition is an emulsion. In one embodiment, the cytidine analog is 5-azacytidine. In one embodiment, the cytidine analog is decitabine. In one embodiment, provided herein is a method of preparing a liquid pharmaceutical composition described herein. In one embodiment, provided herein is a method of using a liquid pharmaceutical composition to treat a disease or disorder disclosed herein. In one embodiment, provided herein is a liquid pharmaceutical composition for use to treat a disease or disorder disclosed herein. In one embodiment, provided herein is a liquid pharmaceutical composition for parenteral use in a subject (e.g., a mammal or a human).

In one embodiment, the pharmaceutical compositions provided herein are useful for parenteral administration. In one embodiment, the pharmaceutical composition provided herein is a solid composition (e.g., a lyophilized powder) comprising a cytidine analog, for use to be reconstituted with water or with a liquid vehicle as provided herein elsewhere, to render a liquid dosage form or composition (e.g., a suspension or a solution) suitable for parenteral use. In one embodiment, provided herein is a liquid dosage form or composition (e.g., a suspension or a solution) comprising a cytidine analog prepared using a method described herein.

In one embodiment, the solid composition and/or the water or liquid vehicle used in reconstitution of the solid composition are sterile (e.g., pyrogen-free). In one embodiment, the water or liquid vehicle used in reconstitution of the solid composition is cold or pre-cooled (e.g., having a temperature of less than about 10° C., less than about 8° C., less than about 6° C., less than about 4° C., less than about 2° C., less than about 1° C., from about 2° C. to about 8° C., from about 2° C. to about 6° C., or from about 2° C. to about 4° C.). In one embodiment, refrigerated water-for-injection (e.g., having a temperature of less than about 10° C., less than about 8° C., less than about 6° C., less than about 4° C., less than about 2° C., less than about 1° C., from about 2° C. to about 8° C., from about 2° C. to about 6° C., or from about 2° C. to about 4° C.) is used in reconstitution of a solid composition comprising a cytidine analog (e.g., 5-azacytidine or decitabine).

In one embodiment, the liquid composition prepared by reconstitution of a solid composition comprising a cytidine analog with cold or pre-cooled water or with a cold or pre-cooled liquid vehicle is stored refrigerated (e.g., at a temperature of less than about 10° C., less than about 8° C., less than about 6° C., less than about 4° C., less than about 2° C., less than about 1° C., from about 2° C. to about 8° C., from about 2° C. to about 6° C., or from about 2° C. to about 4° C.) or stored frozen (e.g., at a temperature of less than about −5° C., less than about −10° C., less than about −15° C., less than about −20° C., less than about −30° C., or less than about −40° C.). In one embodiment, the liquid composition is stored refrigerated or frozen over a certain period of time (e.g., up to 12 hr, up to 14 hr, up to 16 hr, up to 18 hr, up to 20 hr, up to 22 hr, up to 1 day, up to 2 days, up to 3 days, up to 4 days, up to 5 days, up to 6 days, up to 7 days, up to 14 days, or greater than 14 days). In one embodiment, the refrigerated or frozen composition is placed at about ambient temperature for a certain period of time (e.g., about 10 min, about 15 min, about 20 min, about 25 min, about 30 min, about 40 min, about 45 min, about 50 min, about 60 min, about 75 min, about 90 min, about 120 min, or greater than 120 min) before parenteral use. In one embodiment, after storage, the liquid composition comprising a cytidine analog is substantially free of impurities (e.g., impurities present in the composition at less than 10%, less than 8%, less than 6%, less than 5%, less than 4%, less than 3%, less than 2%, less than 1%, less than 0.5%, or less than 0.1% w/w relative to the amount of cytidine analog in the composition). In one embodiment, after storage and warming to about ambient temperature, the liquid composition comprising a cytidine analog is substantially free of impurities (e.g., impurities present in the composition at less than 10%, less than 8%, less than 6%, less than 5%, less than 4%, less than 3%, less than 2%, less than 1%, less than 0.5%, or less than 0.1% w/w relative to the amount of cytidine analog in the composition). In one embodiment, after storage and warming to about ambient temperature, the liquid composition comprising a cytidine analog is a redispersed suspension or solution. In one embodiment, after storage and warming to about ambient temperature, the liquid composition comprising a cytidine analog remains sterile.

In one embodiment, the pharmaceutical composition provided herein is a liquid composition (e.g., a suspension or a solution) comprising a cytidine analog, which is substantially free of impurities after storage (e.g., refrigerated or frozen). In certain embodiments, such liquid composition is suitable for parenteral administration. In certain embodiments, such liquid composition facilitates the accurate delivery of an intended dose of a cytidine analog (e.g., 5-azacytidine or decitabine). In certain embodiments, such liquid composition minimizes any undesired toxicity derived from impurities. In certain embodiments, such liquid composition has prolonged in-use time. In certain embodiments, such liquid composition can be used more conveniently by pharmacists or patients.

In one embodiment, provided herein are methods of preparing a liquid composition (e.g., a suspension or a solution) comprising a cytidine analog, which is substantially free of impurities. In one embodiment, provided herein are methods of preparing a liquid composition (e.g., a suspension or a solution) comprising a cytidine analog, which has a prolonged in-use time. In certain embodiments, such method comprises reconstituting or mixing a solid composition provided herein (e.g., a lyophilized powder) comprising a cytidine analog (e.g., 5-azacytidine or decitabine) with cold water or a cold aqueous vehicle (e.g., having a temperature of less than about 10° C., less than about 8° C., less than about 6° C., less than about 4° C., less than about 2° C., less than about 1° C., from about 2° C. to about 8° C., from about 2° C. to about 6° C., or from about 2° C. to about 4° C.) to yield a liquid composition (e.g., a suspension or a solution). In one embodiment, the pharmaceutical composition provided herein (e.g., a liquid composition comprising a cytidine analog) is stored for a certain period of time (e.g., up to 12 hr, up to 14 hr, up to 16 hr, up to 18 hr, up to 20 hr, up to 22 hr, up to 1 day, up to 2 days, up to 3 days, up to 4 days, up to 5 days, up to 6 days, up to 7 days, up to 14 days, or greater than 14 days) and is substantially free of impurities after such storage. In certain embodiments, the pharmaceutical composition may be stored refrigerated (e.g., at a temperature of between about 2° C. and about 8° C.) or frozen (e.g., at a temperature of about −20° C.) prior to use.

In certain embodiments, the cytidine analog is 5-azacytidine. In other embodiments, the cytidine analog is 5-aza-2'-deoxycytidine (decitabine or 5-aza-CdR). In yet other embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); N⁴-octadecyl-cytarabine; elaidic acid cytarabine; or their derivatives or related analogs.

In one embodiment, provided herein is a solid pharmaceutical composition (e.g., a lyophilized powder), comprising a cytidine analog (e.g., 5-azacytidine). In one embodiment, provided herein is a liquid pharmaceutical composition, e.g., a solution or a suspension, comprising a cytidine analog (e.g., 5-azacytidine). In one embodiment, the solid or liquid composition further comprises one or more excipient(s) provided herein, such as, e.g., mannitol. In one embodiment, the solid pharmaceutical composition provided herein is reconstituted with water to provide a solution or a suspension. In one embodiment, the solid pharmaceutical composition provided herein is reconstituted with an aqueous vehicle to provide a solution or a suspension. In one embodiment, the water or aqueous vehicle is sterile and pre-cooled to a certain temperature before being mixed with the solid composition. In one embodiment, the sterile water or sterile aqueous vehicle is pre-cooled to a temperature of about 10° C., about 8° C., about 6° C., about 5° C., about 4° C., about 3° C., about 2° C., about 1° C., or about 0° C., before being mixed with the solid composition. In certain embodiments, mixing a solid pharmaceutical composition provided herein (e.g., a sterile lyophilized powder comprising a cytidine analog, e.g., 5-azacytidine) with cold sterile water (e.g., sterile water at a temperature of about 10° C., about 8° C., about 6° C., about 5° C., about 4° C., about 3° C., about 2° C., about 1° C., or about 0° C.) provides a liquid dosage form (e.g., a sterile suspension or a sterile solution comprising a cytidine analog, e.g., 5-azacytidine), which is substantially free of impurities.

Certain embodiments herein provide pharmaceutical compositions that are single unit dosage forms comprising a cytidine analog (e.g., 5-azacytidine). In one embodiment, provided herein is a pre-packaged sterile lyophilized powder comprising a certain amount of a cytidine analog (e.g., about 100 mg of 5-azacytidine) for use in the preparation of a liquid formulation (e.g., a suspension or a solution) for parenteral use. In one embodiment, the single unit dosage forms optionally further comprise one or more excipient(s), such as, e.g., mannitol. In one embodiment, provided herein is a pre-packaged sterile lyophilized powder comprising about 100 mg of 5-azacytidine, and optionally further comprising one or more excipient(s), such as, e.g., mannitol. In one embodiment, provided herein is a pre-packaged sterile lyophilized powder comprising about 100 mg of 5-azacytidine and about 100 mg of mannitol. In certain embodiments, the pre-packaged sterile lyophilized powder is reconstituted with cold sterile water or a cold sterile aqueous vehicle to yield a liquid dosage form (e.g., a suspension or a solution) for parenteral administration in a subject in need thereof (e.g., subcutaneous or intravenous administration). When intravenous administration is contemplated, the reconstituted liquid dosage form may be further diluted with sterile water or a sterile aqueous vehicle to form a solution. In one embodiment, the water or aqueous vehicle is pre-cooled to a certain temperature before being mixed with the lyophilized powder. In one embodiment, the water or aqueous vehicle is pre-cooled to a temperature of about 10° C., about 8° C., about 6° C., about 5° C., about 4° C., about 3° C., about 2° C., about 1° C., about 0° C., from about 2° C. to about 8° C., from about 2° C. to about 6° C., or from about 2° C. to about 4° C., before being mixed with the lyophilized powder. In one embodiment, the lyophilized powder is packaged in a single-use vial (i.e., unused portions of each vial are discarded and not saved for later administration). In some embodiments, the content(s) of one or more vial(s) may be reconstituted and combined to deliver an intended dose of the cytidine analog (e.g., 5-azacytidine) to a subject in need thereof.

Certain embodiments herein provide methods of preparing pharmaceutical compositions of cytidine analogs (e.g., 5-azacytidine or decitabine) intended for parenteral delivery. In specific embodiments, provided herein is a method of preparing a liquid dosage form of 5-azacytidine using cold sterile water or a cold sterile aqueous vehicle. In specific embodiments, provided herein is a method of preparing a liquid dosage form of decitabine using cold sterile water or a cold sterile aqueous vehicle. In specific embodiments, provided herein is a method of preparing a liquid dosage form of 5-azacytidine comprising the step of reconstituting (i.e., mixing) a sterile lyophilized powder comprising 5-azacytidine and optionally one or more excipient(s) (e.g., mannitol) with cold sterile water or a cold sterile aqueous vehicle. In specific embodiments, provided herein is a method of preparing a liquid dosage form of decitabine comprising the step of reconstituting (i.e., mixing) a sterile lyophilized powder comprising decitabine and optionally one or more excipient(s) with cold sterile water or a cold sterile aqueous vehicle. Further provided herein are kits comprising a solid dosage form of a cytidine analog, which may be reconstituted to generate a liquid dosage form of the cytidine analog suitable for parenteral use. Further provided are articles of manufacture containing packaging material, a formulation of a cytidine analog, and a label that indicates the method of using the formulation (e.g., methods of reconstituting the formulation comprising the cytidine analog, and methods of use) for the treatment of certain diseases or disorders including, e.g., a cancer, a disorder related to abnormal cell proliferation, a hematologic disorder, or an immune disorder.

Certain embodiments herein provide methods of using the pharmaceutical compositions provided herein to treat diseases or disorders including, e.g., cancer, disorders related to abnormal cell proliferation, hematologic disorders, or immune disorders, among others. In certain embodiments, the pharmaceutical compositions of cytidine analogs are parenterally administered to subjects in need thereof to treat a cancer or a hematological disorder, such as, for example, MDS, AML, ALL, CML, NHL, leukemia, or lymphoma; or a solid tumor, such as, for example, sarcoma, carcinoma, melanoma, or cancer of the colon, breast, ovary, gastrointestinal system, kidney, lung (e.g., non-small-cell lung cancer and small-cell lung cancer), testicle, prostate, pancreas, lymphatic system, or bone. In certain embodiments, the pharmaceutical compositions of cytidine analogs are parenterally administered to subjects in need thereof to treat an immune disorder. In certain embodiments, the pharmaceutical compositions of cytidine analogs are parenterally administered to subjects in need thereof to treat MDS. In certain embodiments, the pharmaceutical compositions of cytidine analogs are parenterally administered to subjects in need thereof to treat AML. In certain embodiments, the pharmaceutical compositions provided herein are co-administered with one or more therapeutic agents to provide a synergistic therapeutic effect in subjects in need thereof. In certain embodiments, the pharmaceutical compositions provided herein are co-administered with one or more therapeutic agents to provide a resensitization effect in subjects in need thereof. The co-administered agents may be a cancer therapeutic agent, as described herein. In certain embodiments, the co-administered agent(s) may be dosed, e.g., orally or by injection.

In particular embodiments, provided herein is a lyophilized powder comprising 5-azacytidine and optionally one or more excipient(s), and methods of using the lyophilized powder to treat cancer, disorders related to abnormal cell proliferation, or hematologic disorders (e.g., MDS). In particular embodiments, provided herein are a liquid formulation (e.g., a solution or a suspension) prepared from a lyophilized powder comprising 5-azacytidine and methods for making and using the liquid formulation to treat cancer, disorders related to abnormal cell proliferation, or hematologic disorders (e.g., MDS). In particular embodiments, provided herein are methods of preparing the liquid formulation from the lyophilized powder comprising 5-azacytidine. In certain embodiments, the lyophilized powder or the liquid formulation optionally further comprises one or more excipient(s) such as, e.g., mannitol.

In particular embodiments, provided herein is a lyophilized powder comprising decitabine (e.g., 50 mg) and optionally one or more excipient(s), and methods of using the lyophilized powder to treat cancer, disorders related to abnormal cell proliferation, or hematologic disorders (e.g., MDS or AML). In particular embodiments, provided herein are a liquid formulation (e.g., a solution or a suspension) prepared from a lyophilized powder comprising decitabine and methods for making and using the liquid formulation to treat cancer, disorders related to abnormal cell proliferation, or hematologic disorders (e.g., MDS or AML). In particular embodiments, provided herein are methods of preparing the liquid formulation from the lyophilized powder comprising decitabine. In certain embodiments, the lyophilized powder or the liquid formulation optionally further comprises one or more excipient(s) such as, e.g., monobasic potassium phosphate (potassium dihydrogen phosphate) and/or sodium hydroxide.

In one embodiment, examples of ingredients useful in preparing certain formulations provided herein are described in, e.g., Allen et al., Ansel's Pharmaceutical Dosage Forms and Drug Delivery Systems, $9^{th}$ ed., 2010; Remington: The Science and Practice of Pharmacy, $21^{st}$ ed., 2005, both of which are incorporated herein by reference in their entireties.

Specific embodiments herein provide, inter alia, pharmaceutical compositions comprising a specific amount of 5-azacytidine, for example, a pre-packaged lyophilized powder or a liquid formulation prepared therefrom (e.g., by reconstituting with cold sterile water or a cold sterile aqueous vehicle). Specific embodiments herein provide, inter alia, pharmaceutical compositions comprising a specific amount of decitabine, for example, a pre-packaged lyophilized powder or a liquid formulation prepared therefrom (e.g., by reconstituting with cold sterile water or a cold sterile aqueous vehicle). Further embodiments provide the aforementioned compositions, which: are intended for parenteral use in patients in need thereof; further comprise an excipient selected from any excipient disclosed herein; have an amount of 5-azacytidine or decitabine of about 25 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; have an amount of 5-azacytidine or decitabine of at least about 25 mg; at least about 50 mg; at least about 75 mg, or at least about 100 mg; provide a daily dose of about 15 mg/m² following parenteral administration to a subject; provide a daily dose of about 20 mg/m² following parenteral administration to a subject; provide a daily dose of about 25 mg/m² following parenteral administration to a subject; provide a daily dose of about 30 mg/m² following parenteral administration to a subject; provide a daily dose of about 35 mg/m² following parenteral administration to a subject; provide a daily dose of about 40 mg/m² following parenteral administration to a subject; provide a daily dose of about 45 mg/m² following parenteral administration to a subject; provide a daily dose of about 50 mg/m² following parenteral administration to a subject; provide a daily dose of about 75 mg/m² following parenteral administration to a subject; provide a daily dose of about 100 mg/m² following parenteral administration to a subject; provide a daily dose of about 125 mg/m² following parenteral administration to a subject; provide a daily dose of about 150 mg/m² following parenteral administration to a subject; provide a daily dose of between about 10 mg/m² and about 100 mg/m² following parenteral administration to a subject; or provide a daily dose of between about 50 mg/m² and about 100 mg/m² following parenteral administration to a subject.

Specific embodiments herein provide a liquid pharmaceutical composition comprising 5-azacytidine intended for parenteral use, which is substantially free of impurities. Specific embodiments herein provide a liquid pharmaceutical composition comprising decitabine intended for parenteral use, which is substantially free of impurities. In one embodiment, the liquid pharmaceutical composition remains substantially free of impurities after storage for a certain time (e.g., about 12 hr, about 14 hr, about 16 hr, about 18 hr, about 20 hr, about 22 hr, about 1 day, about 2 days, about 3 days, about 4 days, about 5 days, about 6 days, about 7 days, about 14 days, or greater than 14 days). In one embodiment, the liquid pharmaceutical composition is an aqueous suspension or an aqueous solution. In one embodiment, the total amount of impurities in the composition (e.g., an aqueous suspension or aqueous solution comprising 5-azacytidine or decitabine) are less than about 15% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, or less than about 0.5% w/w, relative to the weight of the cytidine analog in the composition. In one embodiment, the total amount of impurities in the composition (e.g., an aqueous suspension or aqueous solution comprising 5-azacytidine or decitabine) are less than about 15% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, or less than about 0.5% w/w, relative to the weight of the cytidine analog in the composition, after storage for greater than about 12 hours, greater than about 14 hours, greater than about 16 hours, greater than about 18 hours, greater than about 20 hours, greater than about 22 hours, greater than about 24 hours, greater than about 36 hours, greater than about 48 hours, greater than about 60 hours, greater than about 72 hours, greater than about 4 days, greater than about 5 days, greater than about 6 days, greater than about 7 days, greater than about 8 days, greater than about 9 days, greater than about 10 days, greater than about 11 days, greater than about 12 days, greater than about 13 days, or greater than about 14 days.

In one embodiment, the pharmaceutical compositions provided herein permit accurate delivery of intended doses with minimal toxicity derived from impurities in the pharmaceutical compositions.

Specific embodiments herein provide any of the aforementioned compositions, as single unit dosage forms, e.g., a pre-packaged lyophilized powder in a vial or an aqueous suspension or solution in a vial, syringe, or I.V. bag.

Specific embodiments herein provide, inter alia, methods for treating a subject having a disease associated with abnormal cell proliferation (e.g., MDS or AML), comprising parenterally administering to the subject a pharmaceutical composition comprising a therapeutically effective amount of 5-azacytidine. Specific embodiments herein provide, inter alia, methods for treating a subject having a disease associated with abnormal cell proliferation (e.g., MDS or AML), comprising parenterally administering to the subject a pharmaceutical composition comprising a therapeutically effective amount of decitabine. Further embodiments herein provide the aforementioned methods, in which: the composition accurately delivers an intended dose to the subject; the disease is myelodysplastic syndrome; the disease is acute myelogenous leukemia; the method further comprises co-administering to the subject in need thereof an additional therapeutic agent selected from any additional therapeutic agent disclosed herein; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 6° C., below about 5° C., below about 4° C., below about 3° C., below about 2° C., below about 1° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine or decitabine is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; and/or the amount of 5-azacytidine or decitabine is at least about 25 mg, at least about 50 mg; at least about 75 mg, at least about 100 mg, or at least about 125 mg.

Specific embodiments herein provide, inter alia, pharmaceutical compositions comprising a therapeutically effective amount of 5-azacytidine, for treating a disease or disorder associated with abnormal cell proliferation (e.g., MDS or AML), wherein the compositions are prepared for parenteral administration. Specific embodiments herein provide, inter alia, pharmaceutical compositions comprising a therapeutically effective amount of decitabine, for treating a disease or disorder associated with abnormal cell proliferation (e.g., MDS or AML), wherein the compositions are prepared for parenteral administration. Further embodiments herein provide the aforementioned compositions, in which: the composition accurately delivers an intended dose to the subject; the disease is myelodysplastic syndrome; the disease is acute myelogenous leukemia; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 6° C., below about 5° C., below about 4° C., below about 3° C., below about 2° C., below about 1° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine or decitabine is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; the amount of 5-azacytidine or decitabine is at least about 25 mg, at least about 50 mg; at least about 75 mg, at least about 100 mg, or at least about 125 mg; the composition is prepared to achieve a daily dose of about 15 mg/m$^2$ following parenteral administration; the composition is prepared to achieve a daily dose of about 20 mg/m$^2$ following parenteral administration; the composition is prepared to achieve a daily dose of about 25 mg/m$^2$ following parenteral administration; the composition is prepared to achieve a daily dose of about 30 mg/m$^2$ following parenteral administration; the composition is prepared to achieve a daily dose of about 35 mg/m$^2$ following parenteral administration; the composition is prepared to achieve a daily dose of about 40 mg/m$^2$ following parenteral administration; the composition is prepared to achieve a daily dose of about 45 mg/m$^2$ following parenteral administration; the composition is prepared to achieve a daily dose of about 50 mg/m$^2$ following parenteral administration; the composition is prepared to achieve a daily dose of about 75 mg/m$^2$ following parenteral administration; the composition is prepared to achieve a daily dose of about 100 mg/m$^2$ following parenteral administration; the composition is prepared to achieve a daily dose of about 125 mg/m$^2$ following parenteral administration; the composition is prepared to achieve a daily dose of about 150 mg/m$^2$ following parenteral administration; the composition is prepared to achieve a daily dose of between about 10 mg/m$^2$ and about 100 mg/m$^2$ following parenteral administration; the composition is prepared to achieve a daily dose of between about 50 mg/m$^2$ and about 100 mg/m$^2$ following parenteral administration; the composition is prepared for parenteral administration in combination with an additional therapeutic agent selected from any additional therapeutic agent disclosed herein; the composition is prepared for treating myelodysplastic syndrome or acute myelogenous leukemia; the composition is a single unit dosage form; and/or the composition further comprises an excipient selected from any excipient disclosed herein.

Specific embodiments herein provide, inter alia, uses of 5-azacytidine for the preparation of a pharmaceutical composition for treating a disease associated with abnormal cell proliferation (e.g., MDS or AML), wherein the composition is prepared for parenteral administration, and wherein the composition is prepared from cold sterile water (e.g., having a temperature of about 0° C., about 2° C., about 4° C., about 6° C., about 8° C., or about 10° C.). Specific embodiments herein provide, inter alia, uses of decitabine for the preparation of a pharmaceutical composition for treating a disease associated with abnormal cell proliferation (e.g., MDS or AML), wherein the composition is prepared for parenteral administration, and wherein the composition is prepared from cold sterile water (e.g., having a temperature of about 0° C., about 2° C., about 4° C., about 6° C., about 8° C., or about 10° C.). Further embodiments herein provide the aforementioned uses, in which: the disease is myelodysplastic syndrome or acute myelogenous leukemia; the amount of 5-azacytidine or decitabine is selected from any amount disclosed herein; and/or the composition is prepared for immediate parenteral use or for parenteral use after storage for a certain period of time. Further embodiments provide, inter alia, methods for treating a subject having a disease or disorder provided herein by administering a pharmaceutical compositions provided herein, wherein the treatment results in improved survival of the subject.

V. BRIEF DESCRIPTION OF THE DRAWINGS

Figure 8:
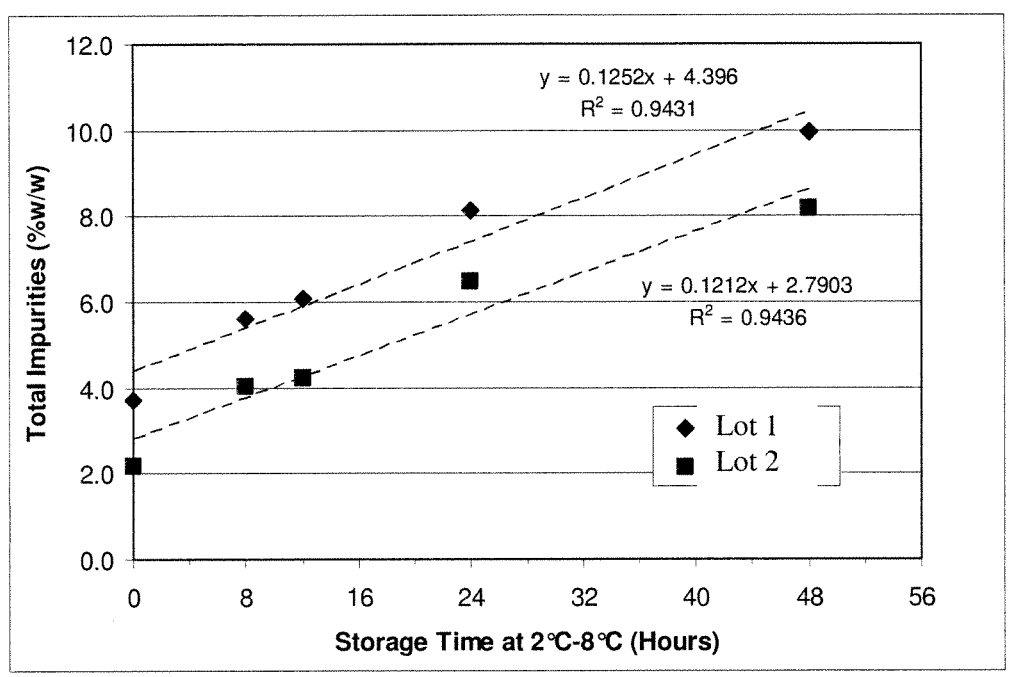

FIG. 8 represents the purity profile of 5-azacytidine suspension after reconstitution with cold WFI and followed by storage first at a temperature of about −20° C. for 24 hours and then at a temperature of between about 2° C. and about 8° C. at various time points up to about 48 hours.

VI. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

A. DEFINITIONS

As used in the specification and the accompanying claims, the indefinite articles "a" and "an" and the definite article "the" include plural as well as singular referents, unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptom(s) associated with the disease or disorder. In certain embodiments, the terms refer to minimizing the spread or worsening of the disease or disorder resulting from the administration of one or more prophylactic or therapeutic agent(s) to a subject with such a disease or disorder. In some embodiments, the terms refer to the administration of a compound or dosage form provided herein, with or without one or more additional active agent(s), after the onset of symptoms of the particular disease.

As used herein, and unless otherwise specified, the terms "prevent," "preventing" and "prevention" refer to the prevention of the onset, recurrence or spread of a disease or disorder, or of one or more symptom(s) thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease in particular are candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptom(s) thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition or dosage form refers to any lessening, whether permanent or temporary, lasting or transient, that can be attributed to or associated with the administration of the composition or dosage form.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptom(s) associated with the disease or disorder. In one embodiment, a "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. In one embodiment, a prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

"Tumor," as used herein and unless otherwise specified, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous," as used herein and unless otherwise specified, refer to or describe the physiological condition in mammals that is typically characterized by unregulated cell growth. Examples of cancer include, but are not limited to blood borne (e.g., leukemia) and solid tumors.

The terms "composition," "formulation," and "dosage form," as used herein and unless otherwise specified, are intended to encompass compositions comprising a specified ingredient(s) (in the specified amounts, if indicated), as well as any product(s) which result, directly or indirectly, from combination of the specified ingredient(s), in the specified amount(s) if indicated. By "pharmaceutical" or "pharmaceutically acceptable" it is meant that any diluent(s), additive(s), excipient(s), or carrier(s) in the composition, formulation, or dosage form are compatible with the other ingredient(s) and generally not deleterious to the recipient thereof. Unless indicated otherwise, the terms "pharmaceutical composition," "formulation," and "dosage form" are used herein interchangeably.

As used herein, and unless otherwise specified, the term "substantially free of impurities" means that the amount of impurities in a composition comprising a cytidine analog (e.g., total amount of impurities derived from the cytidine analog in the composition) is less than a certain level, for example, less than about 20% w/w, less than about 15% w/w, less than about 14% w/w, less than about 13% w/w, less than about 12% w/w, less than about 11% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, less than about 0.9% w/w, less than about 0.8% w/w, less than about 0.7% w/w, less than about 0.6% w/w, less than about 0.5% w/w, less than about 0.4% w/w, less than about 0.3% w/w, less than about 0.2% w/w, less than about 0.1% w/w, less than about 0.05% w/w, or less than about 0.01% w/w, relative to the total weight of the cytidine analog in the composition.

As used herein, and unless otherwise specified, the term "sterile," when describing a material or a composition, means that a material or a composition that is substantially free of living organisms, for example, living bacteria or other microorganisms or their spores. In specific embodiments, the term "sterile," when describing a material or a composition, refers to a material or a composition which does not comprise living organisms (e.g., bacteria or other microorganisms or their spores) and is suitable for parenteral use.

The term "subject" is defined herein to include animals such as mammals, including, but not limited to, primates (e.g., humans), cows, sheep, goats, horses, dogs, cats, rabbits, rats, mice and the like. In specific embodiments, the subject is a human. In certain embodiments, the term "subject" is used herein interchangeably with the term "patient."

As used herein, and unless otherwise specified, the terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, and unless otherwise specified, the term "isotopic composition" refers to the amount of each isotope present in a given atomic position, and "natural isotopic composition" refers to the naturally occurring isotopic composition or abundance for a given atomic position. Atomic positions containing their natural isotopic composition may also be referred to herein as "non-enriched." Unless otherwise designated, the atomic positions of the compounds recited herein are meant to represent any stable isotope of that atom. In one embodiment, unless otherwise stated, when a position is designated specifically as "H" or "hydrogen," the position is understood to have hydrogen at its natural isotopic composition.

As used herein, and unless otherwise specified, the term "isotopically enriched" refers to an atomic position having an isotopic composition other than the natural isotopic composition of that atom. "Isotopically enriched" may also refer to a compound containing at least one atomic position having an isotopic composition other than the natural isotopic composition of that atom. As used herein, an "isotopologue" is an isotopically enriched compound.

As used herein, and unless otherwise specified, the term "isotopic enrichment" refers to the percentage of incorporation of an amount of a specific isotope at a given atomic position in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

As used herein, and unless otherwise specified, the term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

With regard to the compounds provided herein, when a particular atomic position is designated as having "$^{13}C$," it is understood that the abundance of Carbon-13 at that position is substantially greater than the natural abundance of Carbon-13.

The isotopic enrichment and isotopic enrichment factor of the compounds provided herein can be determined using conventional analytical methods known to one of ordinary skill in the art, including, e.g., mass spectrometry, nuclear magnetic resonance spectroscopy, and crystallography.

B. CYTIDINE ANALOGS

1. Overview

Provided herein are dosage forms, pharmaceutical formulations and compositions comprising cytidine analogs, or salts, solvates, hydrates, precursors, or derivatives thereof. In one embodiment, the cytidine analog is 5-azacytidine. In another embodiment, the cytidine analog is 5-aza-2'-deoxycytidine (decitabine or 5-aza-CdR). In other embodiments, the cytidine analog is, for example: 1-β-D-arabinofuranosyl-cytosine (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); T-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxy-carbonyl-5'-deoxy-5-fluorocytidine (Capecitabine); $N^4$-octadecyl-cytarabine; elaidic acid cytarabine; or a conjugated compound comprising a cytidine analog and a fatty acid (e.g., a 5-azacytidine-fatty acid conjugate, including, but not limited to, CP-4200 (Clavis Pharma ASA) or a compound disclosed in WO 2009/042767, incorporated herein by reference, such as aza-C-5'-petroselinic acid ester or aza-C-5'-petrosaelaidic acid ester).

In certain embodiments, cytidine analogs provided herein include esterified derivatives of cytidine analogs, such as, e.g., esterified derivatives of 5-azacytidine. In particular embodiments, esterified derivatives are cytidine analogs that contain an ester moiety (e.g., an acetyl group) at one or more positions on the cytidine analog molecule. Esterified derivatives may be prepared by any method known in the art. In certain embodiments, esterified derivatives of a cytidine analog serve as prodrugs of the cytidine analog, such that, e.g., following administration of an esterified derivative, the derivative is deacetylated in vivo to yield the cytidine analog. A particular embodiment herein provides 2',3',5'-triacetyl-5-azacytidine (TAC), which possesses favorable physical-chemical and therapeutic properties. See, e.g., International Publication No. WO 2008/092127 (International Application No. PCT/US2008/052124); Ziemba, A. J., et al., "Development of Oral Demethylating Agents for the Treatment of Myelodysplastic Syndrome" (Abstract No. 3369), In: *Proceedings of the 100th Annual Meeting of the American Association for Cancer Research;* 2009 Apr. 18-22; Denver, Co. Philadelphia (PA): AACR; 2009 (both of which are incorporated by reference herein in their entireties).

In certain embodiments, the cytidine analogs provided herein include any compound which is structurally related to cytidine or deoxycytidine and functionally mimics and/or antagonizes the action of cytidine or deoxycytidine. Certain embodiments herein provide salts, cocrystals, solvates (e.g., hydrates), complexes, prodrugs, precursors, metabolites, and/or other derivatives of the cytidine analogs provided herein. For example, particular embodiments provide salts, cocrystals, solvates (e.g., hydrates), complexes, precursors, metabolites, and/or other derivatives of 5-azacytidine. Particular embodiments provide salts, cocrystals, solvates (e.g., hydrates), complexes, precursors, metabolites, and/or other derivatives of decitabine. Certain embodiments provide cytidine analogs that are not salts, cocrystals, solvates (e.g., hydrates), or complexes of the cytidine analogs provided herein. For example, particular embodiments provide 5-azacytidine in a non-ionized, non-solvated (e.g., anhydrous), non-complexed form. Particular embodiments provide decitabine in a non-ionized, non-solvated (e.g., anhydrous), non-complexed form. Certain embodiments herein provide mixtures of two or more cytidine analogs provided herein or derivatives thereof.

Cytidine analogs provided herein may be prepared using synthetic methods and procedures referenced herein or otherwise available in the literature. For example, particular methods for synthesizing 5-azacytidine are taught in, e.g., U.S. Pat. No. 7,038,038, U.S. Pat. No. 7,858,774, and references discussed therein, each of which is incorporated herein by reference. 5-Azacytidine is also available from Celgene Corporation, Warren, N.J. Other cytidine analogs provided herein may be prepared using previously disclosed synthetic procedures available to a person of ordinary skill in the art.

In certain embodiments, exemplary cytidine analogs have the structures provided below:

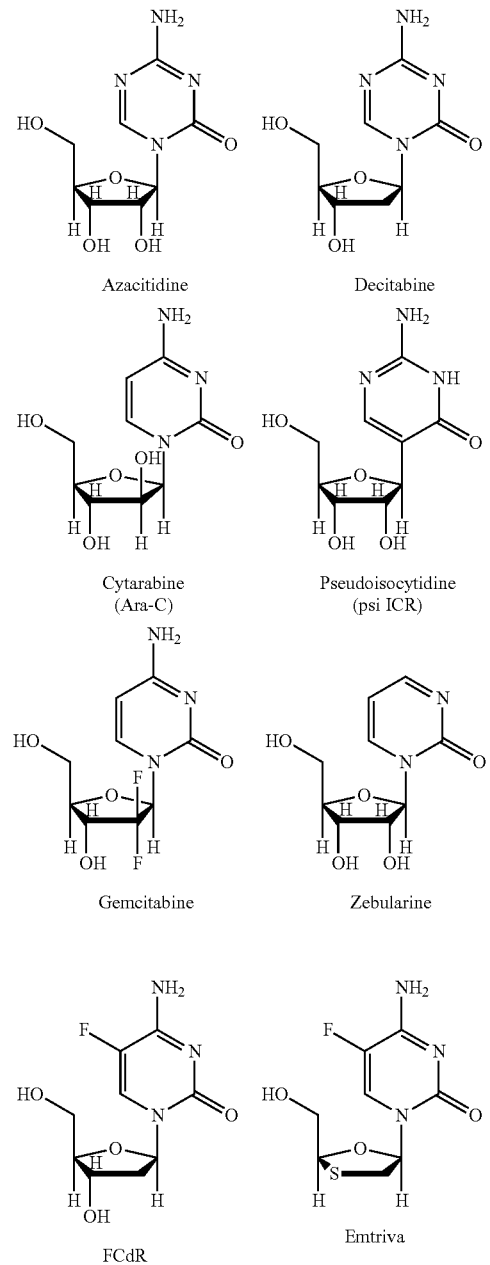

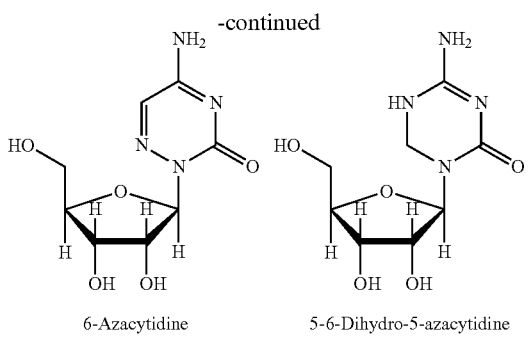

6-Azacytidine      5-6-Dihydro-5-azacytidine

2. Isotopically Enriched Cytidine Analogs

Particular embodiments herein provide isotopically enriched cytidine analogs, prodrugs thereof, synthetic intermediates thereof, and metabolites thereof. For example, specific embodiments herein provide isotopically enriched 5-azacytidine.

Isotopic enrichment (e.g., deuteration) of pharmaceuticals to improve pharmacokinetics ("PK"), pharmacodynamics ("PD"), and toxicity profiles, has been demonstrated previously with some classes of drugs. See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade, D., Chem. Biol. Interact. 117: 191 (1999).

Without being limited by any particular theory, isotopic enrichment of a drug can be used, for example, to: (1) reduce or eliminate unwanted metabolites; (2) increase the half-life of the parent drug; (3) decrease the number of doses needed to achieve a desired effect; (4) decrease the amount of a dose necessary to achieve a desired effect; (5) increase the formation of active metabolites, if any are formed; and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to an analogous kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

Certain embodiments herein provide deuterium enriched 5-azacytidine analogs, wherein one or more hydrogen(s) in the 5-azacytidine molecule is/are isotopically enriched with deuterium. In certain embodiments, provided herein are compounds of formula (I):

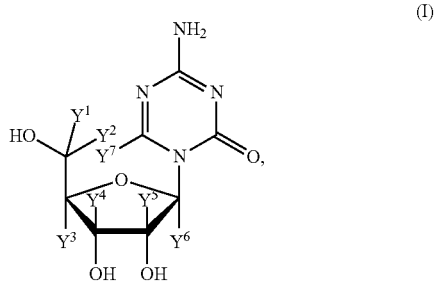

(I)

wherein one or more Y atom(s) (i.e., $Y^1$, $Y^2$, $Y^3$, $Y^4$, $Y^5$, $Y^6$, and $Y^7$) is/are hydrogen(s) isotopically enriched with deuterium, and any remaining Y atom(s) is/are non-enriched hydrogen atom(s). In particular embodiments, one, two, three, four, five, six, or seven of the indicated Y atom(s) is/are isotopically enriched with deuterium, and any remaining Y atom(s) is/are non-enriched hydrogen(s).

In certain embodiments, one or more Y atom(s) on the ribose moiety of a compound of formula (I) is/are deuterium-enriched. Particular examples include, but are not limited to, the following compounds, in which the label "D" indicates a deuterium-enriched atomic position, i.e., a sample comprising the given compound has a deuterium enrichment at the indicated position(s) above the natural abundance of deuterium:

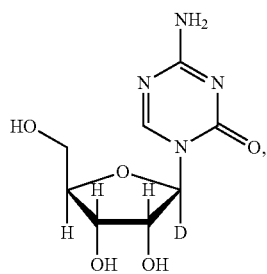
I-1

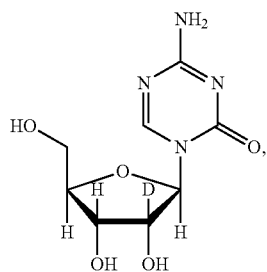
I-2

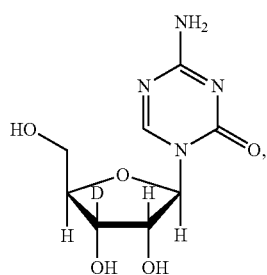
I-3

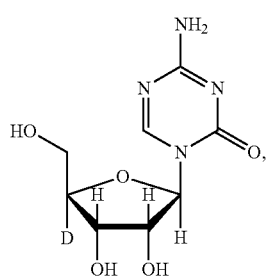
I-4

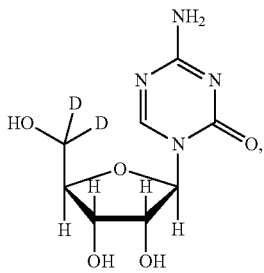
I-5

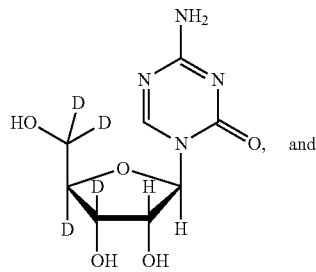
I-6
and

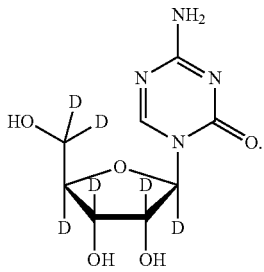
I-7

In certain embodiments, the Y atom on the 5-azacytosine moiety of a compound of formula (I) is deuterium-enriched. Particular example includes the following compound, in which the label "D" indicates a deuterium-enriched atomic position, i.e., a sample comprising the given compound has a deuterium enrichment at the indicated position above the natural abundance of deuterium:

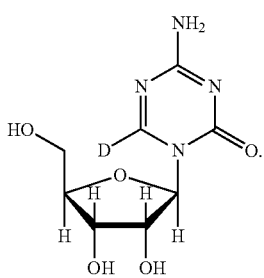
I-8

In certain embodiments, one or more Y atoms on the ribose moiety and the Y atom on the 5-azacytosine moiety of a compound of formula (I) are deuterium-enriched. Particular examples include, but are not limited to, the following compounds, in which the label "D" indicates a deuterium-enriched atomic position, i.e., a sample comprising the given compound has a deuterium enrichment at the indicated positions above the natural abundance of deuterium:

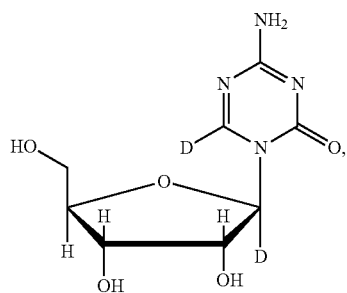

I-9

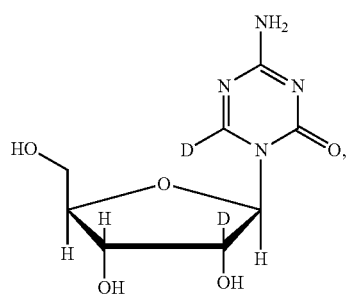

I-10

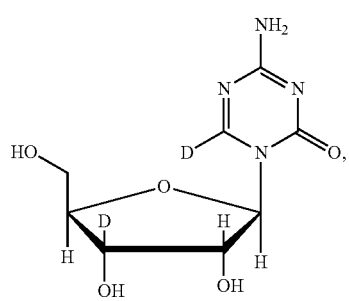

I-11

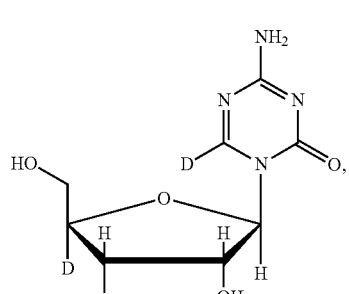

I-12

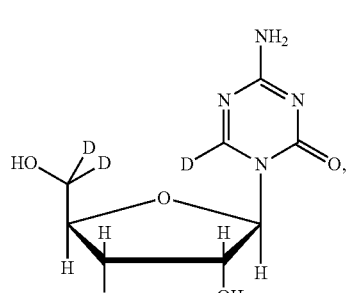

I-13

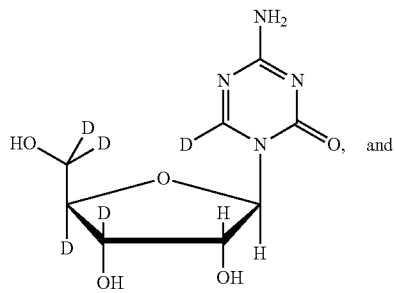

I-14

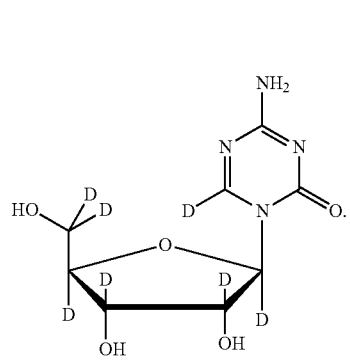

I-15

It is understood that one or more deuterium(s) may exchange with hydrogen under physiological conditions.

Certain embodiments herein provide carbon-13 enriched analogs of 5-azacytidine, wherein one or more carbon(s) in the 5-azacytidine molecule is/are isotopically enriched with carbon-13. In certain embodiments, provided herein are compounds of formula (II):

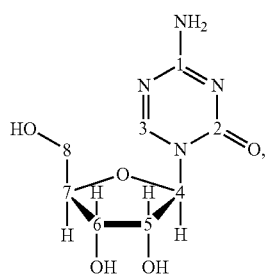

(II)

wherein one or more of 1, 2, 3, 4, 5, 6, 7, or 8 is/are carbon atom(s) isotopically enriched with carbon-13, and any remaining atom(s) of 1, 2, 3, 4, 5, 6, 7, or 8 is/are non-enriched carbon atom(s). In particular embodiments, one, two, three, four, five, six, seven, or eight carbon atom(s) (i.e., atoms 1, 2, 3, 4, 5, 6, 7, and 8) is/are isotopically enriched with carbon-13, and any remaining carbon atom(s) is/are non-enriched.

In certain embodiments, one or more carbon atom(s) of the ribose moiety of a compound of formula (II) is/are enriched with carbon-13. Particular examples include, but are not limited to, the following compounds, in which the asterisk ("*") indicates a carbon-13 enriched atomic position, i.e., a sample comprising the given compound has a carbon-13 enrichment at the indicated position(s) above the natural abundance of carbon-13:

II-1
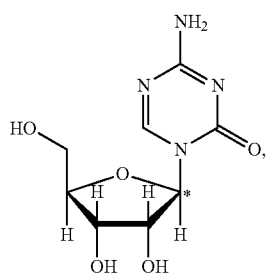

II-2
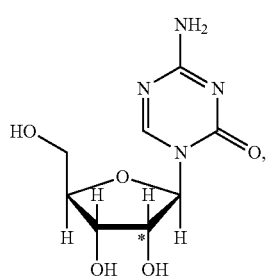

II-3
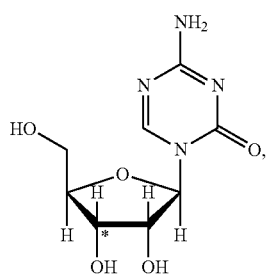

II-4
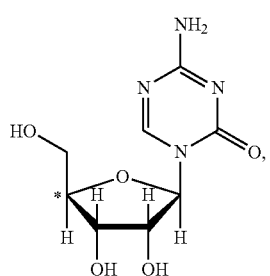

II-5
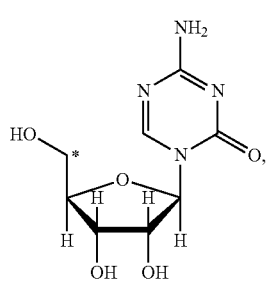

II-6
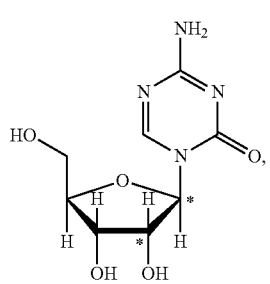

II-7
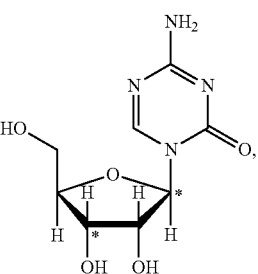

II-8
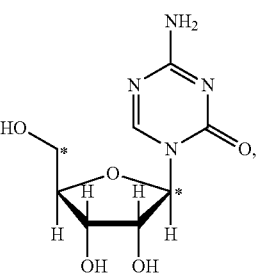

II-9
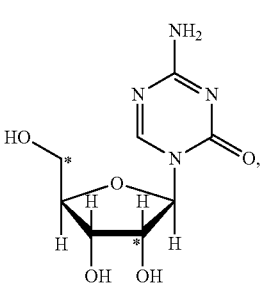

II-10
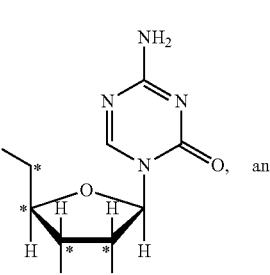
and

II-11
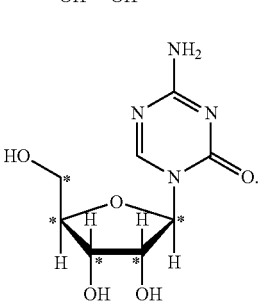
.

In certain embodiments, one or more carbon atom(s) of the 5-azacytosine moiety of a compound of formula (II) is/are enriched with carbon-13. Particular examples include, but are not limited to, the following compounds, in which the asterisk ("*") indicates a carbon-13 enriched atomic position, i.e., a sample comprising the given compound has a carbon-13 enrichment at the indicated position(s) above the natural abundance of carbon-13:

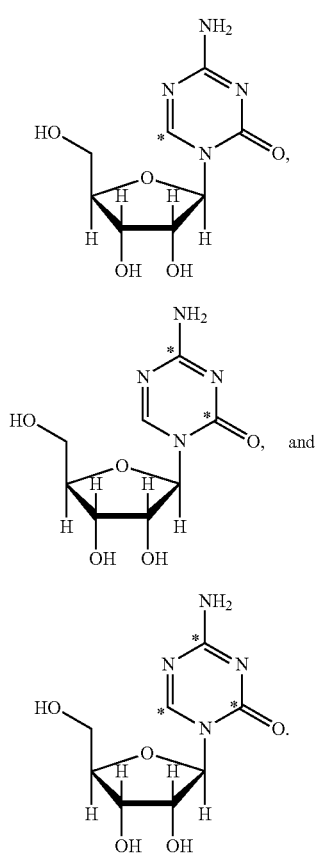

In certain embodiments, one or more carbon atoms on the ribose moiety and one or more carbon atoms on the 5-azacytosine moiety of a compound of formula (II) are enriched with carbon-13, i.e., any combination of carbon-13 enrichment for the ribose moiety and carbon-13 enrichment for the azacytosine moiety is encompassed herein.

In certain embodiments, one or more hydrogen(s) is/are enriched with deuterium(s) and one or more carbon(s) is/are enriched with carbon-13, i.e., any combination of deuterium enrichment and carbon-13 enrichment of 5-azacytidine is encompassed herein.

3. Synthesis of Isotopically Enriched Cytidine Analogs

The compounds described herein may be synthesized using any method known to one of ordinary skill in the art. For example, particular compounds described herein are synthesized using standard synthetic organic chemistry techniques known to those of ordinary skill in the art. In some embodiments, known procedures for the synthesis of 5-azacytidine are employed, wherein one or more of the reagents, starting materials, precursors, or intermediates are replaced by one or more isotopically-enriched reagents, starting materials, precursors, or intermediates, including but not limited to, one or more deuterium-enriched reagents, starting materials, precursors, or intermediates, and/or one or more carbon-13-enriched reagents, starting materials, precursors, or intermediates. Isotopically enriched reagents, starting materials, precursors, or intermediates are commercially available or may be prepared by routine chemical reactions known to one of skill in the art. In some embodiments, the routes are based on those disclosed in U.S. Pat. No. 7,038,038 and U.S. Pat. No. 7,858,774, both of which are incorporated herein by reference in their entireties.

In certain embodiments, a suitable isotopically enriched starting material, such as a deuterium-enriched ribose, a deuterium-enriched 5-azacytosine, a carbon-13-enriched ribose, and/or a carbon-13-enriched 5-azacytosine, may be employed as the starting material in the following general scheme to prepare the corresponding deuterium and/or carbon-13 enriched 5-azacytidine (See Scheme 1). Following the procedures described in U.S. Pat. No. 7,038,038 and U.S. Pat. No. 7,858,774, 5-azacytosine is treated with hexamethyldisilazane (HMDS) to render a silylated 5-azacytosine. Tetraacetyl-D-ribose is prepared by reacting D-ribose with sodium acetate in acetic anhydride, following the known procedures, such as those disclosed in Brown et al., Biochemical Preparations, 1955, 4, 70-76. The silylated 5-azacytosine is coupled to tetraacetyl-D-ribose in the presence of TMS-triflate, and the resulting protected 5-azacytidine is treated with sodium methoxide in methanol to yield 5-azacytidine. See U.S. Pat. No. 7,038,038 and U.S. Pat. No. 7,858,774.

Scheme 1

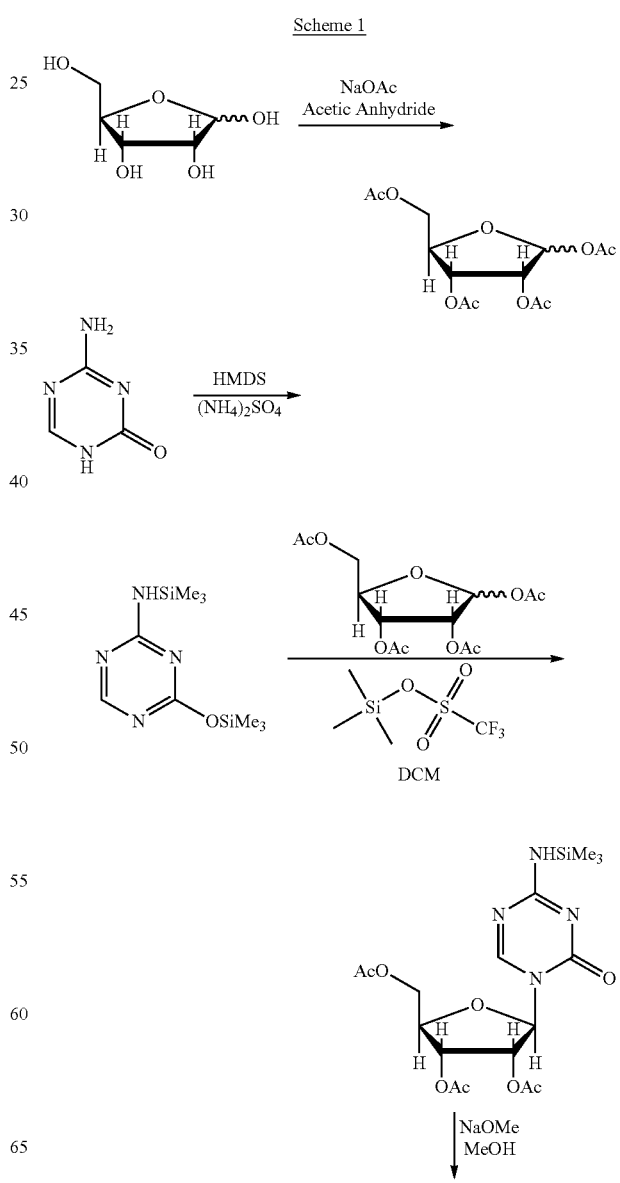

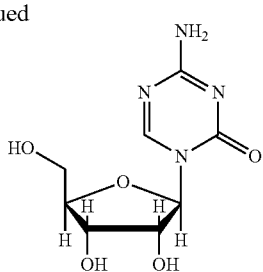

In some embodiments, one or more hydrogen position(s) in the ribose portion of 5-azacytidine is/are enriched with deuterium. Such 5-azacytidine analogs may be prepared following Scheme 1 from a suitable deuterium-enriched ribose, purchased from a commercial source or prepared following literature procedures. Specific examples of deuterium-enriched ribose starting material include, but are not limited to, the following compounds listed in Table 1, which may be converted to the corresponding deuterium-enriched 5-azacytidine analogs.

TABLE 1

| Starting Material | Structure | Source/Reference | 5-Azacytidine Product |
|---|---|---|---|
| D-Ribose-1-D | 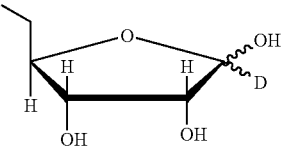 | Cambridge Isotope Lab. | I-1 |
| D-Ribose-2-D | 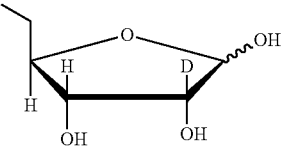 | Cambridge Isotope Lab. | I-2 |
| D-Ribose-3-D | 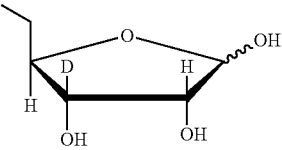 | Omicron Biochemicals, Inc. | I-3 |
| D-Ribose-4-D | 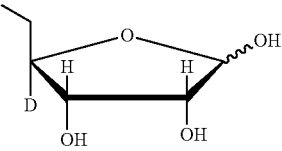 | Omicron Biochemicals, Inc. | I-4 |
| D-Ribose-5,5'-D$_2$ | 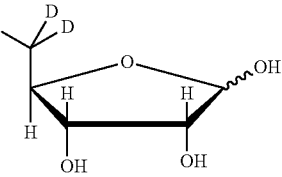 | Omicron Biochemicals, Inc. | I-5 |
| D-Ribose-3,4,5,5'-D$_4$ | 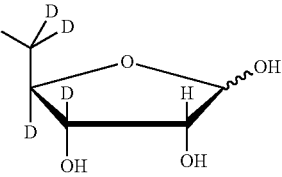 | Prepared following the procedures in J. Am. Chem. Soc. 1996, 118, 7929-7940. | I-6 |

In other embodiments, the hydrogen position on the 5-azacytosine ring of 5-azacytidine is enriched with deuterium. Such 5-azacytidine analog may be prepared, e.g., from deuterated 5-azacytosine following Scheme 1. The deuterated 5-azacytosine may be prepared, e.g., from suitable deuterated reagents as shown in Scheme 2. See e.g., Grundmann et al., Chem. Ber. 1954, 87, 19-24; Piskala et al., in Zorbach and Tipson (eds.) Synthetic Procedures in Nucleic Acid Chemistry, Vol. 1, Wiley Interscience, New York, 1968, 107-08; Piskala, Collect. Czech. Chem. Comm. 1967, 32, 3966-76.

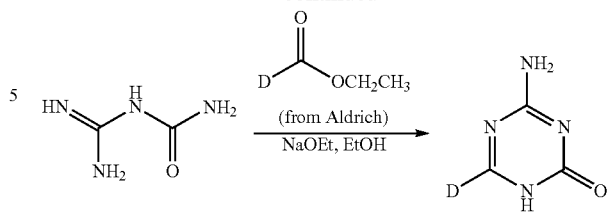

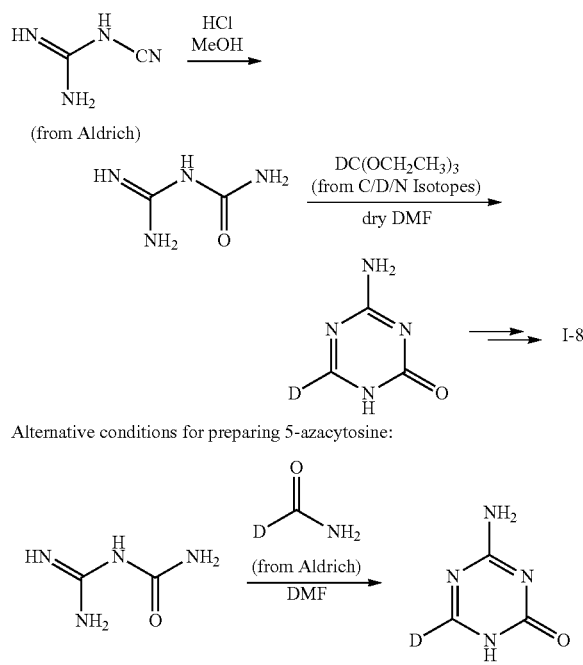

In other embodiments, both the hydrogen position on the 5-azacytosine ring and one or more hydrogen position(s) in the ribose portion of 5-azacytidine are enriched with deuterium. Such 5-azacytidine analogs may be prepared, e.g., following Scheme 1, coupling a suitable deuterated ribose starting materials with deuterated 5-azacytosine. For example, compounds I-9, I-10, I-11, I-12, I-13, and I-14 may be prepared from the corresponding deuterated ribose starting material listed in Table 1, and deuterated 5-azacytosine prepared according to Scheme 2.

In some embodiments, one or more carbon atom(s) in the ribose portion of 5-azacytidine is/are enriched with carbon-13. Such 5-azacytidine analogs may be prepared following Scheme 1 from a suitable carbon-13-enriched ribose, purchased from a commercial source or prepared following literature procedures. Specific examples of carbon-13-enriched ribose starting material include, but are not limited to, the following compounds listed in Table 2, which may be converted to the corresponding carbon-13-enriched 5-azacytidine analogs. (The asterisk "*" indicates a carbon-13 enriched atomic position)

TABLE 2

| Starting Material | Structure | Source/Reference | 5-Azacytidine Product |
|---|---|---|---|
| D-Ribose-1-$^{13}$C | 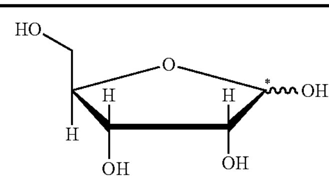 | Sigma Aldrich | II-1 |
| D-Ribose-2-$^{13}$C | 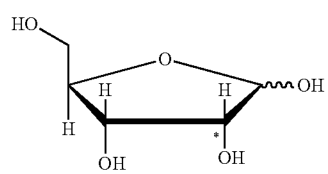 | Sigma Aldrich | II-2 |
| D-Ribose-3-$^{13}$C | 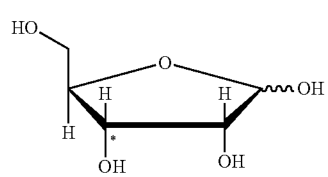 | Omicron Biochemicals, Inc. | II-3 |

TABLE 2-continued

| Starting Material | Structure | Source/Reference | 5-Azacytidine Product |
|---|---|---|---|
| D-Ribose-4-$^{13}$C | 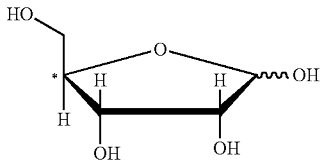 | Omicron Biochemicals, Inc. | II-4 |
| D-Ribose-5-$^{13}$C | 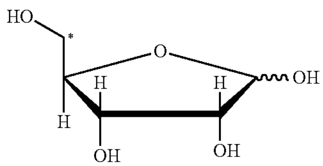 | Cambridge Isotope Lab. | II-5 |
| D-Ribose-1,2-$^{13}$C$_2$ | 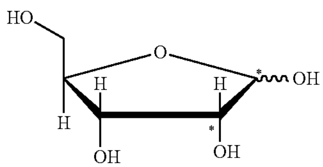 | Sigma Aldrich | II-6 |
| D-Ribose-1,3-$^{13}$C$_2$ | 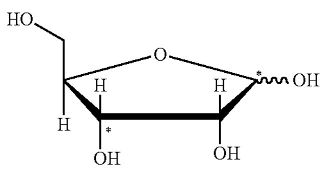 | Omicron Biochemicals, Inc. | II-7 |
| D-Ribose-1,5-$^{13}$C$_2$ | 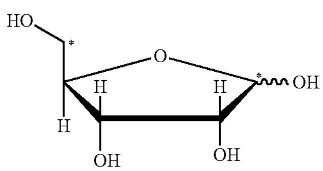 | Omicron Biochemicals, Inc. | II-8 |
| D-Ribose-2,5-$^{13}$C$_2$ | 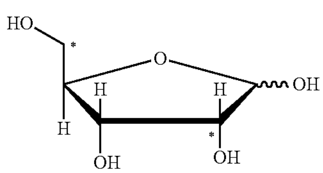 | Omicron Biochemicals, Inc. | II-9 |
| D-Ribose-2,3,4,5-$^{13}$C$_4$ | 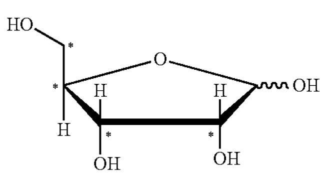 | Sigma Aldrich | II-10 |
| D-Ribose-1,2,3,4,5-$^{13}$C$_5$ | 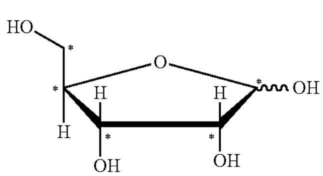 | Cambridge Isotope Lab. | II-11 |

In other embodiments, one or more carbon atom(s) in the 5-azacytosine ring is/are enriched with carbon-13. Such 5-azacytidine analogs may be prepared from a carbon-13-enriched 5-azacytosine following Scheme 1. The carbon-13 enriched 5-azacytosine intermediates may be prepared from suitable carbon-13 enriched reagents as shown in Scheme 3. See e.g., Grundmann et al., Chem. Ber. 1954, 87, 19-24; Piskala et al., in Zorbach and Tipson (eds.) Synthetic Procedures in Nucleic Acid Chemistry, Vol. 1, Wiley Interscience, New York, 1968, 107-08; Piskala, Collect. Czech. Chem. Comm. 1967, 32, 3966-76.

Scheme 3

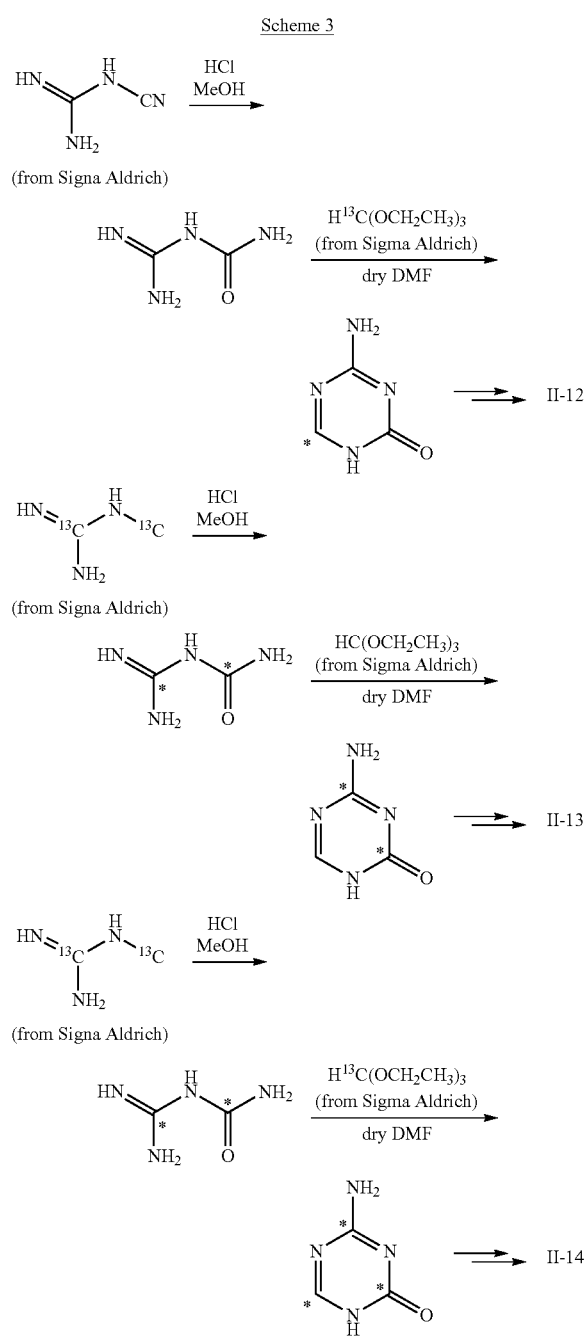

In other embodiments, one or more carbon position(s) on the 5-azacytosine ring and one or more carbon position(s) in the ribose portion of 5-azacytidine are enriched with carbon-13. Such 5-azacytidine analogs may be prepared following Scheme 1, coupling a suitable carbon-13-enriched ribose starting materials with a suitable carbon-13-enriched 5-azacytosine. For example, compounds may be prepared from a carbon-13-enriched ribose starting material listed in Table 2, and a carbon-13-enriched 5-azacytosine prepared according to Scheme 3.

The routes and methods described above may be modified to provide an isotopologue of 5-azacytidine having both deuterium enrichment and carbon-13 enrichment.

C. PHARMACEUTICAL COMPOSITIONS

Embodiments herein encompass pharmaceutical compositions or dosage forms comprising one or more cytidine analog(s), such as, e.g., 5-azacytidine or decitabine, or a salt, solvate, hydrate, precursor, or derivative thereof. In certain embodiments, the pharmaceutical compositions or dosage forms optionally further comprise one or more excipient(s), such as, e.g., mannitol or other excipient provided herein. In one embodiment, the pharmaceutical compositions or dosage forms are prepared for parenteral administration, e.g., subcutaneous or intravenous administration. Also provided herein are methods of preparing the pharmaceutical compositions or dosage forms. Also provided herein are methods of using the pharmaceutical compositions or dosage forms to treat diseases and disorders, including cancer, disorders related to abnormal cell proliferation, and hematologic disorders (e.g., MDS or AML), among others.

In particular embodiments, provided herein is a lyophilized powder comprising 5-azacytidine and optionally one or more excipient(s), and methods of using the lyophilized powder to treat cancer, disorders related to abnormal cell proliferation, or hematologic disorders (e.g., MDS). In particular embodiments, provided herein is a lyophilized powder comprising decitabine and optionally one or more excipient(s), and methods of using the lyophilized powder to treat cancer, disorders related to abnormal cell proliferation, or hematologic disorders (e.g., MDS). In particular embodiments, provided herein are a liquid formulation (e.g., a solution or a suspension) prepared from a lyophilized powder comprising 5-azacytidine, and methods for making and using the liquid formulation to treat cancer, disorders related to abnormal cell proliferation, or hematologic disorders (e.g., MDS). In particular embodiments, provided herein are a liquid formulation (e.g., a solution or a suspension) prepared from a lyophilized powder comprising decitabine, and methods for making and using the liquid formulation to treat cancer, disorders related to abnormal cell proliferation, or hematologic disorders (e.g., MDS). In particular embodiments, provided herein are methods of preparing the liquid formulation from the lyophilized powder comprising 5-azacytidine. In particular embodiments, provided herein are methods of preparing the liquid formulation from the lyophilized powder comprising decitabine. In certain embodiments, the lyophilized powder or the liquid formulation optionally further comprises one or more excipient(s) such as, e.g., mannitol or other excipient provided herein.

In one embodiment, the pharmaceutical compositions provided herein permit accurate delivery of intended doses with minimal toxicity derived from impurities in the pharmaceutical compositions.

1. Pharmaceutical Compositions

In one embodiment, provided herein is a pharmaceutical composition comprising a cytidine analog, such as, e.g., 5-azacytidine or decitabine, or a salt, solvate, hydrate, precursor, or derivative thereof. In one embodiment, the pharmaceutical composition is useful for parenteral administration of a cytidine analog.

In one embodiment, the pharmaceutical composition provided herein is a solid composition (e.g., a lyophilized powder), which may be reconstituted with water, or with a liquid vehicle as provided herein elsewhere, to render a liquid dosage form (e.g., a suspension or a solution) suitable for parenteral use. In one embodiment, the water or liquid vehicle used in reconstitution of the solid composition is cold or pre-cooled (e.g., having a temperature of less than about 10° C., less than about 8° C., less than about 6° C., less than about 4° C., less than about 2° C., or less than about 1° C.). In one embodiment, the solid composition and the water or liquid vehicle used in reconstitution of the solid composition are sterile (e.g., pyrogen-free). In one embodiment, the pharmaceutical composition provided herein is a liquid composition comprising a cytidine analog (e.g., a suspension, a solution, or an emulsion), which is substantially free of impurities. In certain embodiments, such liquid composition is suitable for parenteral administration, facilitates the accurate delivery of an intended dose of a cytidine analog (e.g., 5-azacytidine or decitabine), and minimizes any undesired toxicity derived from impurities. In one embodiment, the pharmaceutical composition provided herein (e.g., a liquid composition comprising a cytidine analog) is stored for a certain period of time (e.g., up to 1 day, up to 2 days, up to 3 days, up to 7 days, up to 14 days, or greater than 14 days) and is substantially free of impurities after such storage. In certain embodiments, the pharmaceutical composition may be stored refrigerated (e.g., at a temperature of between about 2° C. and about 8° C.) or frozen (e.g., at a temperature of about −20° C.) prior to use.

In one embodiment, provided herein is a solid pharmaceutical composition (e.g., a lyophilized powder), comprising a cytidine analog (e.g., 5-azacytidine or decitabine). In one embodiment, provided herein is a liquid pharmaceutical composition, e.g., a solution or a suspension, comprising a cytidine analog (e.g., 5-azacytidine or decitabine). In one embodiment, the solid or liquid composition further comprises one or more excipient(s) provided herein, such as, e.g., mannitol or other excipient provided herein. In one embodiment, the solid pharmaceutical composition provided herein is reconstituted with water to provide a solution or a suspension. In one embodiment, the solid pharmaceutical composition provided herein is reconstituted with an aqueous vehicle to provide a solution or a suspension. In one embodiment, the water or aqueous vehicle is sterile and pre-cooled to a certain temperature before being mixed with the solid composition. In one embodiment, the sterile water or sterile aqueous vehicle is pre-cooled to a temperature of about 10° C., about 8° C., about 6° C., about 5° C., about 4° C., about 3° C., about 2° C., about 1° C., or about 0° C., before being mixed with the solid composition. In certain embodiments, mixing a solid pharmaceutical composition provided herein (e.g., a sterile lyophilized powder comprising a cytidine analog, e.g., 5-azacytidine or decitabine) with cold sterile water (e.g., sterile water at a temperature of about 10° C., about 8° C., about 6° C., about 5° C., about 4° C., about 3° C., about 2° C., about 1° C., or about 0° C.) provides a liquid dosage form (e.g., a sterile suspension or a sterile solution comprising a cytidine analog, e.g., 5-azacytidine or decitabine), which is substantially free of impurities.

In one embodiment, the pharmaceutical composition provided herein further comprises one or more excipient(s). In certain embodiments, selection of excipients and amounts to use may be readily determined by the formulation scientist based upon experience and consideration of standard procedures and reference works available in the art. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In one particular embodiment, provided herein is a liquid dosage form (e.g., a suspension or a solution), which is prepared from a solid pharmaceutical composition comprising a cytidine analog (e.g., a sterile lyophilized powder comprising 5-azacytidine or decitabine, and optionally one or more excipient(s), such as, e.g., mannitol), wherein the solid pharmaceutical composition is reconstituted with cold sterile water or a cold sterile vehicle to render the liquid dosage form comprising the cytidine analog (e.g., 5-azacytidine or decitabine) for parenteral use. In certain embodiments, the liquid composition comprising the cytidine analog (e.g., 5-azacytidine or decitabine) may be stored at a temperature of below about 10° C. (e.g., refrigerated or frozen at a temperature of about 8° C., about 6° C., about 4° C., about 2° C., about 0° C., about −5° C., about −10° C., about −15° C., about −20° C., between about 2° C. and about 8° C., or below about −20° C.) for a period of about 1 day, about 2 days, about 3 days, about 4 days, about 5 days, about 6 days, about 7 days, about 14 days, up to about 7 days, up to about 14 days, or greater than about 14 days, before parenteral administration to a subject in need thereof. In certain embodiments, the liquid composition prepared from cold sterile water or a cold sterile aqueous vehicle is warmed to about room temperature before parenteral administration to a subject in need thereof. In certain embodiments, the liquid composition comprising the cytidine analog (e.g., 5-azacytidine or decitabine) which is stored at a temperature below about 10° C. is warmed to about room temperature before parenteral administration to a patient. In specific embodiments, the total amount of impurities in the liquid composition comprising the cytidine analog (e.g., 5-azacytidine or decitabine) is less than about 25% w/w, less than about 20% w/w, less than about 15% w/w, less than about 14% w/w, less than about 13% w/w, less than about 12% w/w, less than about 11% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, less than about 0.5% w/w, or less than about 0.1% w/w, before or after storage.

In specific embodiments, the cytidine analogs, e.g., 5-azacytidine or decitabine, and the pharmaceutical formulations and compositions comprising the cytidine analogs provided herein are used for treating diseases and disorders associated with abnormal cell proliferation (e.g., MDS or AML). In one embodiment, the formulations and compositions are prepared for parenteral administration and may be used for the accurate delivery of an intended dose of a cytidine analog to a patient in need thereof.

Particular embodiments relate to the use of one or more cytidine analogs, e.g., 5-azacytidine or decitabine, for the preparation of pharmaceutical formulations and compositions for treating particular medical indications, as provided herein. The pharmaceutical formulations and compositions comprising cytidine analogs provided herein are intended for parenteral delivery of the cytidine analog in subjects in need thereof. Parenteral delivery includes, but is not limited to, subcutaneous delivery, intravenous delivery, intramuscular delivery, intradermal delivery, and the like. In other embodiments, parenteral delivery includes, but is not limited to, intra-articular delivery, intrasynovial delivery, intraspinal delivery, intrathecal delivery, intra-arterial delivery, and intracardiac delivery. In one embodiment, the pharmaceutical formulation and compositions are prepared to be sterile (i.e., pyrogen-free or free from contaminating microorganisms) and may comprise one or more excipient(s) provided herein elsewhere.

Particular embodiments herein provide solid dosage forms that are a lyophilized powder comprising a cytidine analog, such as, e.g., 5-azacytidine or decitabine. In one embodiment, the lyophilized powder further comprises one or more excipient(s), such as, those known to one of skill in the art or provided herein elsewhere. In particular embodiments, the lyophilized powder further comprises mannitol. In certain embodiments, the lyophilized powder is reconstituted with cold sterile water or a cold sterile aqueous vehicle to render a liquid dosage form comprising the cytidine analog. In certain embodiments, the liquid dosage form is an aqueous suspension. In certain embodiments, the liquid dosage form is an aqueous solution. In certain embodiments, the solid or liquid dosage forms provided herein optionally comprise one or more excipient(s) or additive(s) as described herein elsewhere. In certain embodiments, embodiments herein encompass the use of cytidine analogs, e.g., 5-azacytidine or decitabine, for the preparation of a pharmaceutical composition for treating a disease associated with abnormal cell proliferation, wherein the composition is prepared for parenteral administration.

In particular embodiments, formulations provided herein (e.g., a solid formulation or a liquid formulation) comprise a cytidine analog, such as, for example, 5-azacytidine or decitabine, in a specific amount. In particular embodiments, the specific amount of the cytidine analog in the formulation is, e.g., about 10 mg, about 20 mg, about 40 mg, about 60 mg, about 80 mg, about 100 mg, about 120 mg, about 140 mg, about 160 mg, about 180 mg, about 200 mg, about 220 mg, least about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, about 4000 mg, or about 5000 mg. In particular embodiments, the specific amount of the cytidine analog in the formulation is, e.g., at least about 10 mg, at least about 20 mg, at least about 40 mg, at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, at least about 1500 mg, at least about 1600 mg, at least about 1700 mg, at least about 1800 mg, at least about 1900 mg, at least about 2000 mg, at least about 2100 mg, at least about 2200 mg, at least about 2300 mg, at least about 2400 mg, at least about 2500 mg, at least about 3000 mg, at least about 4000 mg, or at least about 5000 mg.

Certain embodiments herein provide pharmaceutical compositions that are single unit dosage forms comprising a cytidine analog (e.g., 5-azacytidine or decitabine). In one embodiment, provided herein is a pre-packaged sterile lyophilized powder comprising a certain amount of a cytidine analog (e.g., about 100 mg of 5-azacytidine or about 50 mg of decitabine). In one embodiment, the single unit dosage forms optionally further comprise one or more excipient(s), such as, e.g., mannitol, potassium dihydrogen phosphate, and/or sodium hydroxide. In one embodiment, provided herein is a pre-packaged sterile lyophilized powder comprising about 100 mg of 5-azacytidine, and optionally further comprising one or more excipient(s), such as, e.g., mannitol. In one embodiment, provided herein is a pre-packaged sterile lyophilized powder comprising about 100 mg of 5-azacytidine and about 100 mg of mannitol. In one embodiment, provided herein is a pre-packaged sterile lyophilized powder comprising about 50 mg of decitabine, and optionally further comprising one or more excipient(s), such as, e.g., potassium dihydrogen phosphate and/or sodium hydroxide. In one embodiment, provided herein is a pre-packaged sterile lyophilized powder comprising about 50 mg of decitabine, about 68 mg of potassium dihydrogen phosphate, and about 12 mg of sodium hydroxide. In certain embodiments, the pre-packaged sterile lyophilized powder is reconstituted with cold sterile water or a cold sterile aqueous vehicle to yield a liquid dosage form (e.g., a suspension or a solution) for parenteral administration in a subject in need thereof (e.g., subcutaneous or intravenous administration). When intravenous administration is contemplated, the reconstituted liquid dosage form may be further diluted with sterile water or a sterile aqueous vehicle to form a solution. In one embodiment, the water or aqueous vehicle is pre-cooled to a certain temperature before being mixed with the lyophilized powder. In one embodiment, the water or aqueous vehicle is pre-cooled to a temperature of about 10° C., about 8° C., about 6° C., about 5° C., about 4° C., about 3° C., about 2° C., about 1° C., or about 0° C., before being mixed with the lyophilized powder. In one embodiment, the lyophilized powder is packaged in a single-use vial (i.e., unused portions of each vial are discarded and not saved for later administration). In some embodiments, the content(s) of one or more vial(s) may be reconstituted and combined to deliver an intended dose of the cytidine analog (e.g., 5-azacytidine or decitabine) to a subject in need thereof.

Specific embodiments herein provide, inter alia, pharmaceutical compositions comprising a specific amount of 5-azacytidine, for example, a pre-packaged lyophilized powder or a liquid formulation prepared therefrom (e.g., by reconstituting with cold sterile water or a cold sterile aqueous vehicle). Specific embodiments herein provide, inter alia, pharmaceutical compositions comprising a specific amount of decitabine, for example, a pre-packaged lyophilized powder or a liquid formulation prepared therefrom (e.g., by reconstituting with cold sterile water or a cold sterile aqueous vehicle). Further embodiments provide the aforementioned compositions, which: are intended for parenteral use in patients in need thereof; further comprise an excipient selected from any excipient disclosed herein; have an amount of 5-azacytidine or decitabine of about 25 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; have an amount of 5-azacytidine or decitabine of at least about 50 mg; at least about 75 mg, or at least about 100 mg; provide a daily dose of about 30 mg/m$^2$ following parenteral administration to a subject; provide a daily dose of about 40 mg/m$^2$ following parenteral administration to a subject; provide a daily dose of about 50 mg/m$^2$ following parenteral administration to a subject; provide a daily dose of about 75 mg/m$^2$ following parenteral administration to a subject; provide a daily dose of about 100 mg/m$^2$ following parenteral administration to a subject; provide a daily dose of about 125 mg/m$^2$ following parenteral administration to a subject; provide a daily dose of about 150 mg/m$^2$ following parenteral administration to a subject; or provide a daily dose of between about 50 mg/m$^2$ and about 100 mg/m$^2$ following parenteral administration to a subject.

Specific embodiments herein provide a liquid pharmaceutical composition comprising 5-azacytidine intended for parenteral use, which is substantially free of impurities. Specific embodiments herein provide a liquid pharmaceutical composition comprising decitabine intended for parenteral use, which is substantially free of impurities. In one embodiment, the liquid pharmaceutical composition remains substantially free of impurities after storage for a certain time (e.g., about 12 hours, about 1 day, about 2 days, about 3 days, about 5 days, about 7 days, about 14 days, or greater than 14 days). In one embodiment, the liquid pharmaceutical composition is an aqueous suspension or an aqueous solution. In one embodiment, the total amount of impurities in the composition (e.g., an aqueous suspension or aqueous solution comprising 5-azacytidine or decitabine) are less than about 15% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, or less than about 0.5% w/w, relative to the weight of the cytidine analog in the composition. In one embodiment, the total amount of impurities in the composition (e.g., an aqueous suspension or aqueous solution comprising 5-azacytidine or decitabine) are less than about 15% w/w, less than about 10% w/w, less than about 9% w/w, less than about 8% w/w, less than about 7% w/w, less than about 6% w/w, less than about 5% w/w, less than about 4% w/w, less than about 3% w/w, less than about 2% w/w, less than about 1% w/w, or less than about 0.5% w/w, relative to the weight of the cytidine analog in the composition, after storage for greater than about 12 hours, greater than about 24 hours, greater than about 36 hours, greater than about 48 hours, greater than about 60 hours, greater than about 72 hours, greater than about 4 days, greater than about 5 days, greater than about 6 days, greater than about 7 days, greater than about 8 days, greater than about 9 days, greater than about 10 days, greater than about 11 days, greater than about 12 days, greater than about 13 days, or greater than about 14 days.

In certain embodiments, the compositions provided herein comprising a cytidine analog, e.g., 5-azacytidine or decitabine, are essentially free of a cytidine deaminase inhibitor (e.g., do not comprise a cytidine deaminase inhibitor). In certain embodiments, the compositions provided herein are essentially free of (e.g., do not comprise) the cytidine deaminase inhibitor tetrahydrouridine (THU). Certain embodiments herein provide pharmaceutical compositions comprising a therapeutically effective amount of a cytidine analog (e.g., 5-azacytidine or decitabine), wherein the compositions are essentially free of (e.g., do not comprise) a cytidine deaminase inhibitor (e.g., THU). In particular embodiments, a composition provided herein that is essentially free of a cytidine deaminase inhibitor (e.g., THU) comprises, e.g., less than 200 mg, less than 150 mg, less than 100 mg, less than 50 mg, less than 25 mg, less than 10 mg, less than 5 mg, less than 1 mg, or less than 0.1 mg of the cytidine deaminase inhibitor.

Further provided herein are kits comprising a solid dosage form of a cytidine analog, which may be reconstituted to generate a liquid dosage form of the cytidine analog suitable for parenteral use. Further provided are articles of manufacture containing packaging material, a formulation of a cytidine analog, and a label that indicates the method of using the formulation (e.g., methods of reconstituting the formulation comprising the cytidine analog, and methods of use) for the treatment of certain diseases or disorders including, e.g., a cancer, a disorder related to abnormal cell proliferation, a hematologic disorder, or an immune disorder.

In particular embodiments, provided herein is a lyophilized formulation of 5-azacytidine, wherein the 5-azacytidine is packaged in a sealed glass vial. In particular embodiments, provided herein is a sterile lyophilized formulation of 5-azacytidine, wherein the 5-azacytidine is packaged in a sealed glass vial. In one embodiment, the glass vial contains about 100 mg of 5-azacytidine. In one embodiment, the glass vial contains about 100 mg of 5-azacytidine and about 100 mg of mannitol. In one embodiment, the sealed glass vial is a 30 cc Type I glass vial with a 20 mm neck finish. In one embodiment, the sealed glass vial has a elastomeric enclosure. In one embodiment, provided herein is a lyophilized powder comprising about 100 mg of 5-azacytidine and about 100 mg of mannitol. In one embodiment, provided herein is a lyophilized powder consisting essentially of about 100 mg of 5-azacytidine and about 100 mg of mannitol. In certain embodiments, the lyophilized powder comprising 5-azacytidine may be stored for at least about 48 months without significant degradation of 5-azacytidine or decrease in potency of the drug product after storage. In certain embodiments, a primary degradation product (e.g., N-formylguanylribosylurea) is converted to a secondary degradation product (e.g., guanylribosylurea) over time, and there is no net increase in total degradation products upon storage.

2. Methods of Preparation

Provided herein are methods of making the pharmaceutical compositions provided herein comprising a cytidine analog. Certain embodiments herein provide methods of preparing pharmaceutical compositions of cytidine analogs (e.g., 5-azacytidine or decitabine) intended for parenteral delivery. In specific embodiments, provided herein is a method of preparing a liquid dosage form of 5-azacytidine using cold sterile water or a cold sterile aqueous vehicle. In specific embodiments, provided herein is a method of preparing a liquid dosage form of decitabine using cold sterile water or a cold sterile aqueous vehicle. In one embodiment, provided herein is a method of preparing a liquid dosage form of 5-azacytidine comprising the step of reconstituting (i.e., mixing) a sterile lyophilized powder comprising 5-azacytidine and optionally one or more excipient(s) (e.g., mannitol) with cold sterile water or a cold sterile aqueous vehicle. In one embodiment, provided herein is a method of preparing a liquid dosage form of decitabine comprising the step of reconstituting (i.e., mixing) a sterile lyophilized powder comprising decitabine and optionally one or more excipient(s) with cold sterile water or a cold sterile aqueous vehicle.

In one embodiment, the volume of cold sterile water or a cold sterile aqueous vehicle used for reconstitution is about 1 mL, about 2 mL, about 3 mL, about 4 mL, about 5 mL, about 6 mL, about 7 mL, about 8 mL, about 9 mL, about 10 mL, about 12 mL, about 14 mL, about 15 mL, about 16 mL, about 18 mL, about 20 mL, about 25 mL, about 30 mL, about 40 mL, about 50 mL, about 60 mL, about 70 mL, about 80 mL, about 90 mL, about 100 mL, about 150 mL, or about 200 mL. In one embodiment, the water used for reconstitution is Water for Injection (WFI). In one embodiment, the Water for Injection used for reconstitution is sterile.

In one embodiment, provided herein are methods of preparing a liquid composition comprising a cytidine analog (e.g., a suspension or a solution), which is substantially free of impurities. In certain embodiments, such method comprises reconstituting or mixing a solid composition provided herein (e.g., a lyophilized powder) comprising a cytidine analog (e.g., 5-azacytidine or decitabine) with cold water or a cold aqueous vehicle (e.g., having a temperature of less than about 10° C., less than about 8° C., less than about 6° C., less than about 4° C., less than about 2° C., or less than about 1° C.) to yield a liquid composition.

In one embodiment, the solid pharmaceutical compositions provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, provided herein is a method of preparing a lyophilized powder comprising 5-azacytidine, comprising one or more of the steps of: (i) dissolving 5-azacytidine and optionally one or more excipient(s) (e.g., mannitol); (ii) sterilizing the solution by filtration; (iii) aseptically filling a vial with the sterilized solution; and (iv) lyophilizing the content of the vial. In one embodiment, the production operations are performed at reduced temperature with defined time limits to minimize the formation of degradation products during manufacturing.

In one embodiment, the liquid pharmaceutical compositions provided herein may be prepared from a solid pharmaceutical compositions provided herein, wherein the solid composition is reconstituted with cold water or a cold liquid vehicle to provide the liquid composition.

In certain embodiments, the solid pharmaceutical composition is a lyophilized powder comprising a cytidine analog, wherein the powder is manufactured using standard, art-recognized processing procedures and equipment. In certain embodiments, the solid pharmaceutical composition is a sterile lyophilized powder comprising a cytidine analog, wherein the powder is manufactured using standard, art-recognized processing procedures and equipment, for example, procedures for sterilization.

In particular embodiments, provided herein is a method of preparing a liquid dosage form comprising 5-azacytidine, which is substantially free of impurities. In one embodiment, the method comprises reconstituting a sterile lyophilized powder comprising 5-azacytidine with cold sterile water. In particular embodiments, provided herein is a method of preparing a liquid dosage form comprising decitabine, which is substantially free of impurities. In one embodiment, the method comprises reconstituting a sterile lyophilized powder comprising decitabine with cold sterile water. In one embodiment, the cold sterile water used in reconstitution has a temperature of between about 2° C. and about 8° C., between about 2° C. and about 6° C., or between about 2° C. and about 4° C.

In particular embodiments, the method comprises reconstituting a sterile lyophilized powder comprising 5-azacytidine and mannitol with cold sterile water. In one embodiment, the method comprises reconstituting a sterile lyophilized powder comprising about 100 mg of 5-azacytidine and about 100 mg of mannitol with about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, or about 20 mL of cold sterile water.

In one embodiment, the reconstituted liquid dosage form is used for parenteral administration after the dosage form is allowed to warm to about room temperature (e.g., over a period of less than about 30 minutes). In one embodiment, the method may further comprise optionally storing the reconstituted liquid dosage form (e.g., in a syringe or a vial) at a temperature of less than about 10° C., less than about 8° C., less than about 6° C., less than about 4° C., less than about 2° C., less than about 0° C., less than about −10° C., or less than about −20° C. In one embodiment, the liquid dosage form is stored for about 12 hours, about 24 hours, about 36 hours, about 48 hours, about 3 days, about 4 days, about 5 days, about 7 days, about 10 days, about 14 days, up to 7 days, up to 14 days, or greater than 14 days. In one embodiment, the method may further comprises allowing the stored liquid composition to warm to room temperature prior to parenteral administration. In one embodiment, the composition remains sterile after storage. In one embodiment, the composition remains sterile after warmed to room temperature. In one embodiment, the method may further comprise adding additional sterile water (e.g., sterile water having an ambient temperature or a temperature of less than about 10° C., less than about 8° C., less than about 6° C., less than about 4° C., less than about 2° C.) to the reconstituted liquid dosage form to prepare a solution of the cytidine analog (e.g., 5-azacytidine or decitabine) for intravenous administration. In one embodiment, the water used for reconstitution is sterile Water for Injection.

In particular embodiments, the method comprises reconstituting a sterile lyophilized powder comprising about 100 mg of 5-azacytidine and about 100 mg of mannitol with about 4 mL of cold sterile Water for Injection to form an opaque, white suspension (i.e., about 25 mg/mL), which may be used for parenteral administration (e.g., subcutaneous administration). In one embodiment, the reconstituted liquid dosage form is allowed to warm to room temperature (e.g., within a period of less than about 30 minutes) before parenteral use. The aqueous solubility of 5-azacytidine at about 25° C. is about 14 mg/mL. In some embodiments, when the dosage form is at room temperature, about one-half of 5-azacytidine is dissolved, with about the other half present as solid in the suspension.

In certain embodiments, the formulation of the cytidine analog, such as, for example, 5-azacytidine or decitabine, is prepared using water or aqueous solvents without causing significant hydrolytic degradation of the cytidine analog. In certain embodiments, the formulation of the cytidine analog, such as, for example, 5-azacytidine or decitabine, is prepared using cold water or cold aqueous solvents, without causing significant hydrolytic degradation of the cytidine analog.

3. Parenteral Administration

In one embodiment, the pharmaceutical compositions provided herein are useful for parenteral administration. In one embodiment, the pharmaceutical compositions and dosage forms provided herein can be used in the preparation of individual, single unit dosage forms. Pharmaceutical compositions and dosage forms provided herein comprise a cytidine analog provided herein, or a pharmaceutically acceptable salt, solvate, hydrate, stereoisomer, precursor, derivative, clathrate, or prodrug thereof. In one embodiment, the pharmaceutical compositions and dosage forms provided herein optionally further comprise one or more excipient(s), such as, e.g., mannitol, potassium dihydrogen phosphate, and/or sodium hydroxide.

In one embodiment, the pharmaceutical compositions and dosage forms provided herein further comprise one or more second or additional active ingredient(s). Examples of optional second, or additional, active ingredients are disclosed herein elsewhere. The specific amount of the second active agent will depend on the specific agent used, the diseases or disorders being treated or managed, and the amount(s) of the cytidine analog used, and any optional additional active agents concurrently administered to the patient.

In one embodiment, the single unit dosage forms provided herein are suitable for parenteral (e.g., subcutaneous, intravenous, bolus injection, intramuscular, intra-arterial, transdermal, or transcutaneous) administration to a patient. Examples of dosage forms include, but are not limited to:

liquid dosage forms suitable for parenteral administration (e.g., solution or suspension); dispersions; emulsions; solutions; suspensions (e.g., aqueous or non-aqueous liquid suspensions, oil-in-water emulsions, or a water-in-oil liquid emulsions); and powders (e.g., sterile lyophilized powders) or solids (e.g., sterile crystalline or amorphous solids) that can be reconstituted to provide liquid dosage forms (e.g., solution or suspension) suitable for parenteral administration to a patient.

The composition, amount, and type of dosage forms will typically vary depending on their use and/or the properties of the active ingredient. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences*, 18th Ed., Mack Publishing, Easton Pa., 1990; Allen et al., Ansel's Pharmaceutical Dosage Forms and Drug Delivery Systems, $9^{th}$ ed., 2010; Remington: The Science and Practice of Pharmacy, $21^{st}$ ed., 2005.

In one embodiment, pharmaceutical compositions and dosage forms comprise one or more excipient(s). Suitable excipients are known to those skilled in the art of pharmacy, and non-limiting examples of suitable excipients are provided herein. Whether a particular excipient is suitable for incorporation into a pharmaceutical composition or dosage form depends on a variety of factors known in the art including, but not limited to, the way in which the dosage form will be administered to a patient. The suitability of a particular excipient may also depend on the specific active ingredients in the dosage form. For example, the decomposition of some active ingredients may be accelerated by some excipients, such as lactose, or when exposed to water. Active ingredients that comprise primary or secondary amines are particularly susceptible to such accelerated decomposition. In one embodiment, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient. Lactose-free compositions can comprise excipients that are well known in the art and are listed, for example, in the U.S. Pharmacopeia (USP) 25-NF20 (2002). In one embodiment, when the cytidine analog is 5-azacytidine, the liquid composition or formulation comprising 5-azacytidine does not contain 5% Dextrose solution, Hespan, or solutions that contain bicarbonate, because these solutions may have the potential to increase the rate of degradation of 5-azacytidine.

In one embodiment, examples of excipients useful in preparing the formulations provided herein are described in, e.g., Allen et al., Ansel's Pharmaceutical Dosage Forms and Drug Delivery Systems, $9^{th}$ ed., 2010; Remington: The Science and Practice of Pharmacy, $21^{st}$ ed., 2005, both of which are incorporated herein by reference in their entireties.

In one embodiment, also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

In certain embodiments, an anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs. In one embodiment, provided herein is a sterile lyophilized powder comprising a cytidine analog (e.g., 5-azacytidine or decitabine) in a sealed vial which may be reconstituted with sterile water or sterile vehicle to yield a dosage form suitable for parenteral administration. In one embodiment, the sterile lyophilized powder may be stored for up to about 24 months, up to about 36 months, up to about 48 months, or greater than about 48 months, before reconstitution for parenteral use.

In one embodiment, the pharmaceutical compositions or dosage forms provided herein may further comprise one or more additives or excipients, such as, e.g., antibacterial preservatives, buffers, solubilizers, stabilizers, antioxidants, tonicity agents, and other pharmaceutical excipients.

In one embodiment, the pharmaceutical compositions or dosage forms provided herein further comprise mannitol. In one embodiment, the weight ratio of the cytidine analog (e.g., 5-azacytidine) and mannitol is about 1:1 w/w. In other embodiments, the weight ratio of the cytidine analog (e.g., 5-azacytidine) and mannitol is about 10:1 w/w, about 5:1 w/w, about 2:1 w/w, about 1:2 w/w, about 1:5 w/w, or about 1:10 w/w.

In one embodiment, provided herein are pharmaceutical compositions and dosage forms that comprise one or more additives that reduce the rate by which an active ingredient will decompose. Such additives, which are referred to herein as "stabilizers," include, but are not limited to, antioxidants such as ascorbic acid, pH buffers, or salt buffers.

In one embodiment, the pharmaceutical compositions provided herein can be administered parenterally by injection, infusion, or implantation, for local or systemic administration. In one embodiment, parenteral administration, as used herein, include intravenous, intra-arterial, intraperitoneal, intrathecal, intraventricular, intraurethral, intrasternal, intracranial, intramuscular, intrasynovial, intravesical, and subcutaneous administration, among others.

In one embodiment, parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In certain embodiments, the pharmaceutical compositions provided herein for parenteral administration can be formulated in any dosage forms that are suitable for use in parenteral administration, including solutions, suspensions, emulsions, micelles, liposomes, microspheres, nanosystems, and solid forms which may be reconstituted to render solutions or suspensions in liquid prior to injection. Such dosage forms can be prepared according to conventional methods known to those skilled in the art of pharmaceutical science (see, *Remington: The Science and Practice of Pharmacy*, supra). In one embodiment, such dosage forms are sterile, e.g., prepared using a sterilization method known in the art, including, but not limited to, steam sterilization, dry-heat sterilization, sterilization by filtration, gas sterilization, and sterilization by ionizing radiation. In one embodiment, such dosage forms are pyrogen-free. In one embodiment, such dosage forms are prepared and handled following aseptic procedures for preparing injectable products known to those skilled in the art.

Suitable vehicles that can be used to provide parenteral dosage forms are known to those skilled in the art. Examples include, but are not limited to: Water for Injection USP, including, but not limited to, Sterile Water for Injection, and Bacteriostatic Water for Injection; aqueous vehicles, including, but not limited to, Sodium Chloride Injection, including Bacteriostatic Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In one embodiment, the pharmaceutical compositions intended for parenteral administration can include one or more pharmaceutically acceptable carriers or excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases (e.g., nitrogen).

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. In one embodiment, suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. In one embodiment, suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. In one embodiment, suitable isotonic agents include, but are not limited to, sodium chloride, glycerin, and dextrose. In one embodiment, suitable buffering agents include, but are not limited to, phosphate and citrate. In one embodiment, suitable antioxidants are those as described herein, including bisulfate and sodium metabisulfite. In one embodiment, suitable local anesthetics include, but are not limited to, procaine hydrochloride. In one embodiment, suitable suspending and dispersing agents are those as described herein, including sodium carboxymethylcelluose, hydroxypropyl methylcellulose, and polyvinylpyrrolidone. In one embodiment, suitable emulsifying agents are those described herein, including polyoxyethylene sorbitan monolaurate, polyoxyethylene sorbitan monooleate 80, and triethanolamine oleate. In one embodiment, suitable sequestering or chelating agents include, but are not limited to EDTA. In one embodiment, suitable pH adjusting agents include, but are not limited to, sodium hydroxide, hydrochloric acid, citric acid, and lactic acid. In one embodiment, suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

In one embodiment, the pharmaceutical composition or formulation provided herein is a single-use dosage form. In one embodiment, the pharmaceutical composition or formulation provided herein does not contain any preservatives and is sterilized using a procedure known to those of skill in the art. In one embodiment, the pharmaceutical composition or formulation provided herein is supplied in a single-use vial, and any unused portions of each vial is discarded properly (i.e., the unused portions are not saved for later administration).

In one embodiment, the pharmaceutical compositions provided herein can be provided in a unit-dosage form or multiple-dosage form. A unit-dosage form, as used herein, refers to physically discrete a unit suitable for administration to a human or animal subject, and packaged individually as is known in the art. In certain embodiments, each unit-dose contains a predetermined quantity of an active ingredient(s) sufficient to produce a desired therapeutic effect, in association with the required pharmaceutical carriers or excipients. Examples of a unit-dosage form include an ampoule, syringe, and individually packaged container, such as, a vial. For example, a 100 mg unit dose contains about 100 mg of an active ingredient in a packaged container. A unit-dosage form may be administered in fractions or multiples thereof. In one embodiment, a multiple-dosage form is a plurality of identical unit-dosage forms packaged in a single container to be administered in segregated unit-dosage form. Examples of a multiple-dosage form include a vial, or bottle of pints or gallons.

In one embodiment, when the pharmaceutical compositions provided herein are formulated for multiple dosage administration, the multiple dosage parenteral formulations may contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein for parenteral administration can be formulated as immediate or modified release dosage forms, including delayed-, sustained, pulsed-, controlled, targeted-, and programmed-release forms.

In one embodiment, the pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In one embodiment, the pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; Polymers in Drug Delivery; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deilv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

In one embodiment, the pharmaceutical compositions provided herein can be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759, 542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

In one embodiment, the pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved or suspended to form a sterile particulate-free solution or a sterile suspension that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In one embodiment, the pharmaceutical compositions or formulations provided herein are administered subcutaneously. Generally, the subcutaneous route may be utilized for the injection of small amounts of a medication. In one embodiment, the formulation is an aqueous solution, which is administered subcutaneously. In one embodiment, the formulation is an aqueous suspension, which is administered subcutaneously. In certain embodiments, the vial or syringe containing the aqueous suspension is vigorously shaken or rolled to form a uniform or homogenous suspension, e.g., prior to subcutaneous injection. In one embodiment, the suspension may be cloudy in appearance. In certain embodiments, the formulation is injected beneath the surface of the skin in the loose interstitial tissues, for example, at the outer surface of the upper arm, the anterior surface of the thigh, or the lower portion of the abdomen. In certain embodiments, one or more injection sites may be used to deliver an intended dose to a patient. For example, in certain embodiments, a drug formulation with a volume of greater than about 4 mL may be divided into two or more portions and injected at two or more different sites of the patient to deliver an intended dose of the drug. The injection sites may be rotated for each injection (e.g., thigh, abdomen, or upper arm). In one embodiment, new injections are given at least one inch from an old site of injection, and not into an area where the site is tender, bruised, red, or hard.

In one embodiment, the pharmaceutical compositions or formulations provided herein are administered intravenously. Both small and large volumes of drug solutions may be administered intravenously. In one embodiment, the solutions for intravenous administration may optionally further contain nutrients, blood extenders, electrolytes, amino acids, and/or other therapeutic agents. In one embodiment, a solid composition comprising a cytidine analog, such as, e.g., a lyophilized powder, is reconstituted in a vial with a certain amount of sterile water for injection to form a solution. In one embodiment, the vial containing the mixture of sterile water and the solid composition comprising the cytidine analog is vigorously shaken or rolled until all solids are dissolved. In one embodiment, the resulting solution appears to be clear and does not contain any substantial particulate matter. In one embodiment, a required amount of the resulting solution comprising the cytidine analog is withdrawn from the vial to deliver a desired dose of the cytidine analog. In one embodiment, the resulting solution comprising the cytidine analog is withdrawn from the vial and injected into an intravenous infusion bag, such as, e.g., a 50-100 mL I.V. infusion bag, containing, e.g., 0.9% Sodium Chloride Injection or Lactated Ringer's Injection. In one embodiment, the drug solution comprising a cytidine analog (e.g., 5-azacytidine or decitabine) is administered through an in-dwelling needle or catheter by continuous infusion. The infusion or flow rates may be adjusted according to the needs of the individual patient. In one embodiment, the flow rates for intravenous fluids may range from about 42 mL/hour to about 150 mL/hour. Lower rates are used for "keep open" lines. In one embodiment, the needle or catheter is placed in the prominent veins of the forearm or leg and taped firmly to the patient to prevent the needle or catheter from slipping from place during infusion. In certain embodiments, the total dose of the cytidine analog (e.g., 5-azacytidine or decitabine) is delivered over a period of between about 10 minutes and about 40 minutes. In certain embodiments, the total dose of the cytidine analog (e.g., 5-azacytidine or decitabine) is delivered over a period of between about 0.5 hr and about 4 hr, or between about 1 hr and about 3 hr. In certain embodiments, the administration of the cytidine analog to a patient is complete within one hour of reconstitution of the drug in the vial. In certain embodiments, when a liquid formulation comprising a cytidine analog (e.g., 5-azacytidine or decitabine) is reconstituted and stored at a low temperature prior to use, the formulation is allowed to equilibrate to room temperature and administered to a patient within one hour.

Specific embodiments herein provide any of the aforementioned compositions, as single unit dosage forms, e.g., a prepackaged lyophilized powder in a vial or an aqueous suspension or solution in a vial, syringe, or I.V. bag.

4. Methods of Treatment

In one embodiment, provided herein is a method of using the pharmaceutical composition provided herein to treat, prevent, or manage a disease or disorder, including cancer, disorders related to abnormal cell proliferation, and hematologic disorders (e.g., MDS). In certain embodiments, provided herein is a method of using the pharmaceutical composition provided herein to treat one or more symptoms of a disease or disorder, including cancer, disorders related to abnormal cell proliferation, and hematologic disorders (e.g., MDS). In one embodiment, the pharmaceutical composition provided herein is prepared for use to treat, prevent, or manage a disease or disorder, including cancer, disorders related to abnormal cell proliferation, and hematologic disorders (e.g., MDS).

Certain embodiments herein provide methods of using the pharmaceutical compositions provided herein to treat diseases or disorders including, e.g., cancer, disorders related to abnormal cell proliferation, hematologic disorders, or immune disorders, among others. In certain embodiments, the pharmaceutical compositions of cytidine analogs are parenterally administered to subjects in need thereof to treat a cancer or a hematological disorder, such as, for example, MDS, AML, ALL, CML, NHL, leukemia, or lymphoma; or a solid tumor, such as, for example, sarcoma, carcinoma, melanoma, or cancer of the colon, breast, ovary, gastrointestinal system, kidney, lung (e.g., non-small-cell lung cancer and small-cell lung cancer), testicle, prostate, pancreas, lymphatic system, or bone. In certain embodiments, the pharmaceutical compositions of cytidine analogs are parenterally administered to subjects in need thereof to treat an immune disorder. In certain embodiments, the pharmaceutical compositions provided herein are co-administered with one or more therapeutic agents to provide a synergistic therapeutic effect in subjects in need thereof. In certain embodiments, the pharmaceutical compositions provided herein are co-administered with one or more therapeutic agents to provide a resensitization effect in subjects in need thereof. The co-administered agents may be a cancer therapeutic agent, as described herein. In certain embodiments, the co-administered agent(s) may be dosed, e.g., orally or by injection.

Specific embodiments herein provide, inter alia, methods for treating a subject having a disease associated with abnormal cell proliferation (e.g., MDS), comprising parenterally administering to the subject a pharmaceutical composition comprising a therapeutically effective amount of 5-azacytidine. Specific embodiments herein provide, inter alia, methods for treating a subject having a disease associated with abnormal cell proliferation (e.g., MDS), comprising parenterally administering to the subject a pharmaceutical composition comprising a therapeutically effective amount of decitabine. Further embodiments herein provide the aforementioned methods, in which: the composition accurately delivers an intended dose to the subject; the disease is myelodysplastic syndrome; the disease is acute myelogenous leukemia; the method further comprises co-administering to the subject in need thereof an additional therapeutic agent selected from any additional therapeutic agent disclosed herein; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 5° C., below about 2° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine (or decitabine) is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; and/or the amount of 5-azacytidine (or decitabine) is at least about 25 mg, at least about 50 mg; at least about 75 mg, at least about 100 mg, or at least about 125 mg.

Specific embodiments herein provide, inter alia, pharmaceutical compositions comprising a therapeutically effective amount of 5-azacytidine, for treating a disease or disorder associated with abnormal cell proliferation (e.g., MDS), wherein the compositions are prepared for parenteral administration. Specific embodiments herein provide, inter alia, pharmaceutical compositions comprising a therapeutically effective amount of decitabine, for treating a disease or disorder associated with abnormal cell proliferation (e.g., MDS), wherein the compositions are prepared for parenteral administration. Further embodiments herein provide the aforementioned compositions, in which: the composition accurately delivers an intended dose to the subject; the disease is myelodysplastic syndrome; the disease is acute myelogenous leukemia; the composition is a liquid formulation prepared from cold sterile water (e.g., at a temperature of about 0° C., about 1° C., about 2° C., about 3° C., about 4° C., about 5° C., about 6° C., or about 8° C.); the composition is a liquid formulation prepared from cold sterile water, stored at a temperature of below about 8° C., below about 5° C., below about 2° C., about 0° C., about −10° C., or about −20° C., and warmed to about room temperature prior to parenteral administration; the composition is a single unit dosage form; the composition is a pre-packaged lyophilized powder in a vial; the composition is a liquid formulation (e.g., a suspension or a solution) in a vial, syringe, or I.V. bag; the composition is a solution for intravenous administration; the composition further comprises an excipient selected from any excipient disclosed herein; the amount of 5-azacytidine (or decitabine) is about 25 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg; the amount of 5-azacytidine (or decitabine) is at least about 25 mg, at least about 50 mg; at least about 75 mg, at least about 100 mg, or at least about 125 mg; the composition is prepared to achieve a daily dose of about 30 mg/m$^2$ following parenteral administration; the composition is prepared to achieve a daily dose of about 40 mg/m$^2$ following parenteral administration; the composition is prepared to achieve a daily dose of about 50 mg/m$^2$ following parenteral administration; the composition is prepared to achieve a daily dose of about 75 mg/m$^2$ following parenteral administration; the composition is prepared to achieve a daily dose of about 100 mg/m$^2$ following parenteral administration; the composition is prepared to achieve a daily dose of about 125 mg/m$^2$ following parenteral administration; the composition is prepared to achieve a daily dose of about 150 mg/m$^2$ following parenteral administration; the composition is prepared to achieve a daily dose of between about 50 mg/m$^2$ and about 100 mg/m$^2$ following parenteral administration; the composition is prepared for parenteral administration in combination with an additional therapeutic agent selected from any additional therapeutic agent disclosed herein; the composition is prepared for treating myelodysplastic syndrome or acute myelogenous leukemia; the composition is a single unit dosage form; and/or the composition further comprises an excipient selected from any excipient disclosed herein.

Specific embodiments herein provide, inter alia, uses of 5-azacytidine for the preparation of a pharmaceutical composition for treating a disease associated with abnormal cell proliferation (e.g., MDS), wherein the composition is prepared for parenteral administration, and wherein the composition is prepared from cold sterile water (e.g., having a temperature of about 0° C., about 2° C., about 4° C., about 6° C., about 8° C., or about 10° C.). Further embodiments herein provide the aforementioned uses, in which: the disease is myelodysplastic syndrome or acute myelogenous leukemia; the amount of 5-azacytidine is selected from any amount disclosed herein; and/or the composition is prepared for immediate parenteral use or for parenteral use after storage for a certain period of time. Further embodiments provide, inter alia, methods for treating a subject having a disease or disorder provided herein by administering a pharmaceutical compositions provided herein, wherein the treatment results in improved survival of the subject.

In particular embodiments, the pharmaceutical compositions comprising the cytidine analogs, such as, for example, 5-azacytidine or decitabine, comprise a therapeutically or prophylactically effective amount of the cytidine analog (and, optionally, one or more excipients). In particular embodiments, the pharmaceutical compositions comprising the cytidine analogs, such as, for example, 5-azacytidine or decitabine, is prepared to deliver a therapeutically or prophylactically effective amount of the cytidine analog to a subject in need thereof.

In one embodiment, provided herein are methods of treating patho-physiological conditions manifested by abnormal cell proliferation, such as, for example, cancer, including hematological disorders and solid tumors, by parenterally administering a pharmaceutical formulation comprising a cytidine analog, such as, for example, 5-azacytidine or decitabine. Other embodiments herein provide methods of treating immune disorders. In certain embodiments, the cytidine analog and one or more therapeutic agents are co-administered to subjects to yield a synergistic therapeutic effect. The co-administered agent may be a cancer therapeutic agent dosed orally or by injection.

In certain embodiments, methods provided herein for treating disorders related to abnormal cell proliferation comprise parenterally administering a formulation comprising a therapeutically effective amount of a cytidine analog. Particular therapeutic indications relating to the methods provided herein are disclosed herein. In certain embodiments, the therapeutically effective amount of the cytidine analog in the pharmaceutical formulation is an amount as disclosed herein. In certain embodiments, the precise therapeutically effective amount of the cytidine analog in the pharmaceutical formulation will vary depending on, e.g., the age, weight, disease and/or condition of the subject.

In particular embodiments, the disorders related to abnormal cell proliferation include, but are not limited to, MDS, AML, ALL, CML, leukemia, chronic lymphocytic leukemia (CLL), lymphoma (including non-Hodgkin's lymphoma (NHL) and Hodgkin's lymphoma), multiple myeloma (MM), sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, pancreatic cancer, bone cancer, gastric cancer, head and neck cancer, and prostate cancer. In particular embodiment, the disorder related to abnormal cell proliferation is MDS. In particular embodiments, the disorder related to abnormal cell proliferation is AML.

In certain embodiments, methods provided herein comprise treating a disorder provided herein, including a hematologic disorder, by administering a parenteral dosage form comprising a cytidine analog to a subject in need thereof. In particular embodiments, parenteral dosage forms provided herein comprising 5-azacytidine are used to treat subjects having hematologic disorders. In particular embodiments, parenteral dosage forms provided herein comprising decitabine are used to treat subjects having hematologic disorders. Hematologic disorders include, e.g., abnormal growth of blood cells which can lead to dysplastic changes in blood cells and hematologic malignancies such as various leukemias. Examples of hematologic disorders include, but are not limited to, acute myeloid leukemia (AML), acute promyelocytic leukemia (APML), acute lymphoblastic leukemia (ALL), chronic myelogenous leukemia (CML), chronic lymphocytic leukemia (CLL), myelodysplastic syndromes (MDS), and sickle cell anemia, among others. Other disorders that can be treated using the methods provided herein include, e.g., multiple myeloma (MM) and non-Hodgkin's lymphoma (NHL).

In certain embodiments, methods provided herein comprise treating AML by administering a parenteral dosage form comprising a cytidine analog to a subject in need thereof. AML is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

In certain embodiments, methods provided herein comprise treating APML by administering a parenteral dosage form comprising a cytidine analog to a subject in need thereof. APML represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

In certain embodiments, methods provided herein comprise treating ALL by administering a parenteral dosage form comprising a cytidine analog to a subject in need thereof. ALL is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the subject.

In certain embodiments, methods provided herein comprise treating CML by administering a parenteral dosage form comprising a cytidine analog to a subject in need thereof. CML is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

In certain embodiments, methods provided herein comprise treating MDS by administering a parenteral dosage form comprising a cytidine analog to a subject in need thereof. In certain embodiments, MDS includes one or more of the following myelodysplastic syndrome subtypes: refractory anemia, refractory anemia with ringed sideroblasts (if accompanied by neutropenia or thrombocytopenia or requiring transfusions), refractory anemia with excess blasts, refractory anemia with excess blasts in transformation, and chronic myelomonocytic leukemia. In certain embodiments, the MDS is higher-risk MDS. See, e.g., U.S. patent application Ser. No. 12/740,636, which is incorporated by reference herein in its entirety. In certain embodiments, the methods provided herein comprise administering a parenteral dosage form comprising a cytidine analog to a subject in need thereof to increase the survival (e.g., prolong the life) of a subject with MDS.

In certain embodiments, methods provided herein comprise treating NHL by administering a parenteral dosage form comprising a cytidine analog to a subject in need thereof. Non-Hodgkin's Lymphomas (NHL) represent a heterogeneous group of malignancies of the lymphoid system. According to the WHO classification of hematological and lymphoid tumors, these diseases are classified as B-cell and T-cell neoplasms. B-cell lymphomas account for about 90% of all lymphomas, and the two most common histological disease entities are follicular lymphoma and diffuse large B-cell lymphoma. Approximately 55,000 to 60,000 new cases of NHL are diagnosed annually in the U.S. See, e.g., Ansell, S. M., et al., *Mayo Clin. Proc.*, 2005, 80(8):1087-97.

In certain embodiments, methods provided herein comprise treating MM by administering a parenteral dosage form comprising a cytidine analog to a subject in need thereof. Multiple myeloma is one of the most commonly diagnosed hematologic malignancies. In 2007, in the U.S. alone, there were roughly 20,000 new MM cases and 10,000 deaths due to MM. The disease is characterized by, inter alia, an accumulation of malignant plasma cells in the bone marrow, which can lead to the overproduction of an immunoglobulin, e.g., a monoclonal immunoglobulin G or A. These immunoglobulins, also known as paraproteins, can be detected in the urine and blood of patients with MM. Consequences of MM include anemia, the development of destructive bony lesions, and renal insufficiency. See, e.g., Rao, K. V., *American Journal of Health-System Pharmacy*, 2007, 64(17):1799-1807.

In certain embodiments, methods provided herein comprise treating CLL by administering a parenteral dosage form comprising a cytidine analog to a subject in need thereof. Chronic lymphocytic lymphoma (CLL) is a malignancy of mature B lymphocytes and is the most prevalent lymphoid malignancy in the U.S. The WHO classification of B lymphocytic neoplasms groups B cell malignancies according to the presumed normal counterpart of the malignant cells. CLL is diagnosed by immunophenotype analysis of lymphocytes from the blood, bone marrow, or lymph nodes. See, e.g., Zent, C. S., et al., *Current Oncology Reports*, 2007, 9:345-52.

Certain embodiments herein provide methods of treating a condition involving undesirable or uncontrolled cell proliferation by administering a parenteral formulation comprising a cytidine analog (e.g., 5-azacytidine or decitabine) as provided herein. Such conditions include, e.g., benign tumors, various types of cancers such as primary tumors and tumor metastasis, hematological disorders (e.g. leukemia, myelodysplastic syndrome and sickle cell anemia), restenosis (e.g. coronary, carotid, and cerebral lesions), abnormal stimulation of endothelial cells (arteriosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

In certain embodiments, cells in a benign tumor retain their differentiated features and do not divide in a completely uncontrolled manner. A benign tumor may be localized and/or nonmetastatic. Specific types of benign tumors that can be treated using the methods, compositions, and formulations provided herein include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In certain embodiments, cells in a malignant tumor become undifferentiated, do not respond to the body's growth control signals, and/or multiply in an uncontrolled manner. The malignant tumor may be invasive and capable of spreading to distant sites (metastasizing). Malignant tumors may be divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.).

Methylation can lead to the silencing of genes critical to cellular control (i.e., epigenetic gene silencing), and can be an early event in the development of malignant tumors including, e.g., colorectal cancer or lung cancer. See, e.g., M. V. Brock et al., *N. Engl. J. Med.*, 2008, 358(11):1118-28; P. M. Das et al., *Mol. Cancer*, 2006, 5(28); G. Gifford et al., *Clin. Cancer Res.*, 2004, 10:4420-26; J. G. Herman et al., *N. Engl. J. Med.*, 2003, 349:2042-54; A. M. Jubb et al., *J. Pathology*, 2001, 195:111-34. Accordingly, in certain embodiments, methods herein provide using parenteral formulations provided herein to prevent or reverse epigenetic gene silencing, e.g., by reversing abnormal DNA methylation. In specific embodiments, parenteral formulations provided herein are used for early intervention to prevent the development of cancer in patients at risk of developing cancer, e.g., familial polyposis or lung cancer, wherein a cause of the cancer is epigenetic gene silencing. In specific embodiments, the formulations provided herein are used for early intervention to prevent the recurrence of cancer in patients at risk for early relapse, e.g., colorectal cancer or non-small-cell lung cancer. In certain embodiments, the early intervention is achieved via prolonged dosing schedules, using formulations and/or methods as described herein. Certain embodiments provide methods for administering the formulations provided herein to reverse the effect of gene silencing, e.g., in patients at risk of gene silencing due to epigenetic changes. In particular embodiments, methods provided herein further comprise administering an HDAC inhibitor compound (e.g., to restore chromatin to a transcriptionally active configuration after reversing abnormal DNA methylation). In particular embodiments, the HDAC inhibitor compound is entinostat (SNDX-275; formerly MS-275), an oral HDAC inhibitor that acts synergistically with targeted therapies and is selective for cancer-relevant HDAC isoforms 1, 2, and 3. In particular embodiments, a synergistic effect is achieved by co-administering 5-azacytidine and an HDAC inhibitor (e.g., entinostat) for the treatment of solid tumors (e.g., NSCLC) or hematological malignancies (e.g., MDS, CMMoL., or AML).

In certain embodiments, specific types of cancers or malignant tumors, either primary or secondary, that can be treated using the methods, compositions, and formulations provided herein include, e.g., leukemia, breast cancer, skin cancer, bone cancer, prostate cancer, liver cancer, lung cancer (e.g., non-small-cell lung cancer and small-cell lung cancer), brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma., veticulum cell sarcoma, myeloma, giant cell tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronmas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, medulloblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Particular embodiments herein provide using the methods, compositions, and formulations provided herein to treat abnormal cell proliferation due to, e.g., insults to body tissue during surgery for a variety of surgical procedures, including, e.g., joint surgery, bowel surgery, and cheloid scarring. Proliferative responses associated with organ transplantation that may be treated using the methods, compositions, and formulations provided herein include those proliferative responses contributing to potential organ rejections or associated complications. Specifically, these proliferative responses may occur during transplantation of the heart, lung (e.g., non-small-cell lung cancer and small-cell lung cancer), liver, kidney, and other body organs or organ systems.

In certain embodiments, the amount of the cytidine analog in the formulations provided herein, the methods of administration thereof, or the methods of treatment as set forth herein, is a specific dosage amount as provided herein. In certain embodiments, the 5-azacytidine or decitabine dosages, methods of administration thereof, or methods of treatment of at least one condition, including but not limited to MDS and AML, may range, e.g., between about 50 $mg/m^2/day$ and about 2,000 $mg/m^2/day$, between about 50 $mg/m^2/day$ and about 1,000 $mg/m^2/day$, between about 50 $mg/m^2/day$ and about 500 $mg/m^2/day$, or between about 50 $mg/m^2/day$ and about 100 $mg/m^2/day$. In certain embodiments, particular dosages are, e.g., about 20 $mg/m^2/day$, about 40 $mg/m^2/day$, about 50 $mg/m^2/day$, about 60 $mg/m^2/day$, about 70 $mg/m^2/day$, about 80 $mg/m^2/day$, about 90 $mg/m^2/day$, about 100 $mg/m^2/day$, about 110 $mg/m^2/day$, about 120 mg/m²/day, about 140 mg/m²/day, about 150 mg/m²/day, about 160 mg/m²/day, about 180 mg/m²/day, about 200 mg/m²/day, about 220 mg/m²/day, about 250 mg/m²/day, about 280 mg/m²/day, or about 300 mg/m²/day.

In certain embodiments, appropriate biomarkers may be used to determine or predict the effect of the pharmaceutical compositions comprising cytidine analogs on the disease state and to provide guidance to the dosing schedule. For example, particular embodiments herein provide a method of determining whether a patient diagnosed with MDS has an increased probability of obtaining a greater benefit from treatment with a pharmaceutical composition comprising a cytidine analog by assessing the patient's nucleic acid methylation status. In particular embodiments, the cytidine analog is 5-azacytidine. In particular embodiments, the cytidine analog is decitabine. In particular embodiments, the nucleic acid is DNA or RNA. In particular embodiments, the greater benefit is an overall survival benefit. In particular embodiments, the methylation status is examined in one or more genes, e.g., genes associated with MDS or AML. Specific embodiments involve methods for determining whether baseline DNA methylation levels influence overall survival in patients with MDS (e.g., higher risk MDS) treated with 5-azacytidine or decitabine. Specific embodiments provide methods for determining whether gene promoter methylation levels influence overall survival in patients with MDS (e.g., higher risk MDS).

For example, specific embodiments herein provide methods for evaluating the influence of gene methylation on prolonged survival in patients with MDS (e.g., higher risk MDS). In particular embodiments, such evaluation is used to predict overall survival in patients with MDS (e.g., higher risk MDS), e.g., upon treatment with a pharmaceutical composition comprising a cytidine analog, as provided herein. In particular embodiments, such evaluation is used for therapeutic decision-making. In specific embodiments, such therapeutic decision-making includes planning or adjusting a patient's treatment, e.g., the dosing regimen, amount, and/or duration of administration of the cytidine analogue.

Certain embodiments provide methods of identifying individual patients diagnosed with MDS having an increased probability of obtaining an overall survival benefit from cytidine analog treatment, using analysis of methylation levels, e.g., in particular genes. In specific embodiments, lower levels of nucleic acid methylation are associated with an increased probability of obtaining improved overall survival following 5-azacytidine treatment. In particular embodiments, the increased probability of obtaining improved overall survival following treatment is at least a 5% greater probability, at least a 10% greater probability, at least a 20% greater probability, at least a 30% greater probability, at least a 40% greater probability, at least a 50% greater probability, at least a 60% greater probability, at least a 70% greater probability, at least an 80% greater probability, at least a 90% greater probability, at least at least a 100% greater probability, at least a 125% greater probability, at least a 150% greater probability, at least a 175% greater probability, at least a 200% greater probability, at least a 250% greater probability, at least a 300% greater probability, at least a 400% greater probability, or at least a 500% greater probability of obtaining improved overall survival following treatment, e.g., using a pharmaceutical composition comprising a cytidine analog as provided herein. In particular embodiments, the greater probability of obtaining improved overall survival following treatment is a greater probability as compared to the average probability of a particular comparison population of patients diagnosed with MDS. In specific embodiments, the comparison population is a group of patients classified with a particular myelodysplastic subtype, as described herein. In one embodiment, the comparison population consists of patients having higher risk MDS. In particular embodiments, the comparison population consists of a particular IPSS cytogenetic subgroup.

In particular embodiments, nucleic acid (e.g., DNA or RNA) hypermethylation status may be determined by any method known in the art. In certain embodiments, DNA hypermethylation status may be determined using the bone marrow aspirates of patients diagnosed with MDS, e.g., by using quantitative real-time methylation specific PCR ("qMSP"). In certain embodiments, the methylation analysis may involve bisulfite conversion of genomic DNA. For example, in certain embodiments, bisulfite treatment of DNA is used to convert non-methylated CpG sites to UpG, leaving methylated CpG sites intact. See, e.g., Frommer, M., et al., *Proc. Nat'l Acad. Sci. USA* 1992, 89:1827-31. Commercially available kits may be used for such bisulfite treatment. In certain embodiments, to facilitate methylation PCR, primers are designed as known in the art, e.g., outer primers which amplify DNA regardless of methylation status, and nested primers which bind to methylated or non-methylated sequences within the region amplified by the first PCR. See, e.g., Li et al., *Bioinformatics* 2002, 18:1427-31. In certain embodiments, probes are designed, e.g., probes which bind to the bisulfite-treated DNA regardless of methylation status. In certain embodiments, CpG methylation is detected, e.g., following PCR amplification of bisulfite-treated DNA using outer primers. In certain embodiments, amplified product from the initial PCR reaction serves as a template for the nested PCR reaction using methylation-specific primers or non-methylation-specific primers. In certain embodiments, a standard curve is established to determine the percentage of methylated molecules in a particular sample. Methods for detecting nucleic acid methylation (e.g., RNA or DNA methylation) are known in art. See, e.g., Laird, P. W., *Nature Rev. Cancer* 2003, 3:253-66; Belinsky, S. A., *Nature Rev. Cancer* 2004, 4:1-11.

In certain embodiments, statistical analyses are performed to assess the influence of particular methylation levels with the potential benefit of treatment with a particular pharmaceutical composition comprising a cytidine analog. In certain embodiments, the influence of methylation on overall survival is assessed, e.g., using Cox proportional hazards models and Kaplan-Meier (KM) methodology.

In certain embodiments, any gene associated with MDS and/or AML may be examined for its methylation status in a patient. Particular genes include, but are not limited to, CKDN2B (p15), SOCS1, CDH1 (E-cadherin), TP73, and CTNNA1 (alpha-catenin). Particular genes associated with MDS and/or AML, which would be suitable for use in the methods disclosed here, are known in the art.

Certain embodiments herein provide methods for delivering a cytidine analog to a subject comprising administering to the subject in need thereof a parenteral formulation comprising a cytidine analog. In certain embodiments, provided herein is a method of accurately deliver an intended dose of a cytidine analog to a subject comprising administering to the subject in need thereof a parenteral formulation comprising a cytidine analog as provided herein.

In some embodiments, methods provided herein for treating disorders of abnormal cell proliferation comprise administering a cytidine analog using at least one of IV, SC and oral administration methods. For example, particular embodiments herein provide administering an initial treatment cycle of a cytidine analog, such as, for example, 5-azacytidine or decitabine, administered either SC or IV, followed by subsequent SC, IV, or orally administered treatment cycles of the cytidine analog. In certain embodiments, treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, or greater than 21 days). Particular embodiments herein provide a treatment schedule comprising SC and/or IV administration for one, two, three, four, five, or more initial cycles, followed by SC, IV, and/or oral administration for subsequent cycles. For example, particular embodiments herein provide a treatment schedule comprising SC or IV administration for cycle 1, followed by SC, IV, or oral administration for subsequent cycles. Suitable dosage ranges and amounts for the methods provided herein are provided throughout the specification. For example, in certain embodiments, the SC or IV dose is about 50 mg/m$^2$, about 75 mg/m$^2$, or about 100 mg/m$^2$. In certain embodiments, the oral dose is about 60 mg, about 80 mg, about 120 mg, about 180 mg, about 240 mg, about 300 mg, about 360 mg, about 480 mg, or greater than about 480 mg. In certain embodiments, oral doses are calculated to achieve 80%, 100%, or 120% of SC AUC. Certain oral formulations or oral administration methods are described in U.S. patent application Ser. No. 12/466,213, which is incorporated by reference herein in its entirety.

In certain embodiments, methods of treating disorders of abnormal cell proliferation comprises parenterally administering a formulation comprising a cytidine analog (e.g., 5-azacytidine or decitabine) as single or multiple daily doses. In particular embodiments, the formulation(s) comprising the cytidine analog is/are parenterally administered once per day, twice per day, three times per day, four times per day, or more than four times per day. For example, in certain embodiments, the formulation comprising the cytidine analog is administered using a treatment cycle comprising administration of about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg of the cytidine analog once, twice, three, or four times per day for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In certain embodiments, the method of treating comprises continuous low-dose administration. Certain embodiments herein provide methods comprising administering the formulations of cytidine analogs provided herein comprising delivering the cytidine analog (e.g., 5-azacytidine or decitabine) at a lower dose over a more prolonged period of time. In particular embodiments, such methods comprise managing dose-related cytopenias (including, e.g., dose-related cytopenias associated with 5-azacytidine) by administering a formulation provided herein. In particular embodiments, certain methods herein provide administering the formulations provided herein at lower doses for more prolonged periods of time, leading to improved demethylation.

In certain embodiments, methods provided herein comprise administering a formulation comprising a cytidine analog using one or more of the cycles provided herein, and repeating one or more of the cycles for a period of, e.g., 1, 2, 3, 4, 5, 6, 7, 8, 9, 10, 11, 12, or greater than 12 months.

Particular embodiments herein provide methods for treating a subject having a disease or disorder provided herein by parenterally administering a pharmaceutical composition provided herein, wherein the treatment results in improved survival of the subject. In certain embodiments, the improved survival is measured as compared to one or more conventional care regimens. Particular embodiments herein provide methods for treating a subject having a disease or disorder provided herein by parenterally administering a pharmaceutical composition provided herein, wherein the treatment provides improved effectiveness. In particular embodiments, the improved effectiveness is measured using one or more endpoints for cancer clinical trials, as recommended by the U.S. Food and Drug Administration (FDA). For example, FDA provides Guidance for Industry on Clinical Trial Endpoints for the Approval of Cancer Drugs and Biologics (http://www.fda.gov/CbER/gdlns/clintrialend.htm). The FDA endpoints include, but are not limited to, Overall Survival, Endpoints Based on Tumor Assessments such as (i) Disease-Free Survival (ii) Objective Response Rate, (iii) Time to Progression and Progression-Free Survival and (iv) Time-to-Treatment Failure. Endpoints Involving Symptom Endpoints may include Specific Symptom Endpoints such as (i) Time to progression of cancer symptoms and (ii) A composite symptom endpoint. Biomarkers assayed from blood or body fluids may also be useful to determine the management of the disease.

Particular embodiments herein provide a method of treating a disease or disorder, including cancer, disorders related to abnormal cell proliferation, and hematologic disorders (e.g., MDS), using a pharmaceutical composition comprising 5-azacytidine, as provided herein elsewhere, wherein the method comprises administering about 75 mg/m$^2$ of 5-azacytidine per day for 7 days. In one embodiment, the pharmaceutical composition comprising 5-azacytidine is administered parenterally. In one embodiment, the pharmaceutical composition comprising 5-azacytidine is administered subcutaneously or intravenously. In certain embodiments, the subject may be premedicated for nausea and/or vomiting prior to treatment. In certain embodiments, the daily dose is about 50 mg/m$^2$, about 75 mg/m$^2$, or about 100 mg/m$^2$. In certain embodiments, the daily dose is between about 50 mg/m$^2$ and about 100 mg/m$^2$. In certain embodiments, the average daily dose is between about 50 mg/m$^2$ and about 100 mg/m$^2$.

In certain embodiments, provide herein is a method of treating a disease or disorder, including cancer, disorders related to abnormal cell proliferation, and hematologic disorders (e.g., MDS), using a pharmaceutical composition comprising 5-azacytidine, as provided herein elsewhere, wherein the method comprises carrying out the treatment in cycles, wherein the first treatment cycle comprises administering about 75 mg/m$^2$ of 5-azacytidine per day for 7 days, followed by a 21-day break. In certain embodiments, the treatment cycle is repeated every 4 weeks (e.g., treatment for 7 days, followed by a 21-day break).

In certain embodiments, after the first two treatment cycles, the dose is increased to about 100 mg/m$^2$ of 5-azacytidine per day for 7 days, followed by a 21-day break, for example, when no toxicity other than nausea and vomiting has occurred during the first two treatment cycles and if appropriate for the treated subject. In other embodiments, the dose is maintained at about 75 mg/m$^2$ of 5-azacytidine per day for 7 days, followed by a 21-day break, and the treatment cycle is repeated as provided herein.

In certain embodiments, the treatment is continued for at least 4 to 6 cycles. In certain embodiments, the treatment cycle is continued until a complete or partial response is observed in the treated subject. In certain embodiments, the treatment cycle is continued as long as the treated subject continues to benefit. In certain embodiments, the treated subjects are monitored for hematologic response and renal toxicities, and the dosage is delayed or reduced (e.g., by about 33%, about 50%, about 67%, or about 75%, in the next cycle), as appropriate.

In certain embodiments, the cytidine analog, e.g., 5-azacytidine or decitabine, is not co-administered with a cytidine deaminase inhibitor. In certain embodiments, the formulation comprising a cytidine analog as provided herein is not co-administered with THU. Certain embodiments herein provide methods of treating a disease or disorder provided herein (e.g., a disease associated with abnormal cell proliferation) comprising parenterally administering a cytidine analog provided herein (e.g., 5-azacytidine or decitabine), wherein the methods comprise not co-administering a cytidine deaminase inhibitor with the cytidine analog. Certain embodiments herein provide methods of treating a disease or disorder provided herein (e.g., a disease associated with abnormal cell proliferation) comprising parenterally administering a cytidine analog provided herein (e.g., 5-azacytidine or decitabine), wherein the methods avoid adverse effects associated with administering a cytidine deaminase inhibitor (e.g., THU) by not co-administering the cytidine deaminase inhibitor with the cytidine analog. In particular embodiments, a cytidine deaminase inhibitor (e.g., THU) is co-administered with the cytidine analog in an amount of, e.g., less than about 500 mg/d, less than about 200 mg/d, less than about 150 mg/d, less than about 100 mg/d, less than about 50 mg/d, less than about 25 mg/d, less than about 10 mg/d, less than about 5 mg/d, less than about 1 mg/d, or less than about 0.1 mg/d.

5. Methods of Co-Administration of Additional Therapeutic Agents

Certain embodiments herein provide methods of treating diseases or disorders disclosed herein (e.g., diseases or disorders involving abnormal cell proliferation), wherein the methods comprise co-administering a parenteral formulation disclosed herein (such as, for example, a formulation comprising 5-azacytidine, or a formulation comprising decitabine) with one or more additional therapeutic agents (such as, for example, a cancer therapeutic agent) to yield a synergistic therapeutic effect. In certain embodiments, the additional therapeutic agent is co-administered concurrently with a parenteral formulation provided herein. In certain embodiments, the additional therapeutic agent is co-administered sequentially (e.g., prior to or following the administration of a parenteral formulation provided herein). Particular co-administered therapeutic agents useful in the methods disclosed herein are disclosed throughout the specification. In particular embodiments, the additional therapeutic agent is co-administered in an amount that is a therapeutically effective amount. In particular embodiments, the additional therapeutic agent is co-administered in a separate dosage form from the cytidine analog dosage form with which it is co-administered. In particular embodiments, the additional therapeutic agent is co-administered in a dosage form (e.g., a single unit dosage form) together with the cytidine analog with which it is co-administered. In such cases, the cytidine analog (e.g., 5-azacytidine or decitabine) and the additional therapeutic agent may be co-formulated together in the same dosage form using methods of co-formulating active pharmaceutical ingredients, including methods disclosed herein and methods known in the art.

6. Additional Therapeutic Agents

In particular embodiments, the cytidine analog formulations provided herein further comprise one, two, three, or more other pharmacologically active substances (also termed herein "additional therapeutic agents," "second active agents," or the like). In particular embodiments, the formulations provided herein comprise the additional therapeutic agent(s) in a therapeutically effective amount. In particular embodiments, the cytidine analog (e.g., 5-azacytidine or decitabine) and the additional therapeutic agent(s) are co-formulated together in the same dosage form using methods of co-formulating active pharmaceutical ingredients, including methods disclosed herein and methods known in the art. In other embodiments, the cytidine analog and the additional therapeutic agent(s) are co-administered in separate dosage forms. It is believed that certain combinations work synergistically in the treatment of particular diseases or disorders, including, e.g., types of cancer and certain diseases and conditions associated with, or characterized by, undesired angiogenesis or abnormal cell proliferation. Cytidine analog dosage forms provided herein can also work to alleviate adverse effects associated with certain second active agents, and some second active agents can be used to alleviate adverse effects associated with cytidine analog dosage forms provided herein. In certain embodiments, the formulations provided herein are co-administered with one or more therapeutic agents to provide a resensitization effect in subjects in need thereof. Additional therapeutic agents can be, e.g., large molecules (e.g., proteins) or small molecules (e.g., synthetic inorganic, organometallic, or organic molecules).

Examples of particular additional therapeutic agents useful in the compositions and methods disclosed herein include, but are not limited to, e.g., cytotoxic agents, anti-metabolites, antifolates, HDAC inhibitors (e.g., entinostat, also known as SNDX-275 or MS-275; or vorinostat, also known as suberoylanilide hydroxamic acid (SAHA) or N-hydroxy-N-phenyloctanediamide), DNA intercalating agents, DNA cross-linking agents, DNA alkylating agents, DNA cleaving agents, topoisomerase inhibitors, CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiments, the co-administered therapeutic agent is an immunomodulatory compound, e.g., thalidomide, lenalidomide, or pomalidomide. The co-administered agent may be dosed, e.g., orally or by injection.

Other examples of additional therapeutic agents include, but are not limited to, hematopoietic growth factor, a cytokine, an anti-cancer agent, granulocyte colony-stimulating factor (G-CSF), granulocyte-macrophage colony-stimulating factor (GM-CSF), erythropoietin (EPO), interleukin (IL), interferon (IFN), oblimersen, melphalan, topotecan, pentoxifylline, taxotere, paclitaxel (e.g., Abraxane®), docetaxel, irinotecan, ciprofloxacin, doxorubicin, vincristine, dacarbazine, Ara-C, vinorelbine, prednisone, cyclophosphamide, bortezomib, arsenic trioxide. Such additional therapeutic agents are particularly useful in methods and compositions disclosed herein including, but not limited to, those relating to treatment of multiple myeloma.

Other examples of additional therapeutic agents include, but are not limited to, an antibody (e.g., rituximab, anti-CD33), hematopoietic growth factor, cytokine, anti-cancer agent, antibiotic, COX-2 inhibitor, immunomodulatory agent, immunosuppressive agent, corticosteroid, or a pharmacologically active mutant or derivative thereof. See, e.g., S, N and et al., *Leukemia and Lymphoma*, 2008, 49(11):2141-47 (describing a Phase II study involving the administration of a combination of hydroxyurea, 5-azacytidine and low dose gemtuzumab ozogamicin to elderly patients with AML and high-risk MDS, and concluding that this combination appears to be a safe and effective regimen in the treatment of AML and high risk MDS in this group of patients). Such additional therapeutic agents are particularly useful in methods and compositions disclosed herein including, but not limited to, those relating to treatment of the diseases and disorders disclosed herein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Embodiments herein encompass the use of native, naturally occurring, and recombinant proteins. Particular embodiments encompass mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the formulations comprising cytidine analogs disclosed herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Formulations comprising cytidine analogs disclosed herein can also comprise, be combined with, or used in combination with anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., *Curr. Opinion Mol. Ther.* 3(1):77-84 (2001).

In one embodiment, the additional therapeutic agent (e.g., large-molecule compound or small-molecule compound) reduces, eliminates, or prevents an adverse effect associated with the administration of a cytidine analog provided herein. Depending on the particular cytidine analog and the disease or disorder begin treated, adverse effects can include, but are not limited to, anemia, neutropenia, febrile neutropenia, thrombocytopenia, hepatotoxicity (e.g., including, but not limited to, hepatotoxicity in patients with preexisting hepatic impairment), elevated serum creatinine, renal failure, renal tubular acidosis, hypokalemia, hepatic coma, nausea, vomiting, dyspepsia, abdominal pain, pyrexia, leukopenia, diarrhea, constipation, ecchymosis, petechiae, rigors, weakness, pneumonia, anxiety, insomnia, lethargy, and decrease in weight, among others known in the art to be associated with particular cytidine analogs.

Like some large molecules, many small-molecule compounds are believed to be capable of providing a synergistic effect when administered with (e.g., before, after or simultaneously) a cytidine analog formulation disclosed herein. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; 5-azacytidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminol evulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B;

example, the aqueous solubility of 5-azacytidine at 25° C. is about 14 mg/mL, whereas the aqueous solubility of 5-azacytidine at 5° C. is about 6.4 mg/mL.

5-Azacytidine decomposes in the presence of water. The hydrolytic degradation pathway of 5-azacytidine may be described as the following:

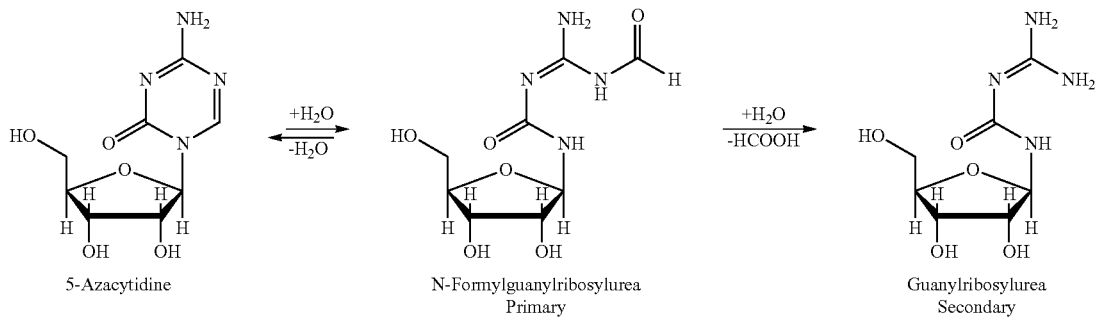

velaresol; veramine; verdins; verteporfin; vinorelbine; vinxaltine; vitaxin; vorozole; zanoterone; zeniplatin; zilascorb; and zinostatin stimalamer.

In other embodiments, specific additional therapeutic agents include, but are not limited to, lenalidomide, pomalidomide, and thalidomide. In yet another embodiment, specific additional therapeutic agents include, but are not limited to, taxane, paclitaxel, docetaxel, paclitaxel protein-bound particles (e.g., Abraxane®), or docetaxel protein-bound particles. In yet another embodiment, specific additional therapeutic agents include, but are not limited to, a platinum agent (e.g., carboplatin).

Specific additional therapeutic agents include, but are not limited to, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

INCORPORATION BY REFERENCE

All disclosures (e.g., patents, publications, and web pages) referenced throughout this specification are incorporated by reference in their entireties.

VII. EXAMPLES

A. 5-Azacytidine Chemistry

Figure 1:
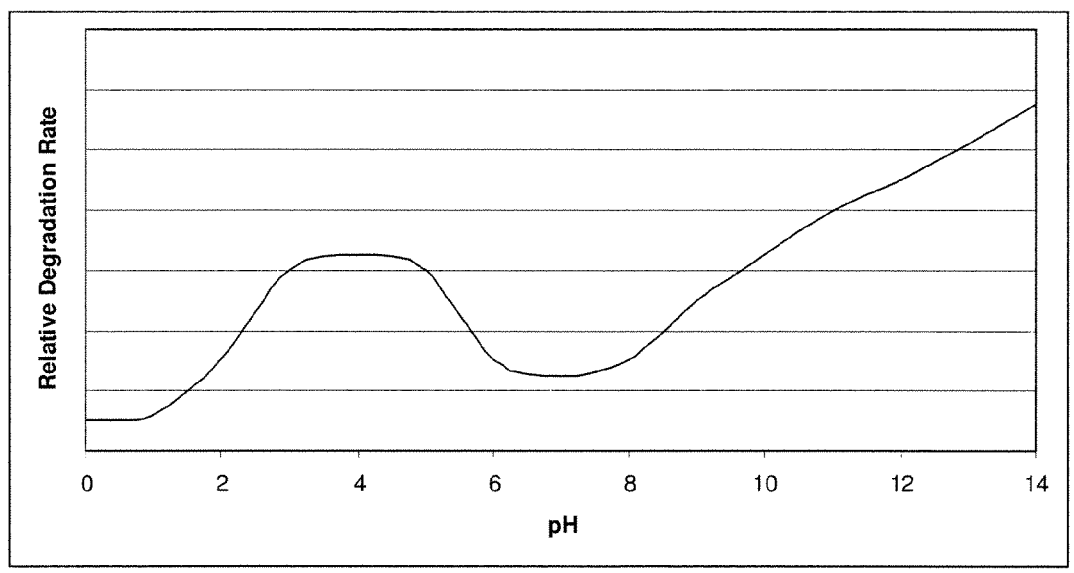
FIG. 1 represents relative degradation rate of 5-azacytidine at different pH conditions.
Figure 2:
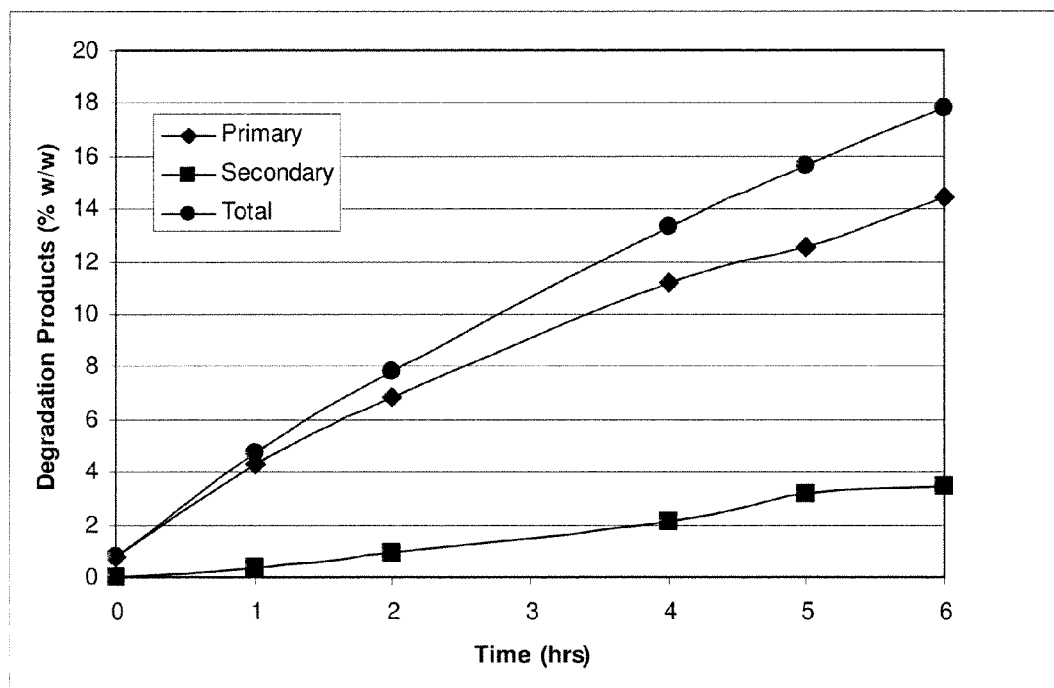
FIG. 2 represents a representative degradation profile of 5-azacytidine in water at about 25° C.

The pKa of 5-azacytidine is about 2.8 and 10.2 at 25° C. The aqueous solubility of 5-azacytidine depends on factors such as temperature. Generally at lower temperature a smaller amount of 5-azacytidine may be dissolved in water. For Generally, the 5-azacytosine ring in 5-azacytidine decomposes in the presence of water to yield a primary degradation product, N-formylguanyribosylurea, which further decomposes to yield a secondary degradation product, guanylribosylurea. The relative degradation rate of 5-azacytidine varies with pH. FIG. 1 represents the relative degradation rate of 5-azacytidine as a function of pH. FIG. 2 represents a typical degradation profile of 5-azacytidine in water at about 25° C.

B. 5-Azacytidine Degradation Kinetics

The aqueous degradation kinetics of 5-azacytidine was evaluated. The degradation kinetics of 5-azacytidine appeared to be affected by both temperature and solubility. Table 3 summarizes the degradation rates of an aqueous solution of 5-azacytidine and an aqueous suspension of 5-azacytidine at different temperatures. At lower temperatures, the degradation of 5-azacytidine is slower. In addition, at lower temperatures, the degradation rate of a solution of 5-azacytidine is significantly higher than that of a suspension of 5-azacytidine. The results indicated that 5-azacytidine in solution is available for degradation. At lower temperatures, solution-solid exchange kinetics appeared to significantly influence overall degradation kinetics.

TABLE 3

5-Azacytidine Degradation Rates

| | Degradation Rate (% per hour) | |
|---|---|---|
| State | 2° C. to 8° C. | 25° C. |
| Solution | 0.7% | 2.8% |
| Suspension | 0.1% | 2.5% |

Figure 3:
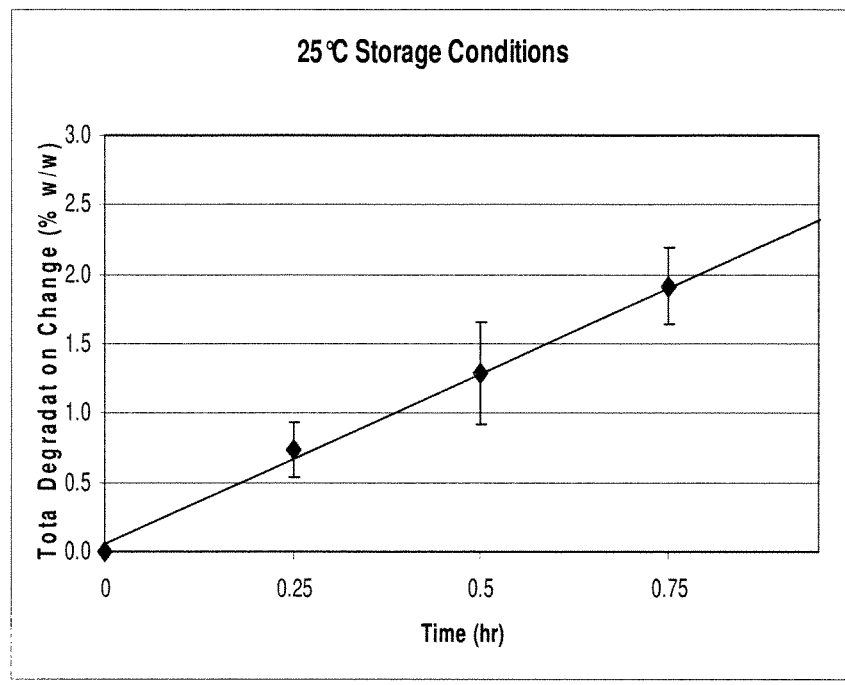
FIG. 3 represents degradation profiles of lyophilized powder containing 5-azacytidine and mannitol reconstituted with room temperature Water-For-Injection (WFI) and stored at two different temperature conditions.
Figure 3:
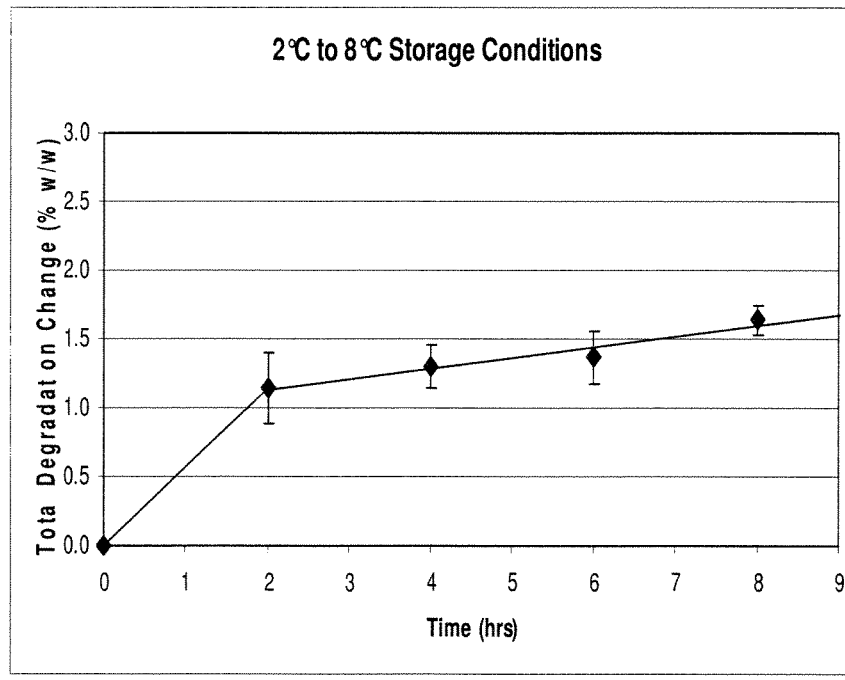

A lyophilized powder of about 100 mg 5-azacytidine and about 100 mg mannitol was reconstituted with sterile Water for Injection at about room temperature. The reconstituted product was stored at about 25° C. or about 2-8° C. The degradation profiles of the reconstituted products was analyzed. FIG. 3 represents the degradation profile upon storage at the two different temperature conditions.

C. Activity and Safety of Degradation Products of 5-Azacytidine

The primary and secondary degradation products as shown in Example A were evaluated for activity and toxicity in a leukemic mouse model. The primary degradation product was dosed at about 240 mg/m², and showed about 25% of the activity and toxicity of 5-azacytidine. The secondary degradation product was dosed at 1440 mg/m², and showed neither activity nor toxicity.

D. Human Pharmacokinetics of 5-Azacytidine

Figure 4:
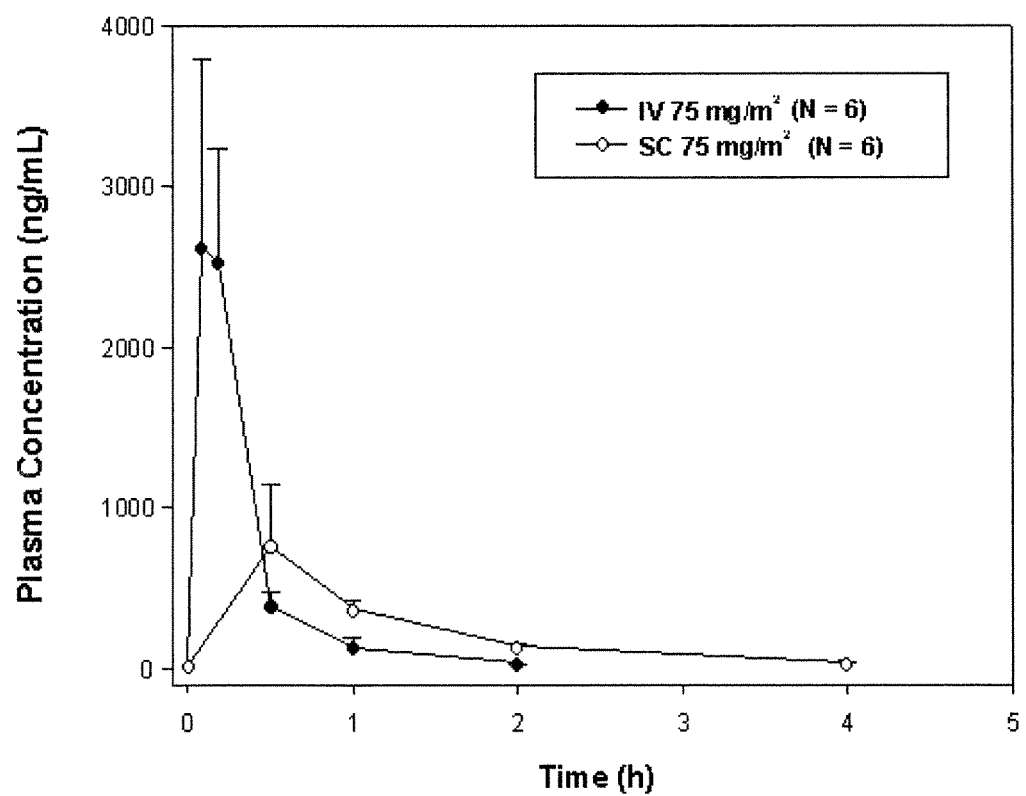
FIG. 4 represents a representative human pharmacokinetics profile of 5-azacytidine following SC or IV dosing.

Representative human pharmacokinetics profiles of 5-azacytidine after SC or IV dosing are presented in FIG. 4. The relative bioavailability of SC dose (relative to IV dose) is about 90%. The $C_{max}$ for SC dosing is rapid, which is consistent with the solubility and stability profile of 5-azacytidine.

E. Effect of Reconstitution with Cold Water on the Stability and Purity of the Resulting 5-Azacytidine Suspension A study was conducted to evaluate the stability of 5-azacytidine reconstituted with cold water, for example, cold Water for Injection. The reconstituted suspension of 5-azacytidine was then stored either refrigerated or frozen.

In one experiment, the suspension was stored at a temperature of between about 2° C. and about 8° C. for up to 72 hours, and then warmed to about 25° C. over a period of about 30 minutes. In another experiment, the suspension was stored at a temperature of about −20° C. for up to 7 days, and then thawed and stored refrigerated for up to 48 hours, and then warmed to about 25° C. over a period of about 30 minutes.

In these experiments, vials containing lyophilized powder of about 100 mg of 5-azacytidine and about 100 mg of mannitol were used. The dry lyophilized powder was stored in the vials under normal conditions for about 48 months prior to use in this experiment.

The contents of the vials were reconstituted with cold Water for Injection. Prior to reconstitution, the Water for Injection was stored refrigerated for at least 24 hours. All vials were reconstituted into an opaque, white suspension within 20 seconds.

The vials were stored at conditions described above for a certain time. The contents of all vials were re-dispersed into an opaque, white suspension within 20 seconds of shaking after each storage conditions or time points described in this example.

Figure 5:
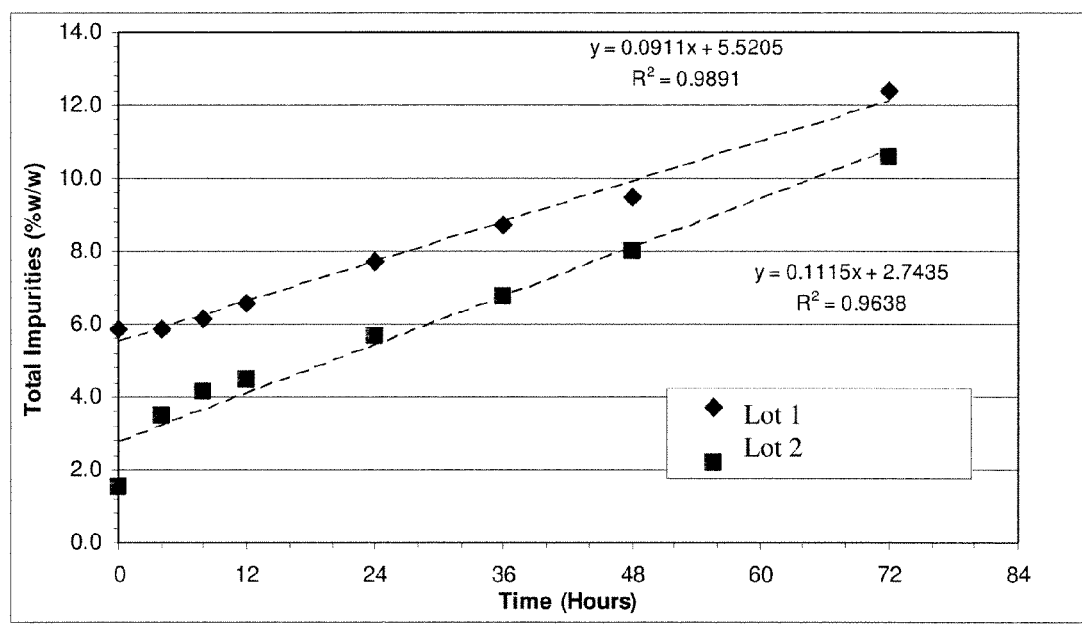
FIG. 5 represents a purity profile of a 5-azacytidine suspension after reconstitution with cold WFI and storage at a temperature of between about 2° C. and about 8° C. for up to 72 hours.
Figure 6:
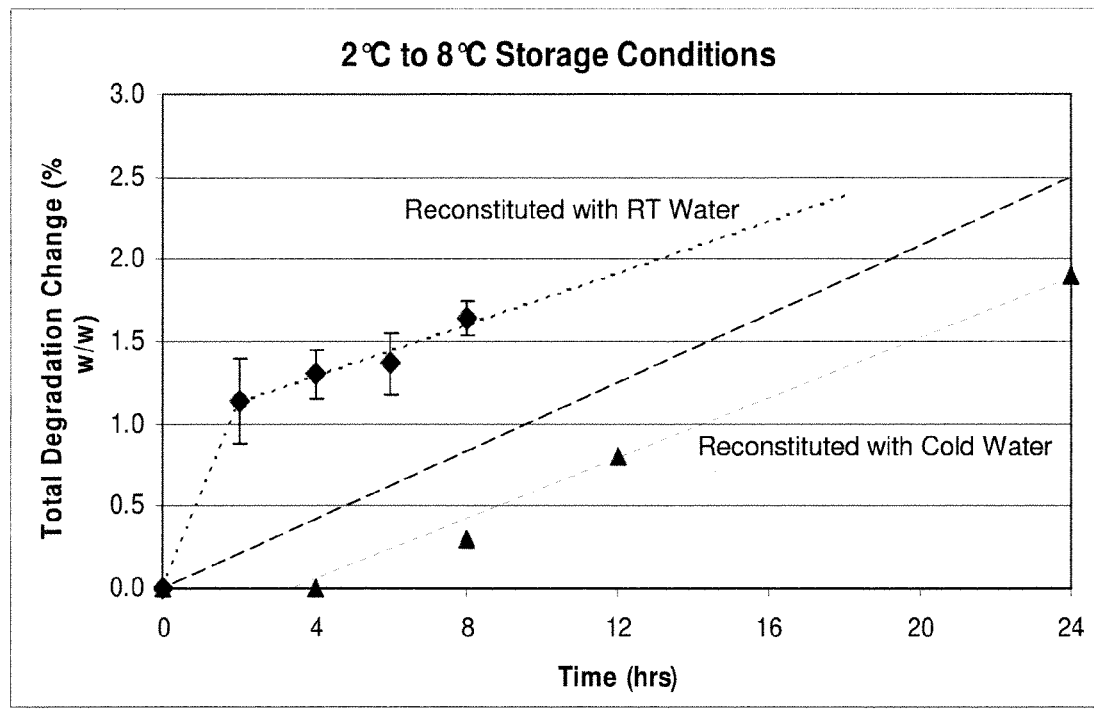
FIG. 6 represents the degradation profiles of 5-azacytidine suspensions after reconstitution with either room temperature water or cold water, and followed by storage at a temperature of between about 2° C. and about 8° C. for up to 24 hours.
Figure 7:
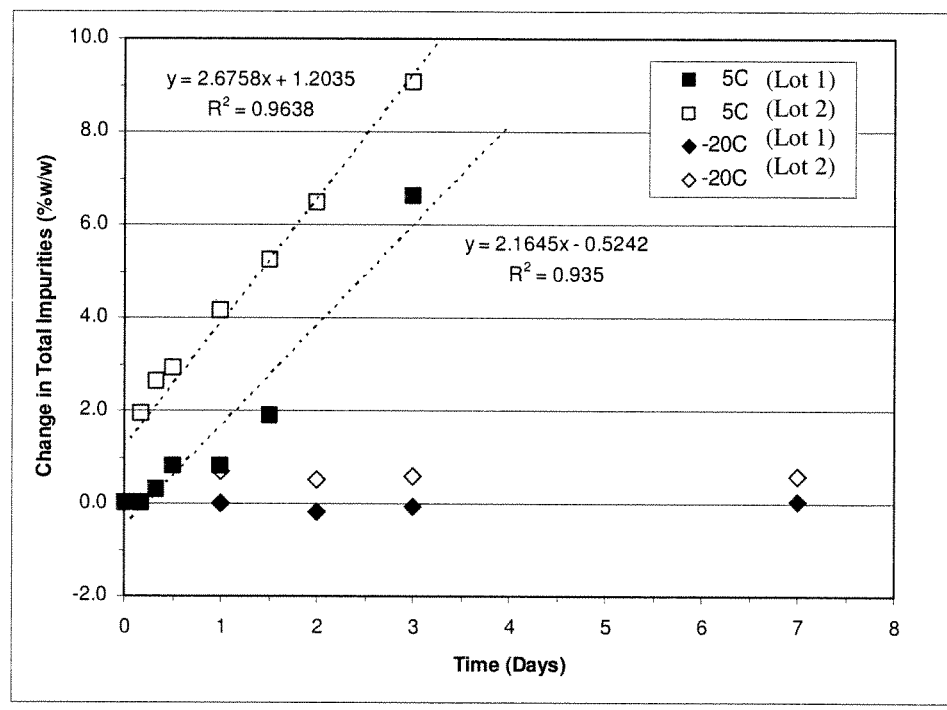
FIG. 7 represents the effect of storage temperature and time on the purity profile of 5-azacytidine suspensions after storage at either about 5° C. or about −20° C.

The results of these experiments are presented in FIGS. 5-8. FIG. 5 represents the purity profile of 5-azacytidine suspension after reconstitution with cold Water for Injection and storage at a temperature of between about 2° C. and about 8° C. for up to 72 hours. FIG. 6 represents a comparison of the degradation profiles of 5-azacytidine suspensions after reconstitution with room temperature water vs. cold water and storage at a temperature of between about 2° C. and about 8° C. for up to 24 hours. FIG. 7 illustrates the effect of storage temperature and time on the purity profile of 5-azacytidine suspension after storage at about 5° C. or about −20° C. FIG. 8 represents the purity profile of 5-azacytidine suspension after reconstitution with cold Water for Injection and storage first at a temperature of about −20° C. for 24 hours and then at a temperature of between about 2° C. and about 8° C. for up to about 48 hours.

The results showed that when reconstituted with cold Water for Injection and stored refrigerated, 5-azacytidine degraded at a rate of about 0.12% w/w per hour. When reconstituted with cold Water for Injection and stored frozen, 5-azacytidine showed no significant degradation for at least 7 days. In addition, freezing the reconstituted product did not affect 5-azacytidine degradation behavior or the redispersability of the suspension after thawing.

Thus, these experiments suggested that the degradation rate of 5-azacytidine decreased with decrease in temperature. Reconstituting 5-azacytidine lyophilized powder with cold water, for example, cold Water for Injection, resulted in decreased 5-azacytidine degradation in the resulting suspension.

F. Cold Water Reconstitution of VIDAZA® with Subsequent Refrigerated Storage

This study assessed whether the stability of 5-azacytidine suspension can be prolonged when reconstituted with refrigerated Water For Injection (WFI) followed by storage under refrigerated conditions.

Two lots of Vidaza® (5-azacytidine or azacitidine) were reconstituted with refrigerated (2-8° C.) WFI to form a suspension and immediately stored refrigerated (2-8° C.). After storage for 16, 18, 20, or 22 hours, azacitidine suspension was then placed at a constant 25° C. for 30 minutes then tested for potency, redispersibility time, and suspension appearance. Sterility testing was performed at the end of the study. Stability of azacitidine was defined in this study as not more than 3% loss of potency from Time 0 (e.g., baseline).

Azacitidine reconstituted with cold water (2-8° C.) followed by refrigerated storage (2-8° C.) and 30 minutes equilibration to 25° C. remained stable from baseline to about 22 hr with a maximum loss of potency of 2.7% for each of the two lots of drug evaluated. At the 16, 18, 20, and 22 hr study time points and 30 minutes equilibration to 25° C., redispersion time was 0.3 minutes with the appearance of fine white particles in suspension. All reconstituted vials stored refrigerated (2-8° C.) passed sterility testing at the end of study.

Because azacitidine is rapidly degraded in water, Vidaza® is typically reconstituted with sterile WFI to form a suspension and then administered within 45 minutes if stored at 25° C. After reconstitution with sterile WFI, azacitidine suspension may be refrigerated (2-8° C.) for up to 8 hours. Reconstituted under these conditions and times, azacitidine may maintain >90% potency. However, the present study showed that reconstitution of azacitidine with cold WFI together with subsequent refrigerated storage was associated with about a threefold prolongation in the stability time of the drug from 8 to 22 hours. This substantial increase in the time of azacitidine maintaining >90% potency (or for example, not more than 3% loss of potency from Time 0 (e.g., baseline)) allows for prolonged in-use time that may provide for more convenience for pharmacists and patients.

Analytical methods and stability testing: The potency of azacitidine was determined by quantitating the sample against an external standard utilizing reverse phase chromatography with UV detection, in accordance with ICH guidelines. The determination of suspension appearance for redispersibility time was performed visually, in accordance with ICH guidelines.

Stability testing of azacitidine was performed by utilizing validated regulatory accepted analytical methods in accordance with ICH guidelines. These studies were conducted at conditions which encompass long-term, intermediate and accelerated storage of the drug product over a period of time.

Materials and methods: Two lots of sterile commercial scale azacitidine drug product, each nearing the end of their expiry period of 48 months, were used for the study. Each lot of drug product was prepared as a homogeneous mixture of lyophilized powder and placed in labeled vials in preparation for reconstitution. Vials from each lot of azacitidine drug product were then reconstituted with 4 mL of refrigerated (2-8° C.) WFI and immediately placed in refrigerated storage (2-8° C.). After refrigerated storage for 16, 18, 20, and 22 hours, reconstituted vials of azacitidine were removed from refrigeration and placed at 25° C. for 30 minutes. Equilibration time to 25° C. for refrigerated azacitidine suspension was determined to be 30 minutes. After 16, 18, 20, and 22 hours of refrigerated storage and 30 minutes equilibration to 25° C., the reconstituted vials were shaken vigorously and tested for potency, redispersibility time, and appearance of the suspension. Stability of azacitidine was defined in this study as not more than 3% loss of potency from Time 0 (e.g., baseline). Sterility of the refrigerated drug product was assessed for reconstituted vials stored at 2-8° C. at end of study.

Results: After cold water (2-8° C.) reconstitution and refrigerated storage (2-8° C.) followed by 30 minutes equilibration to 25° C., azacitidine remained stable from baseline to 22 hours with a maximum loss of potency of 2.7% for each of the 2 lots of drug product evaluated, see Table 4 below. At the 16, 18, 20, and 22 hour study time points and 30 minutes equilibration to 25° C., redispersion time was 0.3 minutes with the appearance of fine white particles in suspension and the absence of clumps. All reconstituted vials stored refrigerated (2-8° C.) passed sterility testing at end of study.

The results of this study show that the stability (e.g., not more than 3% loss of potency from Time 0 (e.g., baseline)) and usage time of reconstituted azacitidine can be prolonged nearly threefold from 8 hours to 22 hours using cold water (2-8° C.) reconstitution followed by refrigerated (2-8° C.) storage. This reconstitution procedure showed no effects on redispersibility, appearance, or sterility after the prolonged refrigerated storage time. These findings have significant implications for providing expanded usage time with azacitidine for pharmacists and other caregivers.

was then stored under frozen conditions. Changes in appearance of suspension, reconstitution time, redispersibility time, and stability of reconstituted homogenized Vidaza® drug product, stored at various temperatures and hold times, were evaluated. A study to determine the thawing time of the frozen suspensions at 25° C. was also conducted.

Testing was performed using two lots of homogenized drug product. The first study examined and determined the thaw times of frozen reconstituted Vidaza® drug product at 25° C. The second study analyzed the reconstituted drug product after storage of reconstituted drug product at −20° C. utilizing hold times of 24, 48, and 72 hours followed by a post hold time of 45 minutes at 25° C. to allow for thawing as determined in the first study.

Results of the analyses are summarized in the tables below. The results support that azacitidine drug product vials reconstituted with refrigerated WFI and stored under frozen (−20° C.) conditions were stable for up to 72 hours.

Analytical Methods: The amount of azacitidine and related impurities contained in azacitidine samples was determined utilizing High Performance Liquid Chromatography (HPLC). Two methods were used to complete this testing. Both methods incorporated a gradient separation utilizing an acetonitrile/0.02 M potassium phosphate pH 6.5 buffer mobile phase system, column temperature of 25° C. and a sample tray temperature of 5° C. One method employed a Zorbax RX-C8, 250×4.6 mm, 5 μm column with a RX-C8, 12.5×4.6 mm, 5 μm guard column, a flow rate of 1.0 mL/min and ultraviolet detection at 214 nm. The other method employed a Zorbax RX-C8, 150×2.1 mm, 5 μm column with a RX-C8, 12.5×4.6 mm, 5 μm guard column, a flow rate of 0.5 mL/min and ultraviolet detection at 246 nm. Reconstitution

TABLE 4

Averaged* azacitidine assay stability‡ after cold WFI reconstitution and refrigerated storage (2-8° C.) from baseline (0 hr) to 22 hr

|  | Baseline for 3 vials* | Average % assay at BL | 16 hours for 3 vials* | Average % assay at 16 hours | 18 hours for 3 vials* | Average % assay at 18 hours | 20 hours for 3 vials* | Average % assay at 20 hours | 22 hours for 3 vials* | Average % assay at 22 hours |
|---|---|---|---|---|---|---|---|---|---|---|
| Lot 1 | | | | | | | | | | |
| Assay | 95.3% | 95.5% | 93.7% | 93.9% | 94.2% | 93.6% | 91.6% | 92.5% | 92.5% | 92.8% |
|  | 94.6% |  | 94.3% |  | 93.2% |  | 93.0% |  | 92.9% |  |
|  | 96.7% |  | 93.7% |  | 93.6% |  | 92.9% |  | 93.0% |  |
| % loss of assay from BL |  | — |  | 1.6% |  | 1.9% |  | 3.0% |  | 2.7% |
| Lot 2 | | | | | | | | | | |
| Assay | 95.2% | 95.2% | 94.6% | 93.7% | 93.6% | 92.7% | 92.8% | 92.9% | 93.7% | 92.5% |
|  | 94.5% |  | 93.2% |  | 93.3% |  | 92.6% |  | 91.9% |  |
|  | 95.9% |  | 93.3% |  | 91.1% |  | 93.4% |  | 91.9% |  |
| % loss of assay from BL |  | — |  | 1.5% |  | 2.5% |  | 2.3% |  | 2.7% |

*Each averaged percent comes from 3 vials of product;
‡Stability of Vidaza ® in this study is defined as not more than 3% loss of potency from Time 0 (e.g., baseline).

G. Cold Water Reconstitution of VIDAZA® with Subsequent Frozen Storage

This study assessed whether the stability of 5-azacytidine suspension can be prolonged when reconstituted with refrigerated Water For Injection (WFI) followed by storage under frozen conditions. The study was performed in a similar fashion as Example F, and the cold water reconstituted suspension and redispersibility times were determined in a manner similar to that as described in Example F. Appearance of the suspension was determined visually.

Two lots of sterile commercial scale azacitidine drug product were used for the study. Each lot of drug product was prepared as a homogeneous mixture of lyophilized powder and placed in labeled vials in preparation for reconstitution.

Study 1:

Five vials from each lot of azacitidine drug product were reconstituted with 4 mL of refrigerated (2-8° C.) WFI and immediately placed in a freezer (−20° C.) for 24 hours. After 24 hours, the frozen vials were placed in a 25° C. constant temperature oven. The temperature of each vial was recorded every 5 minutes using an infrared (IR) thermometer. The appearance of the contents of each vial, i.e., whether the contents were frozen and to what extent it was frozen, was also evaluated at this time. The temperature and appearance was evaluated every 5 minutes for each vial until the contents reached a temperature of approximately 25° C.

Results of this study showed that vial temperatures equilibrated to 24° C. in 55 to 70 minutes. Frozen suspension was thawed after 30 minutes. Disparity in temperatures was seen in some samples in both groups at each time-point, and the observation that some vials did not reach 25° C. after 70 minutes may be due to the oven door being opened/closed frequently to obtain vial temperatures/appearances. For the purposes of Study 2, a thaw time of 45 minutes was designated.

Study 2:

An appropriate number of homogenized azacitidine drug product vials were reconstituted with refrigerated WFI as described above, and placed in a freezer (−20° C.). After a storage time of 24, 48, and 72 hours, the vials were transferred to a 25° C. constant temperature oven and allowed to thaw for 45 minutes. After thawing, the contents of the vials were analyzed, for example, by HPLC. Testing was performed on the same day for all vials. This was accomplished by diluting/freezing the 72 hour samples on day 1, the 48 hour samples on day 2, the 24 hour samples on day 3, and analyzing all samples on day 4. In addition to the frozen vials, a set of drug product vials were reconstituted and diluted, and immediately analyzed for use as T0 (baseline). Dilution times were pre-determined and staggered so that the T0 samples would be analyzed first, the 24 hour samples would be analyzed second, the 48 hour samples third, and the 72 hour samples last. Reconstitution time, redispersion time and appearances of suspensions for each vial were also determined for these samples.

The 24 hour samples were diluted with room temperature WFI due to the WFI being left on the bench top after dilution of the 48 hour samples. After dilution of the 24 hour samples, the WFI was placed in the refrigerator to prepare for dilution of the T0 samples.

Results of this study can be found in the tables 5 and 6. Assay results (% label claim) were reported as per the method and corrected for the mass of the sample known to be present in each vial. All results for assay, related substances, reconstitution time, and redispersion time analyses passed current specification criteria. At the 24, 48, and 72 hr study time points and 45 minutes equilibration to 25° C., redispersion time was 0.3 minutes with the appearance of fine white particles in suspension. The assay results were further evaluated by applying a safety factor criteria where the change from T=0 to post extended storage was limited to not more that 2%. All assayed samples through the 72 hour time point for both drug product lots were within the 2% criteria. These results support that Vidaza® drug product vials reconstituted with refrigerated WFI and stored under frozen (−20° C.) conditions are stable for up to 72 hours. The samples after storage up to 72 hours at frozen conditions remained sterile.

TABLE 5

Averaged* azacitidine assay stability after cold WFI reconstitution and frozen storage (−20° C.) from baseline (0 hr) to 72 hr

| | Baseline for 3 vials* | Average % assay at BL | 24 hours for 3 vials* | Average % assay at 24 hours | 48 hours for 3 vials* | Average % assay at 48 hours | 72 hours for 3 vials* | Average % assay at 72 hours |
|---|---|---|---|---|---|---|---|---|
| | | | | Lot 1 | | | | |
| Assay | 97.2% | 97.2% | 96.3% | 96.3% | 96.7% | 97.2% | 96.2% | 95.8% |
| | 97.4% | | 96.1% | | 96.5% | | 96.3% | |
| | 97.2% | | 96.4% | | 98.4% | | 95.0% | |
| % loss of assay from BL | | — | | 0.9% | | 0% | | 1.4% |
| | | | | Lot 2 | | | | |
| Assay | 97.3% | 97.0% | 95.7% | 95.7% | 95.1% | 95.9% | 97.2% | 96.5% |
| | 96.4% | | 95.5% | | 95.8% | | 96.3% | |
| | 97.2% | | 96.0% | | 96.9% | | 96.0% | |
| % loss of assay from BL | | — | | 1.3% | | 1.1% | | 0.5% |

*Each averaged percent comes from 3 vials of product.

TABLE 6

Sterility Study

| | Lot 1, 24 hr Sample | | Lot 2, 24 hr Sample | | Lot 1, 72 hr Sample | | Lot 2, 72 hr Sample | |
|---|---|---|---|---|---|---|---|---|
| Vial # | Time† | Sterility | Time† | Sterility | Time† | Sterility | Time† | Sterility |
| 1 | 1 | Sterile | 1 | Sterile | 1 | Sterile | 1 | Sterile |
| 2 | 1 | Sterile | 1 | Sterile | 1 | Sterile | 1 | Sterile |
| 3 | 1 | Sterile | 1 | Sterile | 1 | Sterile | 1 | Sterile |
| 4 | 1 | Sterile | 1 | Sterile | 1 | Sterile | 1 | Sterile |

TABLE 6-continued

Sterility Study

| Vial # | Lot 1, 24 hr Sample | | Lot 2, 24 hr Sample | | Lot 1, 72 hr Sample | | Lot 2, 72 hr Sample | |
|---|---|---|---|---|---|---|---|---|
| | Time† | Sterility | Time† | Sterility | Time† | Sterility | Time† | Sterility |
| 5 | 1 | Sterile | 1 | Sterile | 1 | Sterile | 1 | Sterile |
| 6 | 1 | Sterile | 1 | Sterile | 1 | Sterile | 1 | Sterile |
| 7 | 1 | Sterile | 1 | Sterile | 1 | Sterile | 1 | Sterile |
| 8 | 1 | Sterile | 1 | Sterile | 1 | Sterile | 1 | Sterile |
| 9 | 1 | Sterile | 1 | Sterile | 1 | Sterile | 1 | Sterile |
| 10 | 1 | Sterile | 1 | Sterile | 1 | Sterile | 1 | Sterile |
| 11 | 1 | Sterile | 1 | Sterile | 1 | Sterile | 1 | Sterile |
| 12 | 1 | Sterile | 1 | Sterile | 1 | Sterile | 1 | Sterile |
| 13 | 1 | Sterile | 1 | Sterile | 1 | Sterile | 1 | Sterile |
| 14 | 1 | Sterile | 1 | Sterile | 1 | Sterile | 1 | Sterile |
| 15 | 1 | Sterile | 1 | Sterile | 1 | Sterile | 1 | Sterile |
| 16 | 1 | Sterile | 1 | Sterile | 2 | Sterile | 1 | Sterile |
| 17 | 2 | Sterile | 1 | Sterile | 2 | Sterile | 1 | Sterile |
| 18 | 2 | Sterile | 2 | Sterile | 2 | Sterile | 1 | Sterile |
| 19 | 2 | Sterile | 2 | Sterile | 3 | Sterile | 2 | Sterile |
| 20 | 3 | Sterile | N/A | Sterile | 3 | Sterile | 3 | Sterile |

†Time in this column stands for reconstitution time in minutes.

The present disclosure has been described in connection with certain embodiments and examples; however, unless otherwise indicated, the claimed invention should not be unduly limited to such specific embodiments and examples.

What is claimed is:

1. A liquid pharmaceutical composition comprising 5-azacytidine prepared by reconstituting with cold sterile water, which is substantially free of impurities, wherein the liquid pharmaceutical composition is a suspension, wherein the cold sterile water is at a temperature of less than about 8° C.

2. The pharmaceutical composition of claim 1, which is prepared by contacting the cold sterile water with a sterile lyophilized powder comprising 5-azacytidine.

3. The pharmaceutical composition of claim 1, which is a single unit dosage form.

4. The pharmaceutical composition of claim 2, wherein the cold sterile water is at a temperature of between about 2° C. and about 8° C.

5. The pharmaceutical composition of claim 2, wherein the sterile lyophilized powder comprises 5-azacytidine and mannitol.

6. The pharmaceutical composition of claim 5, wherein the weight ratio of 5-azacytidine and mannitol in the sterile lyophilized powder is about 1:1.

7. The pharmaceutical composition of claim 6, wherein the sterile lyophilized powder comprises about 100 mg of 5-azacytidine and about 100 mg of mannitol.

8. The pharmaceutical composition of claim 2, wherein the composition is stored at a temperature of less than about 8° C., or at a temperature of between about 2° C. and about 8° C., or at a temperature of about 5° C., or at a temperature of about 0° C.

9. The pharmaceutical composition of claim 8, wherein the composition is stored for up to 16 hr, up to 18 hr, up to 20 hr, up to 22 hr, or up to 24 hr.

10. The pharmaceutical composition of claim 9, wherein the composition is warmed to about 12° C., about 14° C., about 16° C., about 18° C., about 20° C., about 22° C., about 24° C., about 25° C., about 26° C., about 28° C., or about 30° C., prior to parenteral use.

11. The pharmaceutical composition of claim 10, which is substantially free of impurities.

12. The pharmaceutical composition of claim 2, wherein the composition is stored frozen at a temperature of less than 0° C., or at a temperature of about −20° C.

13. The pharmaceutical composition of claim 12, wherein the composition is stored for about 1, 2, 3, 4, 5, 6, or 7 days.

14. The pharmaceutical composition of claim 13, wherein the composition is warmed to about 12° C., about 14° C., about 16° C., about 18° C., about 20° C., about 22° C., about 24° C., about 25° C., about 26° C., about 28° C., or about 30° C., prior to parenteral use.

15. The pharmaceutical composition of claim 14, which is substantially free of impurities.

16. A method for treating a disease associated with abnormal cell proliferation, comprising parenterally administering to a subject in need thereof a pharmaceutical composition of claim 2.

17. The method of claim 16, wherein the disease is myelodysplastic syndrome.

18. The method of claim 16, wherein the disease is acute myelogenous leukemia.

19. The method of claim 16, wherein the disease is non-small cell lung cancer, ovarian cancer, pancreatic cancer, or colorectal cancer.

20. The method of claim 16, wherein the method further comprises co-administering to the subject an additional therapeutic agent.

21. The method of claim 20, wherein the additional therapeutic agent is thalidomide, lenalidomide, or pomalidomide.

22. The method of claim 16, wherein the amount of 5-azacytidine is about 10 mg/m$^2$, about 15 mg/m$^2$, about 20 mg/m$^2$, about 25 mg/m$^2$, about 30 mg/m$^2$, about 45 mg/m$^2$, about 50 mg/m$^2$, about 75 mg/m$^2$, or about 100 mg/m$^2$.

23. A method of preparing a liquid pharmaceutical composition comprising 5-azacytidine, comprising the step of contacting cold sterile water with a sterile lyophilized powder comprising 5-azacytidine, wherein the cold sterile water is at a temperature of less than about 8° C.

24. The method of claim 23, wherein the cold sterile water is at a temperature of between about 2° C. and about 8° C.

25. The method of claim 23, wherein the sterile lyophilized powder further comprises mannitol.

26. The method of claim 25, wherein the sterile lyophilized powder comprises about 100 mg of 5-azacytidine and about 100 mg of mannitol.

27. The method of claim 23, further comprising the step of storing the liquid pharmaceutical composition at a temperature of less than about 8° C., or at a temperature of between about 2° C. and about 8° C., or at a temperature of about 5° C., or at a temperature of about 0° C.

28. The method of claim 27, wherein the composition is stored for up to 16 hr, up to 18 hr, up to 20 hr, up to 22 hr, or up to 24 hr.

29. The method of claim 28, further comprising the subsequent step of warming the pharmaceutical composition to about 12° C., about 14° C., about 16° C., about 18° C., about 20° C., about 22° C., about 24° C., about 25° C., about 26° C., about 28° C., or about 30° C., prior to parenteral use.

30. The method of claim 29, wherein the pharmaceutical composition is substantially free of impurities.

31. The method of claim 29, wherein the pharmaceutical composition remains sterile.

32. The method of claim 23, further comprising the step of storing the liquid pharmaceutical composition frozen at a temperature of less than 0° C., or at a temperature of about −20° C.

33. The method of claim 32, wherein the composition is stored for about 1, 2, 3, 4, 5, 6, or 7 days.

34. The method of claim 33, further comprising the subsequent step of warming the pharmaceutical composition to about 12° C., about 14° C., about 16° C., about 18° C., about 20° C., about 22° C., about 24° C., about 25° C., about 26° C., about 28° C., or about 30° C., prior to parenteral use.

35. The method of claim 34, wherein the pharmaceutical composition is substantially free of impurities.

36. The method of claim 35, wherein the pharmaceutical composition remains sterile.

\* \* \* \* \*